US011529404B2

(12) United States Patent
Vaughan et al.

(10) Patent No.: US 11,529,404 B2
(45) Date of Patent: *Dec. 20, 2022

(54) DOUBLY ATTENUATED LATE LIVER STAGE MALARIA PARASITES AND RELATED COMPOSITIONS AND METHODS

(71) Applicant: SEATTLE CHILDREN'S HOSPITAL, Seattle, WA (US)

(72) Inventors: Ashley M. Vaughan, Seattle, WA (US); Stefan H. I. Kappe, Seattle, WA (US); Dorender A. Dankwa, Seattle, WA (US)

(73) Assignee: SEATTLE CHILDREN'S HOSPITAL, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/163,932

(22) Filed: Feb. 1, 2021

(65) Prior Publication Data

US 2021/0353731 A1    Nov. 18, 2021

Related U.S. Application Data

(63) Continuation of application No. 16/480,615, filed as application No. PCT/US2018/015096 on Jan. 24, 2018, now Pat. No. 10,905,753.

(60) Provisional application No. 62/450,258, filed on Jan. 25, 2017.

(51) Int. Cl.
| | |
|---|---|
| *A61K 39/002* | (2006.01) |
| *A61K 39/015* | (2006.01) |
| *C07K 14/445* | (2006.01) |
| *C12N 1/36* | (2006.01) |
| *A61K 39/00* | (2006.01) |

(52) U.S. Cl.
CPC .......... *A61K 39/015* (2013.01); *C07K 14/445* (2013.01); *C12N 1/36* (2013.01); *A61K 2039/522* (2013.01); *C12N 2310/20* (2017.05)

(58) Field of Classification Search
None
See application file for complete search history.

(56) References Cited

U.S. PATENT DOCUMENTS

2015/0313980 A1    11/2015   Janse et al.

FOREIGN PATENT DOCUMENTS

WO    2009/026574 A2    2/2009

OTHER PUBLICATIONS

International Search Report and Written Opinion, dated Apr. 13, 2018, issued in corresponding International Application No. PCT/US2018/015096, filed Jan. 24, 2018, 11 pages.
Dankwa, D.A., et al., "A Plasmodium yoelii Mel2-Like RNA Binding Protein Is Essential for Completion of Liver Stage Schizogony," Infection and Immunity 84(5):1336-1345, May 2016.
Kumar, H., et al., "Protective Efficacy and Safety of Liver Stage Attenuated Malaria Parasites," Scientific Reports 5:26824, May 2016, pp. 1-9.
Otto, T.D., et al., "A Comprehensive Evaluation of Rodent Malaria Parasite Genomes and Gene Expression," BMC Biology 12(86):1-18, Oct. 2014.
Sato, Y., et al., "Comparative Plasmodium Gene Overexpression Reveals Distinct Perturbation of Sporozoite Transmission by Profilin," Molecular Biology of the Cell 27(14):2234-2244, May 2016.
Annoura, T., et al., Two Plasmodium 6-Cys Family-Related Proteins Have Distinct and Critical Roles in Liver-Stage Development. FASEB J 28:2158-2170, May 2014.
Orito, Y., et al., Liver-specific Protein 2: a Plasmodium Protein Exported to the Hepatocyte Cytoplasm and Required for Merozoite Formation. Mol Microbiol 87(1):66-79, Jan. 2013.
International Preliminary Report on Patentability, dated Aug. 8, 2019, issued in corresponding International Application No. PCT/US2018/015096, filed Jan. 24, 2018, 8 pages.
Bijker, E.M., et al., "Novel Approaches to Whole Sporozoite Vaccination Against Malaria," 33(52): 7462-7468, Oct. 2015.
Extended European Search Report dated Aug. 13, 2020, issued in corresponding European Patent Application No. 18744597.8, filed Jan. 24, 2018, 7 pages.
Goswami, D., et al., "A Replication-Competent Late Liver Stage-Attenuated Human Malaria Parasite," JCI Insight 5(13):1-19, Jul. 2020.
Kreutzfeld, O., et al., "Engineering of Genetically Arrested Parasites (GAPs) For a Precision Malaria Vaccine," Frontiers in Cellular and Infection Microbiology 7(198):1-13, May 2017.
Singer, M., et al., "Time for Genome Editing: Next-Generation Attenuated Malaria Parasites," Trends in Parasitology, Cell Press, 33(3):202-213, Oct. 2016.
Vaughan, A.M., et al., "A Plasmodium Parasite with Complete Late Liver Stage Arrest Protects Against Preerythrocytic and Erythrocytic Stage Infection in Mice," Infection and Immunity 86(5):1-18, Feb. 2018.

*Primary Examiner* — Jennifer E Graser
(74) *Attorney, Agent, or Firm* — Christensen O'Connor Johnson Kindness PLLC

(57) ABSTRACT

The disclosure relates to doubly attenuated malaria parasites that have had the functionality of LISP2 and PlasMei2 genes interrupted through genetic manipulation. The double attenuated malaria parasites disclosed herein are useful for methods and compositions for stimulating of vertebrate host immune systems because of the complete cessation of lifecycle progression in the late liver stage, while providing a comprehensive antigenic presentation representing wild-type liver stage parasites. The disclosure also relates to the additional blood stage and gametocyte antigens to compositions of genetically attenuated malaria parasites (GAPs) to enhance efficient immune stimulation and prevention of disease and transmission related to the presence of blood stage parasites.

19 Claims, 13 Drawing Sheets

Specification includes a Sequence Listing.

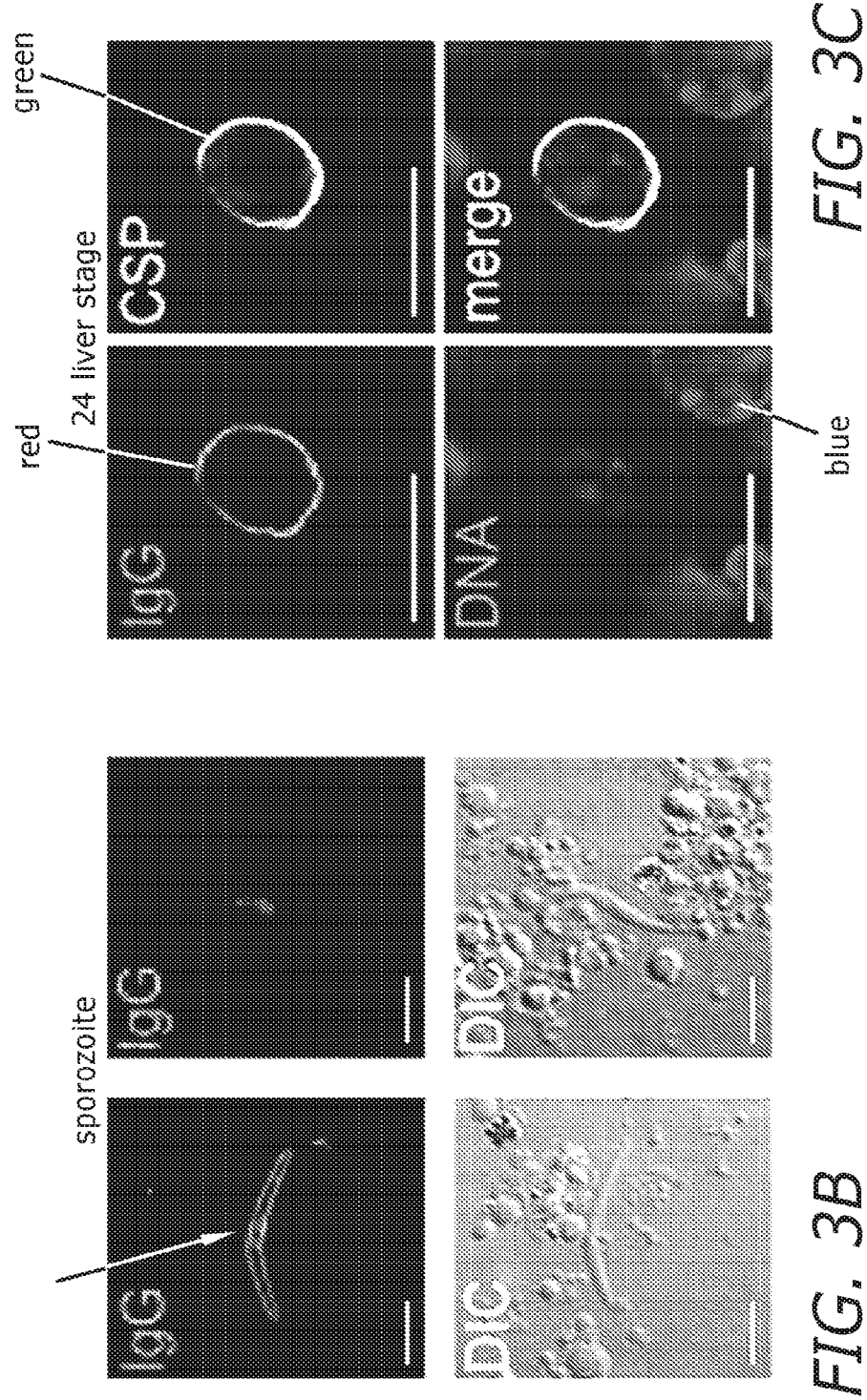

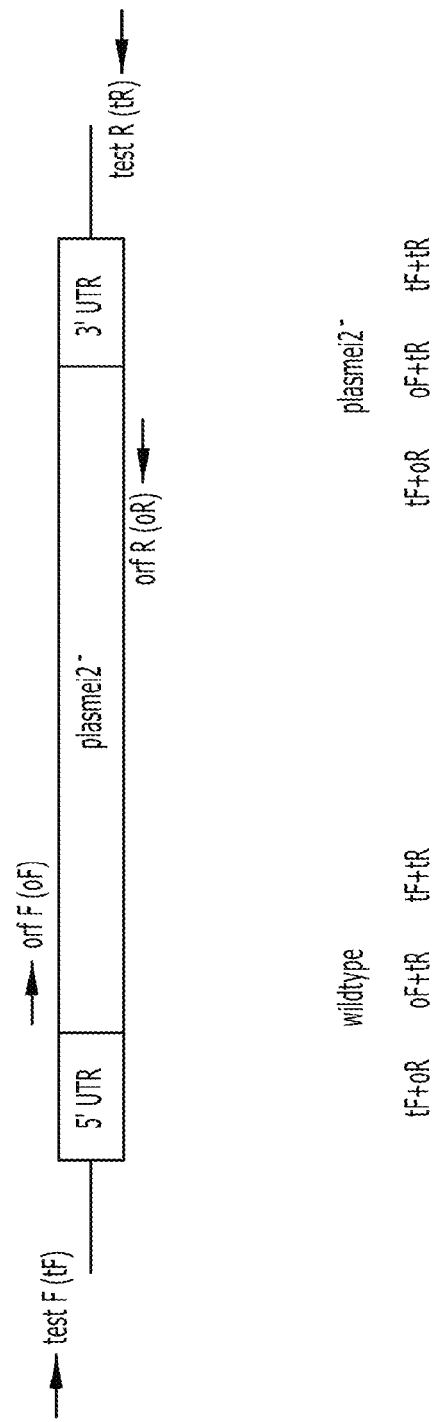
FIG. 7A
FIG. 7B
FIG. 7C

SEQUENCE LISTING

<160> NUMBER OF SEQ ID NOS: 23

<210> SEQ ID NO 1
<211> LENGTH: 1446
<212> TYPE: DNA
<213> ORGANISM: Plasmodium yoelii

<400> SEQUENCE: 1

| | |
|---|---|
| atgaatatga atttgaaaaa tataaactta gaagacgaaa aaataaaataa aagagtgagt | 60 |
| aataaaagaa tagtgcatat aaaaaaataca tatatatctc catatgttct ttataataaa | 120 |
| aaggggaata gtaataatca attggataaa ttaaataaaa tatttactag tgaaaataat | 180 |
| tgtagatttt caaaagaata ttataattat gttaaagatg gtgatatatg taatagtgga | 240 |
| gaaaaatatc ctgaatgttg ttccccaaat gttaagcaaa acaatagccc aaattatgac | 300 |
| caatgtaata atgaaaaaaa aatattaaaa tatggcttgt tgaatgaaca aaatatgaaa | 360 |
| tttttaaaaa aaaaaaaaga agaagatttt gaattaaata caatatctac tatgatacat | 420 |
| atttattctg attatgaaag tgataaagac aatgaaacga taacaaatga atataatgat | 480 |
| ttaatagatt gtataaaaaa aataaatatt tctaataata aatgtgttat taataatgat | 540 |
| aaaaaaatag aggatacttt attaagtcct tatgaacagt atagaaaatg tagttatcag | 600 |
| acaattgggc ataagaaaa ttatagtaac aaaaataatg aaaaaaatag tgacaaaaat | 660 |
| aatgaaaaaa atagtgacaa aaataatgaa aaaaatagtg acaacaatag cgataataat | 720 |
| aatgataaca atagcgacaa taataataac agaaatagcg ataataataa tagtgatgat | 780 |
| aatggagaaa atgtgtgca aagattaaat aattttatat ctattccttc agtatcaaac | 840 |
| aaaagttgca tagaacatgt acatgttcag aatgatcata tggatactgt gtattatgat | 900 |
| aattttattt gtaataaaga aaatcgtgat aataatgaaa atgatactat atataaatgt | 960 |
| gaagaatcta taccacttgg aacaatatta aatattcata atttagatag taataataat | 1020 |
| aatggtctaa caacagttat gttaagaaat ataccaaata aatatacaca aaatatgtta | 1080 |
| atggatgtta tgaatgagca ttttaaaggt ttatatgatt ttttttattt accaattgat | 1140 |
| tttcgtaaca aatgtaatgt tggttatgca tttattaatt ttatacatcc tcattatgct | 1200 |
| gaactattta ttaaattttt taataattat aaattaaatg catttaaaag taataaaata | 1260 |
| tgcactgtta catggggaag ggtacaagga ttaaaagcta atattgaaca ttacagaaat | 1320 |
| tctgcaatta tgactatatc tgtgcctcaa tataagccta tactttttca aaatggaata | 1380 |
| tctgtttcat ggcctgaatc ggatggtccc ttaccagcta taaaacttcg atcacataaa | 1440 |
| tattag | 1446 |

<210> SEQ ID NO 2
<211> LENGTH: 989
<212> TYPE: DNA
<213> ORGANISM: Plasmodium yoelii

<400> SEQUENCE: 2

```
ctacctgtaa tggaaatatc gacataaaga gaggaagaaa agatatgaga tatatagaaa      60
gattttattt ataatttttt ttttataaac attataaatt taaactggac atattttcac     120
caattattta atcacatatg tcataacacc atactataga aaatatatgt aatacatatt     180
tcgtataaat ttattaaaat tttattatta aaaatgtttt tttatttgtt gtgaatttat     240
ataatacaaa aatggggtat tccccatatt ctttttgttt ttattcattt ttttttgtt      300
tattatattt gctattttaa taaatacctc tttctatata tgcatatgat cgtgtgtaca     360
```

| | |
|---|---:|
| catgcatata tttggtatgt atattcatgt gccttttttg aagagcattt ttaatattga | 420 |
| ctttagtttt attattgttg taactattat acataacaaa taaaaaaaca tttaatttaa | 480 |
| gaatatataa ttcataaaaa aaattttgtt catatattca tatttggttg tttttttttt | 540 |
| ttttttccaa tagtatggta tttttcatta tacaacttaa ctacattttc tattctgtta | 600 |
| tattacatta ctctcattaa tagtgtaaca ttaacaacgt aaaattctga atacatggtt | 660 |
| tttcttctaa aaaggtaaat atagaatatg tatgctttat atatatttta atgtcaaaaa | 720 |
| aaaataaaaa taatgctata ttttaatat atttttttaat cattttatac gttttatttt | 780 |
| aataattctg tgatataatt tggctacatt taattacctt gccggtcaga aaaaaaaaca | 840 |
| taaaaatatg catgtacata aaaaatataa tcattacaca caaaaaatat atatatacat | 900 |
| acatataaag agaaaataag acttaaaata attctgacgt atgaatatag aaatagaaaa | 960 |
| gttgtaaata taaataagga cggacaaaa | 989 |

<210> SEQ ID NO 3
<211> LENGTH: 985
<212> TYPE: DNA
<213> ORGANISM: Plasmodium yoelii

<400> SEQUENCE: 3

| | |
|---|---:|
| tattgtttat aaaattatag aatttttacaa ctatgctaat ttattttata tacatataca | 60 |
| tatacataga aaaattatat tattatgttt gacttcccaa aaaaaaaaca cattaatatt | 120 |
| tcatattatc ttatttgcct gatcatatat atatacactc atttataata ttttagtttt | 180 |
| aaacgtttat tccatatatc taaaattatt actattgcca atgcgaaaac aggctatatg | 240 |
| tttcccttt attacatgtt tgaatttgtg tattattatt gttattcaca taataataaa | 300 |
| tgtgaaatga tgacccgagt tgtgaaggtg atatcctata ttatgtatgt tcatatgtat | 360 |
| gcgtgttcat atgtatgcgt gttcatatgt atgcgtgttc atatgtatgc gtgttcatat | 420 |
| gtatgcgtgt tcatatgtat gtgtgttcat gtatatgctt gttcatatgt atgtgtgtgt | 480 |
| gtgaatgacg agcggtattt atattacagg tacataaatt tgcacacata ttgataatta | 540 |
| tattttcccct gtacatttta tttccctctt tttaatatat tactttatat aacatgtatg | 600 |
| tgagtgctta taaataaaat tgtgtaaaat tcgttggtaa cttattatta caactgttgt | 660 |
| tattttgctt atttattact attttatttt ttagccttaa actggtgcct ctttgatatg | 720 |
| ttctcttgta tatgtccacg agttattttg gaaatcattt ttgtgagcat atataatgca | 780 |
| actacataaa tatgtgtgca tgatttaaca aactatttta tatttacttc cttcacaaca | 840 |
| tgtttaacat attttttaaa tacatttta tatataaata ttgatacata cacaacaaaa | 900 |
| tacaaaaaat actacattag tagctaatta taaattagtg atatttaata gatcgagttg | 960 |
| tatatataat gcttacattt gttaa | 985 |

<210> SEQ ID NO 4
<211> LENGTH: 20
<212> TYPE: DNA
<213> ORGANISM: Plasmodium yoelii

<400> SEQUENCE: 4

| | |
|---|---:|
| ggtaagggac catccgattc | 20 |

<210> SEQ ID NO 5
<211> LENGTH: 9927
<212> TYPE: DNA

<213> ORGANISM: Plasmodium yoelii

<400> SEQUENCE: 5

```
atgaaagatc atataaaaaa tgtatgcttt cggaaaactc tactcatttc actactactt 60
attatattaa aatacacaaa atatgattat ttagaaaaag aaaatggtgg aaaacaaaaa 120
tacaacagca atatatcgtc gccaagttta ctaagaacat attttggtgt atatgtcaat 180
agaaaaaata aggatgtaaa ggcattgaag aaattgttaa aaaatgttac gatttctaat 240
aattaccttt gcatggtgaa aaaggtggac ataaatgttt acaataaaat atgtggtaat 300
aagataaata aaattatatt gaacaacgaa agaaaatatg agaaaaatga tttaaaaaaa 360
aagtgcatta ctactgaatc ttcatcgtgc acatttgatg aagaaaaaaa aaggaaaaaa 420
ttattcacag attatgaaaa aataaattta tataaaaata gtaacccccct tgaggatatt 480
gacacaaatg gaaatacaat taaaggcttt ctttttgaat tatttgatat aattgaaaaa 540
attaagaaaa ttgtaataga tgcatctaac aaaattattt ccatgtgtct atttaataat 600
gataattaca aagaaaactt attcgacata aaaaataata aggattataa taaattgcat 660
aattataatt cttataaata ttatgaaaat ccaaatataa atacatacaa cattaataaa 720
gagttgtatg tatataatga ggaatatgct cataaatatt tatattcttt tatagacatt 780
tcacctgata atttaaatgt tgatttttat aaaaaagaag ttcaaggagg agatagaaat 840
atagtgcccg aaatttttaa aaataaaaat gtgtataatt tatctaagga taaaaagtat 900
gatatccatg ataagatgaa tgatggaaat aaatcgaatt gtggggtttc aagtgacaaa 960
gccgaaaaat atatatttga cactgaaaca aatagaagcg taaaacttaa aaaggaacaa 1020
tttttggaaa aaagtgaaaa ctggaatgaa agcaaaataa accaatcaaa caaactgcat 1080
aaaaaaaata acgaagtgat atatagatcg ataggaagaa ttttggcaga accaatatat 1140
gaaaatttag ttttaaatac agatagaaat aaagaaaaag aaagagaacg agaaatagaa 1200
aggaaacaag aaagagaatg ggaaaaggaa agagaaaaag atagaaatcc aaatacaaat 1260
aaaaataaac ctaatccgtt ggaagaaaaa cttttgctga ttattaaaga acagaaagga 1320
gatcctaaaa gtgaaaattc cgaacaaaat caaggaatta ctgtattaga atttagtcgt 1380
acaccgtcaa aaaaaaaaaa aagatcatgc acaattttag ctgaaaatga atcagaaact 1440
tcgggcgaag ataaagaaaa ggataaaaaa caagataaag aatctaatac ttctgacaat 1500
aacaatggtg atagtccagc ctctccagcc ccaaatgatt caaattatga tagtccagct 1560
tcgccagctc caaatgatgt accagaaggt aacattcaaa gaccttctag attaatcgca 1620
gaaaaggaat ctgaaaataa gagtgaagat aaaaaacaag ataatgaatc taatacttct 1680
gataataaca atggtgatag tccagtttct ccatctccaa atgatgtacc agaaggtaac 1740
attaaaagac cttctagatt aattgcagaa aaagaatctg aaaacaatag taaaaataag 1800
agtgaagaca aaaagcaaaa taaagaaagt aatacttctg ataataaaaa tgaagactca 1860
aattatgata atcccgcttc tccagcccca aatgattcaa attatgatag tccagcttct 1920
ccagccccaa atgatgtacc ggaaggcaac attcaaagac cttctagact aattgcagaa 1980
aaagaatctg aaaataatag tgaaaataag agtgaagata aaaaacaaga taaagaaact 2040
aatacttctg ataataacaa tggtgataat tcatcttctc cagtcccaaa tgatgtacca 2100
gaaggtaaca ttcaaagacc ttctagatta atcgcggaaa aagaatctga aaataatagt 2160
aaaaataaga gtgaagacaa aaagcaaaat aaagaaagta atacttctga taataaaaat 2220
gaagactcaa attatgataa tcccgcttct ccagccccaa atgattcaaa ttatgatagt 2280
```

```
ccagcttctc cagccccaaa tgatgtaccg gaaggcaaca ttcaaagacc ttctagacta    2340
attgcagaaa aagaatctga aaataatagt gaaaataaga gtgaagataa aaacaagat    2400 aaagaaacta atacttctga taataacaat ggtgataatc cagcctctcc agccccaaat    2460
gactcaaatt atgatagtcc agcttctcca tctccaaatg atgtaccaga aggtaacatt    2520
aaaagacctt ctagattaat tgcagaaaaa gaatctgaaa acaatagtga aataagagt    2580 gaagataaag aacaaaataa aaaacaagat aaagaaacta atacttctga taataacaat    2640
ggtgataatc cagcctctcc agccccaaat gatgtaccag aaggtaacat tcaaagacct    2700
tctagactaa ttgcagaaaa agaatctgaa aataatagtg aaaataagag tgaaaataaa    2760
gaaactaata cttctgataa taaaaatgga gactcaaatt atgataaccc cgcttcgcca    2820
gccccaaatg attcaaatta tgataatcca gcttctccag ccccaaatga tgtaccagaa    2880
ggtaacattc aaagacctic tagattaatc gcggaaaaag aatctgaaaa taatagtaaa    2940
aataagagtg aagacaaaaa gcaaataaaa gaaagtaata cttctaataa taacaatgaa    3000
gactcaaatt atgataaccc cgcttcgcca gccccaaatg attcaaatta tgataatcca    3060
gcttctccag ccccaaatga ttcaaattat gatagtccag cttctccagc cccaaatgat    3120
gtaccagaag gtaacattaa aagaccttct agattaatcg cggaaaaaga atctgaaaat    3180
aatagtaaaa ataagagtga agacaaaaag caaataaaag aaactaatac ttctgataat    3240
aacaatggtg actcaaatta tgataatcca tcttctccag ccccaaatga tataccggaa    3300
ggcaacatta aaaggccttc tagactaatc gcagaaaagg aatctgaaaa taagagtgaa    3360
agcaatagtg aaaataagag tgaagataaa aaacaagata agaatctaa tacttctgac    3420 aataataatg gtgatagacc agcttctcca gccccaaatg attcaaatta tgatagtcca    3480
gcttctccag ccccaaatga ttcaaattat gatagtccag cttctccagc cccaaatgat    3540
gtaccagaag gtaacattaa aaggccttct agactaattg cagaaaatga atctgaaaat    3600
aaagaaaatg aaaaaaaaa aaaaataaaa gtatataata cttctggtaa taataatggt    3660
gatagtccag cttctccagc cccaaatgat gtaccagaag gtaatattaa aagaccttct    3720
agactaatcg cagaaaaaga atctgaaaat aatagtgaaa ataagagtga agataaaaaa    3780
caagataaag aaactaatac ttctgataat aacaatggtg atagtccagc ttctccagcc    3840
ccaaatgatg taccagaagg taacattcaa aggccttcta gactaatcgc agaaaaggaa    3900
tctgaaaata agagtgaaag caatagtgaa aataagagtg aagataaaaa acaagataaa    3960
gaaactaata cttctgataa taacaatggt gataatccg cttctccagc tccgaaggat    4020
gtaccagaag ataaacctaa aaggcctact agattattcg cagaaaaaga atctgaaaac    4080
aatagtgaaa taagaatga agataaaaaa caagataaag aaactaatac ttctgataat    4140
aaaaatgacg actcaaatta tgaaaatcca gcttctccag ctccgaagga tgtaccagaa    4200
gataaaccta aaaggcctac tagattattc gcagaaaaag aatctgaaaa caatagtgaa    4260
aataaagaac aaaataaaga atctaatact tctgataaca acaatggtga taactccgct    4320
tcttcagtct caattgatat accagaaggt aacattaaaa tcccttctat attaatttca    4380
gaaagtgaat ctgaaaataa gagtaaaact aacggtgaag ataagaaca aaataagaa    4440 tctaatactt ctgataacaa tggtgataac tccgcttctt cagtctcaat tgatataccag    4500 gaaggtaaca ttcaaagacc ttctagatta attgcagaaa aagaatctga aaataatagt    4560
gaacataata gtaaaaataa gaatgaagat aaaaaacaag ataaagaaac caatacttct    4620
```

```
aataataaaa ctgatgataa tccagcttct ccagctccaa atgatgtacc agaagataaa    4680
cctaaaaggc ctactagatt attcgcagaa aaggaatctg aaaacaataa tgaaaataag    4740
aatgaagata aaaacaaaa taaagaatct aatacttctg ataataaaaa tgaagactca    4800
aattatgata accccgcttc accagcccca aatgattcaa attatgataa tccagcttct    4860
ccagctccaa atgatgtacc agaaggtaac attaaaagac cttctagatt aatcgcagaa    4920
aaagaatctg aaaataatag tgaaaataag aatgaatata aagaacaaaa taagaatat    4980 aatacttctg ataacaacag tggtgatatt cctgaatctc agtcccaaa ttatgtacca    5040 gaaggtaaat ttaaaagat ttctagacta atcgcgaaaa aagaatctga aaataatcgt    5100
gaaaataaga gtgaagataa aaacaagat aaagaaacca atacttctga taataaaaat    5160
gatgatagac cagctactcc agttccaaat gatgtaccag aaggtaacat taaaaggcct    5220
tctagactaa tcgcggaaaa agaaactgaa aataatggtg aaaataagag tgaagataaa    5280
aaacaagata agaaactaa tacttctgac aataaccatg atgataagacc agctactcca    5340 gccccaaatg atgtaccaga agctaacatt aaaaggcctt ctagattaat tgcagaaaaa    5400
gaatctgaaa ataatagtga aaataagagt gaaaataaag aaactaatac ttctgataat    5460
aaaaatggag actcaaatta tgataacccc gcttcgccag ccccaaatga tgattcaaat    5520
tatgataatc cagcttctcc agccccaaat gatgtaccag aaggtaacat taaaagacct    5580
tctagattaa tcgcagaaaa ggaatctgaa ataatagtg aaaacaatag tgaaaataaa    5640
gaatctaata cttctgataa caacaatggt gatgactccg cttcttcagt ctcaattgat    5700
ataccagaag gtaacattaa atggtattct agaccaaccg cagaaaaaaa atctgaaaat    5760
aatagtgaaa acaatagtaa aaataaagaa tctaatactt ctgataacaa caatggtgat    5820
gactccgctt cttcagtctc agttgatata ccagaaggta acattaaaag accttctaga    5880
ttaatcgcgg aaaagaatc tgaaaataat agtgaaaata aaaatgatga taaaaaacaa    5940 gataagaaa ctaatacttc tgataataaa atgaagact caaattatga taaccccgct    6000
tcaccagccc caaatgattc aaattatgat aatccagctt ctccagctcc aaatgatata    6060
ccagaaggta acattaaaag gccttctaga ttaattgcag aaaagaata tgaaaataat    6120 agtgaaaata agaatgaata taagaacaa aataagaat ataatacttc tgataacaac    6180
agtggtgata ttcctgaatc tccagtccca aattatgtac cagaaggtaa atttaaaagg    6240
ttttctagac taatcgcgga aaaagaatct gaaaataata gtgaaaataa aaatgatgat    6300
aaaaaacaag ataagaaac taatacttct gataacaaca atgaagtctc aaattatgat    6360
aatccagctt ctccagcccc aaatgattca aattatgata tcccgcttc tccagtctca    6420 gttgatatac cagaaggtaa cattaaaagg ccttctagac taattgcaga aaagaatct    6480 gaaaataata ataaaaataa gaatgaagat aaaaacatg ataagaaac taatacttct    6540 gataataaaa atgaagactc aaattatgat accccgcttc accagcccc aaatgattca    6600 aattatgata tcccgcttc tccagtctca gttgatatac cagaaggtaa cattaaaagg    6660
ccttctagac taattgcaga aaagaatct gaaaataaga tgaagataa aaacaagat    6720 aaaaaacaag ataatgaaac taataattct gacaataacc atgatgatag accagctact    6780
ccagccccaa acgatgtacc agaagataaa cctaaaaggc ctactagatt attcgcagaa    6840
aaggaatctg aaaataatag tgaaaataag aatgaagata aaaacaaaa taagaatct    6900 aatacttctg acaataacca tgatgataga ccagctactc cagccccaaa cgatgtacca    6960
gaagataaac ctaaaaggcc tactagatta ttcgcagaaa aggaatctga aaataatagt    7020
```

```
gaaaataaga atgaagataa aaaacaaaat aaagaatcta atacttctga taataaaaat    7080
gaagactcaa attatgataa ccccgcttct ccagccccaa atgatgattc aaattatgat    7140
aatcccgctt ctccagctcc aaatgatgta ccagaaggta aatttaaaag gctttctaga    7200
ctaatcgcag aaaagaatt tgaaaataag agtgaaaaac atatttccgg aaaaaataaa    7260
gcaaataaaa gtacgtttgt agaaaatgga caaaaatgga acttggatga agaaaggaaa    7320
agcatgttcg aaaagataaa aaagaaaaaa caaaaataca aaaaaaaata ttatgcttat    7380
gatatgattg aaaaaatgga atatttgagt tcgctatcag atgatgaata ttttacgaat    7440
gatggtgccc ctaatcatgc acaaactagt agtgttctag aaaatatttt gaaacatcct    7500
aatacttata ataaatattt agatattaat ttatttttcg atgaaaaacc atatcaatat    7560
agaaaaggta attattattt tataaatcca tttccatata gtattataaa gatgaaaaaa    7620
aatgaaggat tatctaattc agaaaaaata aaatatgatg gtgtctattg ttattctctc    7680
tcctttaata attattcttc attaacatat acaattgaaa actcattcag aaatgtaaaa    7740
ccaatagaag aaataatacc aggcacatta acaggtttta aaagtgatga cggatatcaa    7800
aaaatgctta ctccaatgtt tgttgaacag gatatgttct tacattgtgc atttaagaat    7860
gaatatgatg aaatagaaaa taaaatagca tcatttcctg ttaaaatatt tttaaaaaaa    7920
aatttaaaca aacaaaagg gtgttctttt caaataaata aaaatggttc gatatataaa    7980
gaatatgcag aaagggaatc attttttaagt aaaaaagtta tattgaatga tgaaagtacc    8040
agtaacgaat gtgatatcac agctacaaat gaaattattg gttttcaatg tggaccccca    8100
tacaaatatt ataccaacga cagtaatacg agttatattg ataagatttt ttttaatact    8160
gtgaataatg aagatataaa aattggtgaa tattttaaag ttgaacctgc acattgtttt    8220
gaagaagtta atgcaaatga acatattgaa gatattgccc caggtagttt ccctttcccg    8280
aattttgaaa tgataaatgg aggtttaaaa tcacatcata caaggtatat aaagttaaaa    8340
ataagagatc caaatgcaat tatatcatgt tattgcaact attataataa tgggaaaata    8400
atttattcag gtataatgac tataaatggt aaaaaaaaat ataatgatca atcatattcg    8460
gattatccac ctcaagacat taataaaaca agcgataatc caaaaggaac tggtcacaaa    8520
acaattaatt caaataaaaa aagtaaaatt gataatacgg aaaattatga taatgactat    8580
aaatattttt ttaatttctt gccatattat aatccatatc tcatgcaata taaaaagcag    8640
cctgaatacg ttgtgaaaaa tgatttcata tatgatagta agtatagcga cacaaataat    8700
gatgaatttt taaaaaaaat taaaaataat ttgtccgact taaaactcac tgataacaat    8760
gagtatattc atgatatgga tgataattta agatataaat acgataatag agattctaac    8820
gtgtacccaa tcagtgaata tgatctgaaa atcattttg atagcgacgt gttgtcagat    8880
tcttatggac acacgtttaa tgatgattat ataagtccac atagtaactc atattatgaa    8940
gaaaatacgt ataactcaga tgacattttc tctaattatg atgacgttaa tattgaagct    9000
gaatatgaag aatttgaacc attgcaaaat aatgtaactt ttcaagataa taaatcctat    9060
gaagataaat ctcaatctat tatagtaatc aataaatcaa aaaatgttaa tctttatatt    9120
cccaaaaata aaataaaaaa taatcggaaa tatacaaaaa ataatgaaga tatagaagat    9180
aataaaaaga aagatgcgct cctttaaatat ttattattaa catacgaaga aacaccagat    9240
aaaaatgaaa aaatgaataa aaaattaaaa ttatttaaag aatatttccc gtcttcacca    9300
aaccataata tatttgtaga agaaaaagaa aatgataata catcaaataa aataaaaagt    9360
```

| | |
|---|---|
| atatttgata atcaagaaaa atcaatagaa tcattaagtg gggaacaaat caatggtgaa | 9420 |
| atagaagtat ctgaaaatga ttctacttta gatcataata aatcttataa ttacgataat | 9480 |
| acaaatagca acaatcatga aaataataat gctggtgtga ataatgctga tgtgaataat | 9540 |
| gatggtgtga ataatgatgg tgtgaataat gctggtgtga ataatgctgg tgagaataat | 9600 |
| gctggtgtga ataatgctgg tgagaataat gctggtgtga ataatgctga tgataataat | 9660 |
| gctgatgata atattgatga cgatacaaca aattttatta tggataaaat tttacatgat | 9720 |
| ttgtttggac ataatgaata cgatggcaat aaagaagaaa atccaaaaaa caagaaaata | 9780 |
| tatcaaacta aaattaatac aatagaaaat gaagaagacg atgaagaaga ggaagaggaa | 9840 |
| gaagaagatt taattgaaaa ggatggagaa ttagagaaag aaggcattgt tccaagaaga | 9900 |
| aaacaaaaaa gagttaccaa aatttaa | 9927 |

<210> SEQ ID NO 6
<211> LENGTH: 1006
<212> TYPE: DNA
<213> ORGANISM: Plasmodium yoelii

<400> SEQUENCE: 6

| | |
|---|---|
| ggtacatcga cattcaccac aaaatatttc gtagagttgc attatcatca aaagggtata | 60 |
| aaattataaa atataacata aaatataaca taatggtgaa actaaaaata acgaaattca | 120 |
| agttggttga ataaaataaa aacacaacat aaaagatcaa ggtattattt ttttttaaat | 180 |
| attctttatg aaaaacgatt agaacaattt aaaataatgt atattatgct tgtacaatat | 240 |
| agttaaaata aagcgaataa cgatacgatt attcaatatg cagattaata atatatatgc | 300 |
| atgtaaatgt gtatatattt cttcattgtc aaattgctta ggcatatgta gcatatatga | 360 |
| tttttgacga ttcttaaaa atatacaact gtaattccta ataaattaat gcagttgtaa | 420 |
| tcgaaaaaaa ggcatgtgct cccgtatcga tttaaccatt taggtattga tctatgatcg | 480 |
| atctacatgt gaagaaaatg tgcattttta aaaacagttt cataatggtt tatgaatttt | 540 |
| ttagatcata tattgtttaa acaaaaaata aaacaaatac ctattgtttg atattcgata | 600 |
| aagtgtgcaa acaaatttgc atgtatgtat tctattatcg ttggtttttt ttacaccacc | 660 |
| tttttttttt atttataatg ttttttcacca caaagcaact atatatataa aacacactaa | 720 |
| aaatatataa ttaaattaaa aaatataata agaaaataa aaagcatatg tattatacat | 780 |
| acatgtatat tctcctgaat atgtatgttt tcagttcaga ttaagaacaa aaaaatacag | 840 |
| ataattaagc atttatttgt tacgtttata catgtcaata ccaaaaatat atatgtgcct | 900 |
| acacatgtta catataagta gatacatata aatatatcgg agtaatattt ttcttcttta | 960 |
| atttttcact tttattataa tcattttact tttttacaca taaaaa | 1006 |

<210> SEQ ID NO 7
<211> LENGTH: 963
<212> TYPE: DNA
<213> ORGANISM: Plasmodium yoelii

<400> SEQUENCE: 7

| | |
|---|---|
| agaaaaacct aaaagaggta atacccaaaa atatgcatat aagaaaaagg gcaaaccata | 60 |
| ttggaaatac atgatataag gaatgaaatt caaagtgaaa aagaataatg tactattaat | 120 |
| ttggaagtgt tgaacgtgat aacaaaagca aacaaaagga gttaaatcaa aagaaaataa | 180 |
| gacggaaagt cagaaagaag taataattca aataagcata ataatataaa atacctaaag | 240 |
| tttaactata taaataagta ttcgaattaa atatcttata ataatatata tttgtttttc | 300 |

-continued

```
tatactatta taaataaaaa tgtgagcata tatgtctttg tgtaattttta tattcatatt      360 caaaccattt atgattattt tactaaggtt gtcctaattt aaattataat tagaaaaaaa      420
ctagtatata tttgaataga atttttaatta catattataa aaaaaacata attttttatt      480
ataaaatact tcatttcatt ttattaacct acaagacatt atttaacatt aacttcctca      540
aaaaatgtaa aaaataaatt aaaaaaaatt tcttattcta ttttatttat ttttatgaga      600
tttgtgcaag aacaaagtat tttattaaaa ttttaaaaaa aataaataca taaaattcaa      660
aaatttcata aatgttttta aaagagaata aaaataagaa gcataaatca tataatattt      720
attttggctg agtaatagac tagattattt ggtatctatg tataatttga tgatataaat      780
attgtaaaag gcaataattt aatttctcac attttaatga tgactaatta tattgactaa      840
ttcatatgta ttatgtttgg ttgcttagac tattgtgata tcaagtcttt ccattttcac      900
taattatttg acattttta tttcatctaa cgatattttg tagttttaat ttgaagttat      960
ttc                                                                    963

<210> SEQ ID NO 8
<211> LENGTH: 20
<212> TYPE: DNA
<213> ORGANISM: Plasmodium yoelii

<400> SEQUENCE: 8
catattgaag atattgcccc                                                   20

<210> SEQ ID NO 9
<211> LENGTH: 1284
<212> TYPE: DNA
<213> ORGANISM: Plasmodium falciparum

<400> SEQUENCE: 9
atgcataaga tagatgaaaa gataaatatg aataatgtaa aaggcactag aattattcat       60
gtaaaaaata catatatatc tccatacata ctacacaata taaacaataa tgaaggccca      120
ttaaaaaata tagacaaaat attaaaagaa gaaaaagata atataaattt aaagatcaat      180
aatgttaata ataaggaaac taataatgat aagcacacat taaaatattc aacattatgt      240
aatgatctaa atataatgca tacacaaaat aaagaagaag aaattgaatt aaatacaatt      300
tcaacggtta tacacatgaa ttctgatgaa gatagtgata agataatgat accataata      360 aatgaaaaca acgatttgtt aattgataat ataagaaat atcatgccgt taaagataat       420
cataataata ttatttataa tgataaatat aatacaatta ataataattc agtcattaat      480
gatgtatgta attctattca ttttaataat aattcatata taactaactt taatttaaat      540
cataattttt ctgtgtgtaa tcgtactttta aataacacct gcacaagtca ggtaaatttg      600
agaaataata tgaacagcaa taaaaaaact aatgataaca ataaaaatct gaacaatgaa      660
attaataaga aaatcaataa tgataatatt ataaacgaat tgataatat taataataag       720 aaaaataatt atattgattg ttccgtttac aaatgtgagg atgaaatacc ccttggtacc      780
atattaaata tccaagattt ggatatacat aatagaaata atatgaacaa ttgtaataat      840
aatattaata ataagagtaa gattcttaca acagttatgc ttagaaatat tccaaacaaa      900
tatacacaaa atatgttgat ggatgttatg aatgaacatt ttaaaggttt atatgatttt      960
ttttatttac caattgattt tagaaataaa tgtaatgttg atatgctttt tattaatttc     1020
atacatccat attatgctga attgttatc aaatttttta ataattataa actcaatgca     1080
```

| tttaaaagta caaaagtctg ttctgttact tggggaagag tacaaggatt aaaggcaaat | 1140 |
| attgagcatt atagaaattc agcgattatg accataccaa taccacaata taaacctata | 1200 |
| cttttttcaaa atggtataac tgtttcgtgg cctgaatcag atgggccttt accatccatc | 1260 |
| aaattaagat ctcaaaaatt ttaa | 1284 |

<210> SEQ ID NO 10
<211> LENGTH: 1011
<212> TYPE: DNA
<213> ORGANISM: Plasmodium falciparum

<400> SEQUENCE: 10

| catttataat aatacataca attttgaatt ataggatttt tttctttgat gtattatatg | 60 |
| tattaatatt attattttta taaaatgaat attttaatta ttatatttta atttcattta | 120 |
| aagtatttta aaattattat tataataaaa atattagatg catcttgtgc ttacatataa | 180 |
| catttgcatg tgtggaaata ttctctttcc ataaaaagat acaacttctc ttgttttgt | 240 |
| tttatttatt ttgattattg agaaataata taagaatatt taaccaatga attaaattaa | 300 |
| aaatggtatt cttttttaaaa atgaaaaaaa aaaaaaaaaa acgtcaatgt aagaacaaaa | 360 |
| aagtgacaaa ttcattggt atttttttata taatatattt tttttaattt atttatttat | 420 |
| tcctttatat atatatatat atatatatat atatatatac atacatacat atatatataa | 480 |
| tttatatata atttatatat attatattaa atgatatgtt tataagaaaa aataaaatta | 540 |
| tgtgaatatt ttaattgtta taattgatta taaattattt gtgtttttat tttgtataat | 600 |
| tgtatgctcc aacatttaat gtgtatgcta aatatcgatg gaatattatt aaatatataa | 660 |
| ttcttaaaaa ttgagatttt acatatttt ttttattccc gttttttaagc tgtttcataa | 720 |
| aaaaaaaaaa aattcataaa gatatgaaat ccatatttt ttaaatattt ggaaaaagga | 780 |
| atataacatg taattatata atatatatat atatatatat atatatataa tttggactaa | 840 |
| tcatattgat ataaaaaaat atttttataa taaaaaataa taaataaata aataatagag | 900 |
| gagagacata accaaaaagt gttgtaaata atacattaat atatatatat atatagatat | 960 |
| atatatattt tttttttttt tttttctcc ttttatcaaa atgcataaga t | 1011 |

<210> SEQ ID NO 11
<211> LENGTH: 859
<212> TYPE: DNA
<213> ORGANISM: Plasmodium falciparum

<400> SEQUENCE: 11

| ttaaattcaa agatgtatat agacacaaaa aaaaaaaaaa aataataaaa aaataaaaat | 60 |
| atatatatat atttatatat ttatgtatca ttgtttaaaa aaattaacaa attaaccttc | 120 |
| ttatgttttt acaatttaca tactgattat atatatatac gtgtataatt tactattcat | 180 |
| cttatcttat atattatctt ctttttattta tttatttatt tatttgtttt ttttttttt | 240 |
| tcttttcctt ttctcttttc ttttttccgca ttaaatataa tgtatcaaaa tgattatttt | 300 |
| aattatatga aaataaaata tatctgttaa aaataataat gtgtaaaaaa aataaaactt | 360 |
| atttatatac atttatatgt gataattata tattattatg tatatatatt aatttatttt | 420 |
| tatttttattg attaaaatat aatattaatg ttttatttg tatatgaata tatattgtca | 480 |
| atgcttttata tatatttaaa atatatgaag gaattttatt ttttatattc ttgtctatat | 540 |
| atatatatat atatatatat atatatgtat atatattttt tatttcttaa caaattaaat | 600 |
| ctagttttctt tattattata taacttatc aacatttaaa ataaataaaa taataatttg | 660 |

```
tgaatatata attatcaaat gtttaattgc ttttttatat cccttataaa aacatatttc    720
gaaaaatata catatatata tatatatata tatatatata tatatgtttg              780
aaccgttaag taataatat ggatagtaat attctaatac ttttatgaat tccctcgtaa    840
ttttaataat tgccacagc                                                 859
```

<210> SEQ ID NO 12
<211> LENGTH: 20
<212> TYPE: DNA
<213> ORGANISM: Plasmodium falciparum

<400> SEQUENCE: 12

```
aaataacacc tgcacaagtc                                                20
```

<210> SEQ ID NO 13
<211> LENGTH: 5895
<212> TYPE: DNA
<213> ORGANISM: Plasmodium falciparum

<400> SEQUENCE: 13

```
atggagaagg ttctattttt atcgtttatt ttcttttgtt ctgttgttat ctttatacga    60
tttatcggat atttcttttg taatcgttac atgacagaag aaccatataa taatattttt   120
gagataataa aacctgagaa tttatatagt tctttattat tattgtcaaa tgaaaaggaa   180
aatgattttc ctagttctac aaattgtaac ggatatatga aatgtatccc cttttataat   240
aatgtttctg aaagatggaa gagatataat tttatacaac tttatataat tagaagtgca   300
ttaaatatac atgtgatgag taaatataat atgttaaata aatataataa ggaaacgaac   360
agattattaa aaagaaataa taatgtagaa aatagaatta ataatatatc caatcattat   420
ttatgttcag gttttaaaaa agaaaaccgt ttattcttcc ttttgtttta taaaacaatt   480
aagatgatga agttatatat aaggaatttg tttatgaaat atattaaaat ttattataaa   540
acaaaacatt ttgagaagaa tatagaaact aataaaaaag tggtttatgt tgaaagggat   600 aatcttttg atattgaaag gaataatctt tttgatattt tatatatgtt aaaaagaata   660
gatagttatg taagaatat atattcaatt atttctaata atttcttgta tgttataaga   720
ataatatttt taccatttga aaaaatctat ttctctttaa aatcccttat aatgataaaa   780
aaaatgaaca tgtcttcttc ttattattat tattatgtaa atatgttttc tttgtataaa   840
aagaattaca caaaatatga agaaattttt attcatgagc aaagagtaat atatcctaat   900
gaatacttga aaaatgaaat gttggataaa tatagaaggg ttatacgaat tctctcggga   960
cagcatgata atccttttat agattctctt ttaataaacc ctgagaaaat tgaaaaagat  1020
gatttagatg taaagcagaa aaaaaaaaaa ataattgaag agctgaagaa aaaaaaggaa  1080
aatacaaaca caaatacaaa tacaagtaca aatacaagtg caaatacaaa tacaagtaca  1140
aacacaagtg caaacacaaa tacaagtaca aaagaatctc acatattaga tgaatcgaaa  1200
ctagaaacct tttacagaga cgaattagac aaaatgggaa aagaagaaat tgaaacatat  1260
ttcaaaggga atattgacaa aaaatcactt gatgaatttc ataaaatatt gctagaagag  1320
ttaaacaaaa tggacaaaga tgaattatat gaaatgtata gagaagagtt aaataggatt  1380
gaacaagaaa aaattagaaa tatgaataaa gaagaaataa ataaaactta caaggacgaa  1440
ataaataata tgaatagtga tcaagttgat aaaaatacata gagaagaatt agaaaaaatc  1500 gaaaagaaa aaataaacaa aatggataaa gatgaaatag ataaaatata tagagaagaa  1560
```

```
ttagacaaaa tggatcgaga tgcaatttat agtatgtata tagaagatat aagtaacaaa      1620
aatataaaag acttaattaa aaatgaaaag gaaacaaata aggataaaaa caaaaaaaaa      1680
gatatagata taaacaaaaa gaaaaaaaaa gatatagata tagatgtaga catagataaa      1740
gatatacata aagatcatgt agaagaatta tacggagaag taaaaaacaa acttagcaaa      1800
gaagaattag atagaatgga cagagacgca ttatatagag tatacctaga agaattagat      1860
agaatgaaca gagacgaatt atatagagta tacctagaag aattagaaaa aatagacaag      1920
gaagaaaaag aaaaaattca tagagaaaaa ttacacaaaa ttgaaaaaga gaaaataaat      1980
aaaatggata aagatcaaat agataaaata tatgaagaag aattaaacaa aatggatagt      2040
gatgaaattc aacatgtaag gagagcaata ttacaagata tacaaaaaga aaaaatacaa      2100
aatttagaac tagaagaaat cgatagactt tataaagaag aattagatag aatggataga      2160
gaagcaaggt atgaaatccc catgagaaat ttaagcagaa atgaaaaaga taatattata      2220
catagaaata ttaaaaatga atctaaccaa aaaaataaga aagaaaatgt aaatgtattt      2280
ataatacacg acaataatga tagtaataat aataataata ataataatag agatgtgaat      2340
aatttaaata ataagcacac aaataataat tataatgaaa atgtagaagt tgaattagtt      2400
gtacgaaatt tagacaagga taaggagcc aagatagaag atattataga ctattttaac      2460
aaagaaatta aaaagacaa aaatgttaat gtttccaata tagtgaattt tttaaattca      2520
aaagtaggaa aagataacac accaattcaa cataagaagg aaaatcaagt agatgttgtc      2580
aggaaaaata ttcagattat tcaagaggat aatataaaaa ataaaggcca aaggataac      2640 actgaaatgt tagataataa taaggaaata acaaatattg atataaaaaa tgttgatgat      2700
ataaaaaatg ttggagatat aaaaagtgtt ggagatataa aaagtgttga tgatataaac      2760
aatgttgatg gtataaaaaa tgttgatggt ataaaaaatg ttgatggtat aaaaaatgtt      2820
gatggtataa acaatgtggg agatataaac aatgctggag atacaaataa tgctggagat      2880
ataaacaatg tgggcgatat aaacaattct gtagatatat acaacgttga acatatagac      2940
gaagcggaga aaaaccaaa tcttgataat ccaaaaaagt ttgactggac acaggtattt      3000
aaagacaaag taacagaaaa gataaaaaat gaagaaaaat tcaacaactc aaaagaaaat      3060
atacaaaacg atataagaga taagaaatt cataaggatg atagaatcaa gggaattact      3120
tcacgagaaa agaatgctga agaaataaat aataatgaaa aaaagacaa gtttgtgtat      3180 gaatttata catccaataa gaaagaaaat atagataaag aagaagaaaa taatatagat      3240
gataaaaata taaaaataga aatagaacct aattatgaaa tcaacaacaa ttttgaagaa      3300
gaaaataaaa atgaaataaa tgttattata gataaggaag caaaaaataa tatggataaa      3360
gatgatagta ataataataa taatatacaa aagaataata ttataattaa ggataataca      3420
aatgtaagtg aagaggttca tattactgaa agtagtaaag aaatagcaga atttttaat      3480 aatataatta agaatagtaa tatcttagat atgtgttcaa aaatgaatgc ttccgattct      3540
gagaagggat ttatatgtat aaatggtaat aattatatta taaaccctgg tacgtatcat      3600
ataataaata taaaatatcc agattataat aatgttagaa aaaaatggta tgattcgatg      3660
gattgtatat ctataaataa caaggatgaa aataataata ataagaaca taattattac      3720 aataaaaatg atgatgattt atatttaaag aaatcggttg aagaatttat tccaggattt      3780
ttgagcaata ttaataaagt agatgattta gcgagaatat ttactccatc ctttattcaa      3840
aatgatattt ttttaaattg tatttacaaa tataggaatat attttgataa gaataataat      3900
atttattcct ttcctatgaa gatatttta agaaaaaatt caacgaaaat aaaaggttgt      3960
```

| | |
|---|---|
| tcttttcaaa ttgatgaaga ccctttgtta tataaagatt atagtgaaaa agaatcattt | 4020 |
| ctaagtaata aaattatttt aaataattca aacagaaata cggaatgtgt actacatgca | 4080 |
| tcaaatgaaa ttgtcggatt tcaatgtggt cctccatata atcttatga taatatacaa | 4140 |
| tatagacatc ttacaaacaa atcaaacgat atacaaaaaa atatatttgg tatatatagt | 4200 |
| aataataata gttcatattc tcatttattt aaaaatattt ttaataatga acataaatta | 4260 |
| tataacgtag gaggatattt tcaaacagaa ccaattaatt gttttgaatt tgtaaatgat | 4320 |
| aacataaatg tggaagatat attaccagga gcggttccat ttcctagatt tgatttgata | 4380 |
| catcatgatt tagatgttaa tcagaccaga tatattttat taaatgagac gaaccaagat | 4440 |
| aaaacaatct cttgtacttg taattatttt acagaaccta atattgttta tacaggtaaa | 4500 |
| attattatta aagttgaaga agagaaaata tataaaacca aaaaattaca aactgaattt | 4560 |
| aatgatatta taaataataa aaaggaaata tatcacgaaa aaaaaatgaa tcatataatt | 4620 |
| aaagaaaaga aagatgaaga cgaaaatgat atgtcattta taaaaaatta tgttaataat | 4680 |
| tataatgaaa attttaaaat aaatgatata aataattttt acaatagaaa taatcatccc | 4740 |
| aataataatt atcacaacga ttatcacaat aatcattcta gtaaaggaaa ccacacaaac | 4800 |
| aaaatacatg atacatttct taagaataaa tacaatatct cttttaataa tttaaaattt | 4860 |
| tataatatta aacatgaaaa taaaaataat caagacgtta ttaattatga atataatgtt | 4920 |
| gatgattatc atgaggtgca ggatggtcag gacgaatcat ttaaagaaga ggaagatttt | 4980 |
| attgatttta aagaaaatat aattaatgat aataccaacc ataacaatac cgatcttgat | 5040 |
| gatgataaat ataataaata tcataataat aataataata ataataataa ttcttctttc | 5100 |
| aagtcgatag aaagtaatct tgatcttcaa agaagcatat tacaatctgg ggacacacaa | 5160 |
| caagtagttg taattaataa atcgaaaaat gtaaatgtcc ttttccaga taaaaaaaaa | 5220 |
| aatcacacac acccaaatga agagaagaga acatttccta aatatatctc tttagtatat | 5280 |
| aaagaaaaaa ataaggacaa tgaaaaaata gacaagacct taacctttat taaggagttt | 5340 |
| taccctccat tgcttagagg aggtaaagac agcgatccgg aaaataaaca aactggtgtt | 5400 |
| gaaataaaca atggtgtgga aaaaaaaaat gacgtacaaa taaaaaatga tgtgaaaata | 5460 |
| aaaaatgatg tggaaataaa aaatgatgta gaaataaacg atgatgtcga aataaaaaat | 5520 |
| gatgtggaaa taaaaaatga tgtgaaaata aaaaatgatg tagaaataaa cgatgatgtc | 5580 |
| gaaataaacg atgatgttga aataaacaat ggtgtagaaa taaacgatgg agtagaaaat | 5640 |
| aaagataata tacatgaggg taataataat ttagaaaatg attctttaa tgaagatact | 5700 |
| attgaagaac cctttgaaaa tattttgat tttataaatg aagaacaag ttcaaatgaa | 5760 |
| aactcggaaa taattcttga ttcagcagat tctataaaaa gaaaattagg tcacaactt | 5820 |
| ttagacataa taagtgcagg gaaatttaaa ataagacata agaaaaaaa aacaaaaaat | 5880 |
| aaaaaaaaaa aataa | 5895 |

<210> SEQ ID NO 14
<211> LENGTH: 925
<212> TYPE: DNA
<213> ORGANISM: Plasmodium falciparum

<400> SEQUENCE: 14

| | |
|---|---|
| aagggaaaaa tgcgccactt aaatggtctt taaaaaaaa aaaaaaaaa aaattctaaa | 60 |
| taccttacat atatatatat atatatattt atttatttat ttatttatat atttatatat | 120 |

| | |
|---|---|
| ttatatgtga aaaatattaa aaaaaaaata aagaaccaca ttgttttaat ataattattt | 180 |
| tatgtgtctt ttaatattat tgcagtggga ataaattaat aatatatata taatttttta | 240 |
| tttaaacata atgaaaagaa tacattataa gatggttaaa aaatgatcag ctttcatcat | 300 |
| cgacgttata tataaatgtg tcgattgttc taatggtgat attaaaatgt tcctatattt | 360 |
| tttttttttt ttttttcgcc taatatttat cacgttagat ccacacatat atacccaaaa | 420 |
| aaaaaaaaaa gaataagaaa aaaaatgtgt gaatatatcg aagcaaacat gttgataaat | 480 |
| atacatgtat gtatgttact catttgtctc tttttctttt ttgttacttt tcgagtgtct | 540 |
| tgtagagtgg gttgcatata tctacatagg aaagaaaaaa taaaaataaa taaataaata | 600 |
| aataaatata tatatatata tatatatata tatatatatt acgtatattt tttttttattt | 660 |
| tttattctta catgttttat aaatttgat agagccttat ttattgtaag gatataattt | 720 |
| aaaaaaataa aaatttcttt tttttatatt aatcaagcat tatatatatg aaatattgtt | 780 |
| cacatataat aataataata tatatatata tatgtgtgta tatatattta tttacatgtt | 840 |
| taataaattt tttatacact gaaaaaaaag tattatatat ctaaatatct acatatttat | 900 |
| ttatttctaa gtattggtat taaac | 925 |

<210> SEQ ID NO 15
<211> LENGTH: 850
<212> TYPE: DNA
<213> ORGANISM: Plasmodium falciparum

<400> SEQUENCE: 15

| | |
|---|---|
| caaccataac aataccgatc ttgatgatga taaatataat aaatatcata ataataataa | 60 |
| taataataat aataattctt ctttcaagtc gatagaaagt aatcttgatc ttcaaagaag | 120 |
| catattacaa tctggggaca cacaacaagt agttgtaatt aataaatcga aaaatgtaaa | 180 |
| tgtccttttt ccagataaaa aaaaaaatca cacacaccca aatgaagaga agagaacatt | 240 |
| tcctaaatat atctctttag tatataaaga aaaaaataag gacaatgaaa aaatagacaa | 300 |
| gaccttaacc tttattaagg agttttaccc tccattgctt agaggaggta aagacagcga | 360 |
| tccggaaaat aaacaaactg gtgttgaaat aaacaatggt gtggaaaaaa aaaatgacgt | 420 |
| acaaataaaa aatgatgtgg aaataaaaaa tgatgtggaa ataaaaaatg atgtagaaat | 480 |
| aaacgatgat gtcgaaataa aaaatgatgt ggaaataaaa aatgatgtgg aaataaaaaa | 540 |
| tgatgtagaa ataaacgatg atgtcgaaat aaacgatgat gttgaaataa acaatggtgt | 600 |
| agaaataaac gatggagtag aaaataaaga taatatacat gagggtaata ataatttaga | 660 |
| aaatgattct tttaatgaag atactattga agaacccttt gaaaatattt ttgattttat | 720 |
| aaatgaagaa acaagttcaa atgaaaactc ggaataatt cttgattcag cagattctat | 780 |
| aaaaagaaaa ttaggtcaca acttttaga cataataagt gcagggaaat ttaaaataag | 840 |
| acataaagaa | 850 |

<210> SEQ ID NO 16
<211> LENGTH: 20
<212> TYPE: DNA
<213> ORGANISM: Plasmodium falciparum

<400> SEQUENCE: 16

| | |
|---|---|
| gaatgcttcc gattctgaga | 20 |

<210> SEQ ID NO 17
<211> LENGTH: 24

```
<212> TYPE: DNA
<213> ORGANISM: Artificial sequence
<220> FEATURE:
<223> OTHER INFORMATION: Synthetic

<400> SEQUENCE: 17
tattcatatt gaagatattg cccc                                           24

<210> SEQ ID NO 18
<211> LENGTH: 24
<212> TYPE: DNA
<213> ORGANISM: Artificial sequence
<220> FEATURE:
<223> OTHER INFORMATION: Synthetic

<400> SEQUENCE: 18
aaacggggca atatcttcaa tatg                                           24

<210> SEQ ID NO 19
<211> LENGTH: 39
<212> TYPE: DNA
<213> ORGANISM: Artificial sequence
<220> FEATURE:
<223> OTHER INFORMATION: Synthetic

<400> SEQUENCE: 19
gaccatgatt acgccaagct tggtacatcg acattcacc                           39

<210> SEQ ID NO 20
<211> LENGTH: 59
<212> TYPE: DNA
<213> ORGANISM: Artificial sequence
<220> FEATURE:
<223> OTHER INFORMATION: Synthetic

<400> SEQUENCE: 20
cttttaggtt tttctgggcc cttttatgt gtaaaaagt aaaatgatta taataaaag       59

<210> SEQ ID NO 21
<211> LENGTH: 47
<212> TYPE: DNA
<213> ORGANISM: Artificial sequence
<220> FEATURE:
<223> OTHER INFORMATION: Synthetic

<400> SEQUENCE: 21 tttttacac ataaaaggg cccagaaaaa cctaaaagag gtaatac                    47

<210> SEQ ID NO 22
<211> LENGTH: 58
<212> TYPE: DNA
<213> ORGANISM: Artificial sequence
<220> FEATURE:
<223> OTHER INFORMATION: Synthetic

<400> SEQUENCE: 22
aaacttaagg aattaattca agcttggaaa taacttcaaa ttaaaactac aaaatatc      58

<210> SEQ ID NO 23
<211> LENGTH: 24
<212> TYPE: DNA
<213> ORGANISM: Artificial sequence
```

-continued

```
<220> FEATURE:
<223> OTHER INFORMATION: Synthetic

<400> SEQUENCE: 23
ttttttaacg atgtaacagt gttg                                          24
```

DOUBLY ATTENUATED LATE LIVER STAGE MALARIA PARASITES AND RELATED COMPOSITIONS AND METHODS

CROSS-REFERENCES TO RELATED APPLICATIONS

This application is a continuation of U.S. patent application Ser. No. 16/480,615, filed Jul. 24, 2019, now U.S. Pat. No. 10,905,753, issued on Feb. 2, 2021, which is a U.S. National Stage of International Application No. PCT/US2018/015096, filed Jan. 24, 2018, which claims the benefit of U.S. Provisional Application No. 62/450,258, filed Jan. 25, 2017, which is incorporated herein by reference in its entirety.

STATEMENT OF GOVERNMENT LICENSE RIGHTS

This invention was made with Government support under AI125706 awarded by the National Institutes of Health. The Government has certain rights in the invention.

FIELD OF THE INVENTION

The disclosure relates to genetically modified *Plasmodium* organisms and related compositions and methods. In one aspect, the disclosure relates to doubly attenuated malaria parasites that have had the functionality of the LISP2 and PlasMei2 genes interrupted and due to this attenuation are unable to complete liver stage development. The attenuated malaria parasites are useful for methods and compositions for stimulating the vertebrate host immune systems and thus behave as vaccines. In another aspect, the disclosure relates to genetic modifications to drive expression of blood and gametocyte antigens in genetically modified *Plasmodium* organisms to enhance to immunogenic protection conferred thereby.

STATEMENT REGARDING SEQUENCE LISTING

The sequence listing associated with this application is provided in text format in lieu of a paper copy and is hereby incorporated by reference into the specification. The name of the text file containing the sequence listing is 65267_ST25.txt. The text file is 37 KB; was created on Jan. 24, 2018; and is being submitted via EFS-Web with the filing of the specification.

BACKGROUND

Malaria has a tremendous impact on human health, killing hundreds of thousands annually and creating a major impediment for social and economic development of nations in malaria-endemic areas, particularly in sub-Saharan Africa. Parasites of the genus *Plasmodium*, the causative agents of malaria, are transmitted to the vertebrate host through the saliva of an infected *Anopheles* mosquito. After transmission, *Plasmodium* parasites, in the sporozoite stage, travel quickly through the blood stream to the liver. Sporozoites that infect hepatocytes grow and replicate within the infected hepatocyte, producing tens of thousands of blood stage-infectious merozoites. Merozoites infect red blood cells, where they undergo further development and replication after which they cause the rupture of the red blood cell, releasing a new wave of merozoites into the blood. Most of the new merozoites continue to repeat the replicative cycle through more red blood cells. This cycling of infection and rupturing of the red blood cells manifests in the potentially severe symptoms associated with malaria, such as fever, chills, weakness, malaise, and enlarged spleen. A minority of the cycling merozoites eventually develop into male or female gametocytes that remain in circulation within the body until being taken up in a blood meal by a new mosquito. Assuming the new mosquito is compatible (i.e., another *Anopheles* mosquito), the gametocytes proceed to develop into gametes and fuse to form a diploid zygote. Zygotes develop into motile ookinete forms, which penetrate the wall of the mosquito's midgut and form oocysts. The oocyst undergoes numerous rounds of division to eventually produce infective sporozoites that can be injected into the next vertebrate host, thus repeating the lifecycle.

The hepatic stage of *Plasmodium* infection is an attractive target for malaria prophylactic intervention as it is asymptomatic and precedes the symptomatic blood stage infection. Decades ago, it was found that irradiated *Plasmodium* sporozoites ("radiation attenuated sporozoites" or RAS) can confer sterile, protective immunity in both rodents and humans when used as an experimental. This was surprising, as a natural infection with malaria does not induce sterile protective immunity in endemic areas of the world. Unfortunately, complications producing consistent batches of RAS and variable immunogenicity of RAS preparations have made this a challenging approach to the development of a useful vaccine composition.

More recently, it has been demonstrated that sterile protective immunity can be achieved after vaccination with genetically attenuated malaria parasites (GAPs) in rodent malaria models. Initial GAPs were produced by deleting genes upregulated in infective sporozoites (UIS) as compared to oocyst sporozoites. Such deletions did not affect viability of the GAPs when in the sporozoite stage, but resulted in arrest early in the liver stage of development. These GAPs exhibited powerful immunogenic properties, but also sometimes exhibited incomplete attenuation, allowing for liver stage-to blood stage lifecycle progression (also called "breakthrough"), leading to an active infection.

Next generation GAPs have been developed in an attempt to provide a liver stage parasite that follows the growth, development, and replication within the liver, only to arrest just before progressing to the blood stage. Such "late liver stage-arresting" parasites are believed to be more powerful immunogens than the early liver stage-arresting parasites because they can present a larger and broader range of parasitic antigens to the immune system. This is due to their increased numbers, size, and advanced development within the host hepatocyte. Indeed, in the rodent malaria model, *Plasmodium yoelii*, late liver stage-arresting GAPs have been shown to provide superior protection from sporozoite challenge as compared to early liver stage-arresting GAPs or RAS. Moreover, these GAPs have also been shown to provide stage-transcending protection from a direct blood stage challenge, indicating the presence of antigens in the late liver stage GAPs that are also characteristic of the blood stage forms. However, identification of target genes for deletion in the human malaria, *P. falciparum*, which results in complete attenuation at the late liver-stage of development, has been a continuing challenge.

Despite the advances in the art of creating attenuated *Plasmodium* parasites useful for stimulating the vertebrate immune system against a later challenge, a need remains to identify specific genetic-based modifications that provide simultaneously complete attenuation (i.e., complete cessation of lifecycle development prior to the rounds of amplification in the blood) and permit healthy and prolonged development of liver stage parasites to provide more antigens for a more complete immunity against subsequent parasitic challenge. The present disclosure addresses these and related needs.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1A shows four groups of five outbred SW mice were IV challenged with 50,000 sporozoites. As a control, mice were challenged with the luciferase-expressing 1971cl1 parasite that behaves as wildtype. Liver stage burden was measured in vivo at 43 hours by assessing luciferase activity. There was no statistical difference in flux between the four lines as determined by an unpaired two-tailed t-test. The hashed line indicates background flux. FIG. 1B shows photomicrographs of the parasite parasitophorous vacuole membranes from parasites with the indicated genetic modifications. Livers from parasite-infected mice were harvested, perfused with PBS, and fixed in 4% paraformaldehyde at 43 hours after sporozoite infection. Sections (50 μm) were cut from fixed livers, and IFAs were performed using primary antibody to the parasite parasitophorous vacuole membrane (PVM) marker Hep17 to fluoresce in green (exemplary signal labeled as "Hep17"), the endoplasmic reticulum by BiP to fluoresce in red (exemplary signal labeled as "BiP") and DNA by DAPI to fluoresce in blue (exemplary signal labeled as "DAPI"). Representative staining of the markers is indicated. Scale bar: 10 μm. FIG. 1C graphically illustrates liver stage size. After IFAs were performed, determination of approximate liver stage size (based on area at the parasite's largest circumference using the PVM marker Hep17 as a reference) was calculated in order to make comparisons. At least 20 parasites were assessed at each time point. There was no statistical difference in area between the four parasite lines as determined by an unpaired two-tailed t-test. The results suggest that all parasites develop at a similar rate and thus all GAPs are late-arresting.

FIG. 2A shows groups of C57BL/6 mice (n≥6) were inoculated with 50,000 *P. yoelii* wildtype (solid bars), fabb/f− (open bars), or lisp2−/plasmei2− (stippled bars) sporozoites. In vivo bioluminescent imaging was used to assay liver stage development (total flux, y-axis) at 24, 44, 72 and 96 hours (x-axis) after inoculation. Significant differences are highlighted (*), based on an unpaired two-tailed t-test where $p<0.006$. ND; not determined due to transition to blood stage. Background luminescence is depicted as a dashed horizontal line. FIG. 2B shows groups of C57BL/6 mice were immunized twice with 50,000 intravenous sporozoites (*P. yoelii* fabb/f−, four mice [square] and *P. yoelii* lisp2−/plasmei2−, ten mice [triangle]) and uninfected salivary gland extract as a control (naïve, eight mice [sphere]) one month apart and intravenously challenged with 10,000 lethal YM *P. yoelii* infected red blood cells. Parasitemia was followed until clearance. All naïve mice were euthanized to avoid distress when parasitemia exceeded 65%).

FIGS. 3A-3F illustrate that *P. yoelii* lisp2−/plasmei2− GAP immunization promotes humoral responses to multiple life cycle stages. FIG. 3A shows an ELISA that was used to measure levels of antibodies that recognize circumsporozoite protein (CSP). Sera from five mock-immunized (triangles) and five GAP-immunized mice (spheres) were serially diluted and antibody titers determined. The x-axis shows the dilution and the y-axis, the OD reading after detection. FIGS. 3B-3F are photomicrographs of various *Plasmodium* life cycle stages. IFA was used to determine IgG antibody activity against the parasite from GAP-immunized mice. Sera from five pooled mice were diluted 1:200 for IFA and bound antibody was detected with a fluorescent secondary antibody. FIG. 3B: Sera from GAP-immunized mice (left panels), but not sera from naive mice (right panels), recognizes the sporozoite surface (indicated with arrow, top left panel). Differential interference contrast images of the sporozoites are shown in the bottom panels. FIGS. 3C-3E: Liver stage IFAs from GAP-immunized sera (labeled as "red") show cross reactivity with CSP (labeled as "green") at 24 hours of development (FIG. 3C) and weak internal reactivity at 34 (FIG. 3D) and 44 hours (FIG. 3E) of development (labeled as "red") where parasite is visualized with antibody to BiP (labeled as "red"). FIG. 3F: GAP-immunized sera recognize the blood stage merozoite interior (labeled as "red") and the merozoite surface was visualized with antibody to MSP1 (labeled as "green"). In FIGS. 3B-3F DNA is labeled as "blue". Scale bar in FIG. 3A and FIG. 3F: 5 μm and in FIGS. 3B-3E: 10 μm.

FIG. 4A: Parasite liver burden was assessed at 42 hours post infection by bioluminescent imaging. FIGS. 4B-4D. Mice were sacrificed and their livers perfused for isolation of liver non-parenchymal cells and phenotyping by flow cytometry. Total number of liver lymphocytes (FIG. 4B), CD8 $T_{EM}$ (as measured by the $CD8^+$, CD62L−, $KLRG1^+$ population) (FIG. 4C) and total number of antigen-experienced $CD8^+$ $CXCR6^+$ T cells (as measured by $CD8^+$, $CD44^{hi}$, $CXCR6^+$) (FIG. 4D) are shown compared to naive, challenged controls. Statistical comparisons were performed by Mann-Whitney U test where * is $p<0.05$ and ** is $p<0.01$.

FIG. 5A), previously created for *P. yoelii* transgenesis, was adapted here to create the multiple versions of the *P. falciparum* CRISPR/Cas9 plasmid (pFC; FIG. 5B) for *P. falciparum* transgenesis. To do this, the rodent malaria-specific sequences were swapped out with *P. falciparum* sequences. The EF1α or HSP70 promoter drives the expression of the drug selectable marker (hDHFR or BSD) and the Cas9 endonuclease. Dual expression of the proteins is achieved with the 2A skip peptide. In the pYC plasmid (FIG. 5A), the DHFR/TS 3UTR stabilizes the RNA and in the pFC (FIG. 5B) this was achieved with the HSP70 3UTR. The U6 RNA promoter drives the expression of the gene specific guide RNA which is seamlessly attached to the Cas9 recruiting RNA sequence (crRNA). A multiple cloning site (MCS) allows for the cloning of the regions of homology required for gene knockout.

FIG. 6A illustrates the plasmid pFC ABCC2 that was transfected into *P. falciparum* NF54 to induce the ABCC2 KO. FIG. 6B schematically illustrates that after drug selection with WR99210, the ABBC2 gene was removed from transfected parasites due to the double stranded break initiated by the targeted Cas9 and subsequent recombination with the 5UTR/3UTR element contained within pFC ABCC2 KO plasmid. Cloned parasites were assessed for gene deletion by PCR using primer pairs P1/P2 and P3/P4. FIG. 6C illustrates DNA gel electrophoresis of amplified DNA from three *P. falciparum* abcc2⁻ clones (cl 1-3) and wildtype (wt). Results show deletion of the gene in all clones due to the decreased length of the P1/P2 product and the lack of a P3/P4 product.

FIGS. 7A-7C illustrate the creation of a genetically attenuated *Plasmodium falciparum* that is a plasmei2⁻ knock out generated using CRISPR/Cas9 technology. FIG. 7A schematically illustrates the annealing sites relative to the plasmei2 gene used to test for the presence of the target gene before and after application of CRISPR/Cas9 directed to knocking out the plasmei2 gene. FIG. 7B illustrates the amplification of regions of the plasmei2 gene from wildtype *P. falciparum* (i.e., with no genetic modification). FIG. 7C illustrates the lack of amplification of any regions of the plasmei2 gene from *P. falciparum* subject the CRISPR/Cas9 deletion of the plasmei2 gene.

DETAILED DESCRIPTION

Figure 1A:
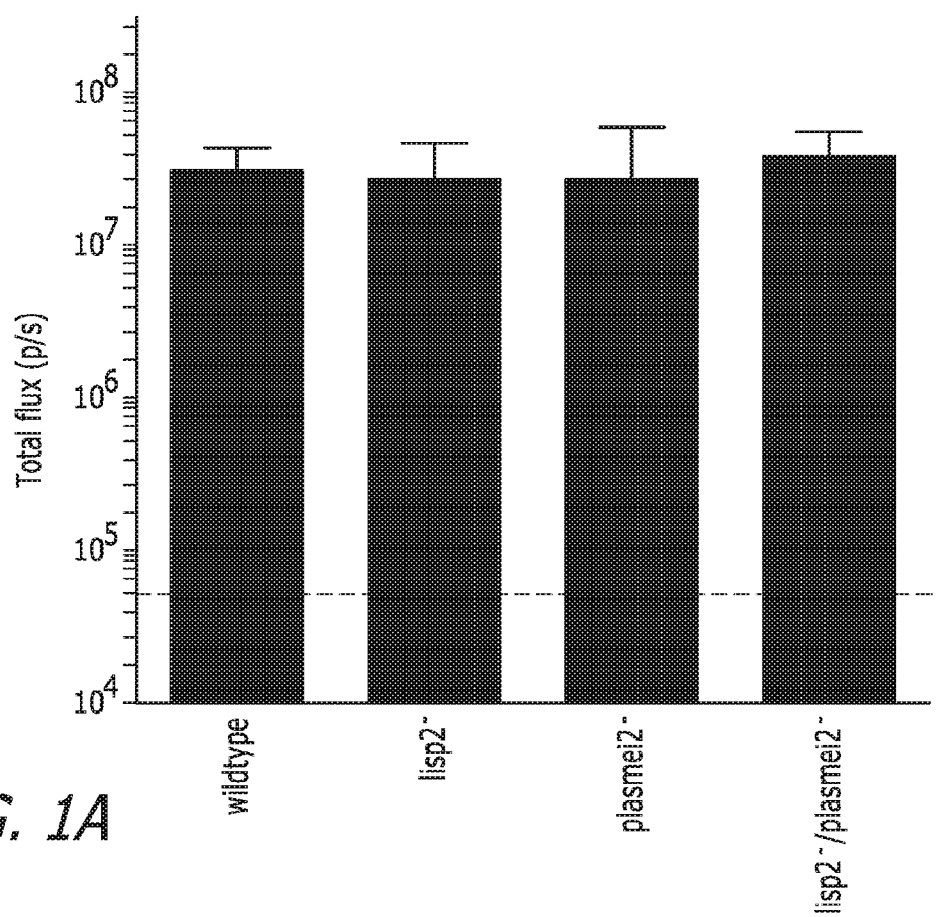
FIGS. 1A-1C illustrate that *P. yoelii* lisp2−, plasmei2− and lisp2−/plasmei2− GAPs arrest late during liver stage development.

The present disclosure is directed to attenuated malaria parasites that are completely attenuated and develop to the late liver stage. In particular, the attenuated malaria parasites have had the functionality of both the LISP2 and PlasMei2 genes interrupted. The disclosed doubly attenuated malaria parasites are useful for methods and compositions for stimulating of vertebrate host immune systems.

The disclosure is based on the inventors' work characterizing the effects of various mutations on the development of *Plasmodium* parasites. The inventors found that the specific combination of two genetic deletions in *P. yoelii* resulted in complete attenuation of the parasite, but only after the development of apparently otherwise normal liver stage forms. The finding of complete attenuation was surprising because prior characterization of each genetic deletion on its own has resulted in imperfect or incomplete late liver stage arrest. The two genetic targets for deletion, PlasMei2 and liver-specific protein 2 (LISP2), are involved in distinct biological processes. Prior experience with GAP technologies has suggested that merely combining deletions that individually result in incomplete attenuation might improve attenuation to a degree but does not necessarily achieve complete cessation of lifecycle progression. This would be especially so considering the apparent participation of each gene in unrelated processes. Complete attenuation, especially after otherwise healthy development, is a critical feature to ensure safety of any administrable composition because it ensures there is no aberrant transmission or progression of the lifecycle that would cause clinical symptoms. To achieve complete attenuation, the inventors investigated different knockout phenotypes. The inventors surprisingly found that a double knockout parasite lacking both PlasMei2 and LISP2 achieve the elusive combination of an apparently healthy developmental progression through the liver stage, but a total cessation of development prior to development of blood stages (i.e., merozoites). The double knockout parasite was completely attenuated in all mouse strains examined, arrested late in liver stage development and provided protection from both sporozoite and blood stage challenge. Furthermore, a *P. falciparum* knockout of the PlasMei2 gene was successfully generated, which also exhibited late stage arrest with no detectable transition to the blood stage in a humanized mouse model. These findings provide proof of concept for the creation of late liver stage-arresting *P. falciparum* GAP to achieve superior protection when compared to currently existing attenuated parasites.

In accordance with the foregoing, in one aspect the disclosure provides a live *Plasmodium* organism that is genetically modified to disrupt PlasMei2 gene function and LISP2 gene function.

As used herein, the terms "*Plasmodium* organism" or "parasite" refer to any parasite that belongs to the genus *Plasmodium*. In some embodiments, the *Plasmodium* organism can infect human hosts, such as, for example, *P. falciparum, P. vivax, P. ovale, P. malariae*, and *P. knowlesi*. In some embodiments, the *Plasmodium* organism is *P. falciparum*. In some embodiments, the *Plasmodium* organism is *P. vivax* or *P. ovale*. In other embodiments, the *Plasmodium* organism can infect other vertebrate hosts, such as non-human primates and rodents. Examples of such *Plasmodium* organisms include *P. yoelii, P. berghei, P. chabaudi, P. vinckei*, and *P. cynomolgi*. The term "live" refers to continued metabolic activity in the *Plasmodium* organism. In some embodiments "live" indicates that the *Plasmodium* organism is capable of eventually establishing at least a preliminary infection, for example within hepatocytes (cultured or in vivo). The *Plasmodium* organism can be in any relevant developmental stage as is practical considering the genetic attenuation. Thus, for example, the *Plasmodium* organism can be in the intra-mosquito developmental stages and infective sporozoite stage, in addition to intra-hepatocyte (liver) stage.

As used herein, the term "genetically modified" refers to a modification to the genome of the *Plasmodium* organism that results in a defined difference from the wildtype genome sequence. The genetic modification is imposed by human manipulation, e.g., by genetic engineering. Specifically, the genetic modification results in functional disruption the PlasMei2 and LISP2 genes. The term "disrupt" a gene function, and specifically "disrupt PlasMei2 gene function and LISP2 gene function," means interfering with the gene function such as to inhibit, inactivate, attenuate, or block the gene function. The interference or disruption can be accomplished, for example, by altering the gene sequence in a manner and/or to degree such that the translated protein, if any, no longer performs its wildtype function. In some embodiments, as shown below, this can be established by the failure of the modified parasite to develop past the late liver stage and/or transition to the blood stage. The genetic alteration can comprise the introduction of one or more of an addition, substitution, and deletion in the primary gene sequence. The resulting sequence can result in removal of or alteration of a functional active site, or in alteration of normal protein folding to provide a distinct secondary structure (and thus loss of an active site), as compared to the wildtype protein. In some embodiments, the genetic alteration is the removal of a portion (including all) of the gene. In some embodiments, an addition or deletion results in a least part of the translated protein that results in loss or reduction of function. Alternatively, the gene can be disrupted by influencing the rate of transcription or translation to result in lower levels of the protein product, thus lowering aggregate protein activity levels within the *Plasmodium* organism. This can be accomplished by altering promoter or other regulatory sequences in or around the gene.

The genetic modification allows for the production of a clonal population of *Plasmodium* organisms that have the same genetically defined modifications with respect to a wildtype. Accordingly, the disclosure provides a clonal population of *Plasmodium* organisms each with a genetic modification as disclosed herein.

In some embodiments, the *Plasmodium* organism lacks a functional PlasMei2 gene or lacks a functional LISP2 gene, as described above. In some embodiments, the *Plasmodium* organism lacks a functional PlasMei2 gene and lacks a functional LISP2 gene. As used herein, the term "lacks a functional gene" means the organism lacks the genetic material in its genome to encode a functional protein, which is defined in the wildtype organisms.

As described herein, the wildtype PlasMei2-encoded protein contains an RNA binding domain (RBD) that shares homology to one of the RBDs in Mei2 (Meiosis inhibited 2), initially described in the fission yeast *Schizosaccharomyces pombe*. The encoded protein is exclusively expressed in cytoplasmic granules of liver stage parasites, suggestive of a role in RNA homeostasis. An illustrative sequence of the *P. yoelii* PlasMei2 gene is set forth herein as SEQ ID NO: 1. An illustrative sequence of the orthologous *P. falciparum* PlasMei2 gene is set forth herein as SEQ ID NO:9. Accounting for potential neutral sequence variations or variations among naturally occurring orthologs, in some embodiments, a functional PlasMei2 gene is defined as comprising a nucleic acid sequence with at least 90%, 91%, 92%, 93%, 94%, 95%, 96%, 97%, 98%, and 99% sequence identity to the sequence set forth in SEQ ID NO:1 or SEQ ID NO:9. Lack of a functional PlasMei2 gene can be demonstrated by a demonstrable developmental arrest at the late liver stage of development, as described below. Especially in combination with a lack of functional LISP2 gene, this developmental arrest can be complete (i.e., complete attenuation with no liver stage breakthrough).

As described herein, the wildtype liver-specific protein 2 (LISP2)-encoded protein is expressed on the mid-to-late liver stage parasitophorous vacuole membrane (PVM) in *Plasmodium berghei* and deletion of LISP2 gene is demonstrated to lead to late liver stage arrest, with incomplete attenuation. An illustrative sequence of the *P. yoelii* LISP2 gene is set forth herein as SEQ ID NO:5. An illustrative sequence of the orthologous *P. falciparum* LISP2 gene is set forth herein as SEQ ID NO:13. Accounting for potential neutral sequence variations or variations among naturally occurring orthologs, in some embodiments, a functional LISP2 gene is defined as comprising a nucleic acid sequence with at least 90%, 91%, 92%, 93%, 94%, 95%, 96%, 97%, 98%, and 99% sequence identity to the sequence set forth in SEQ ID NO:5 or SEQ ID NO:13. Lack of a functional LISP2 gene can be demonstrated by a demonstrable developmental arrest at the late liver stage of development, as described below. Especially in combination with a lack of functional PlasMei2 gene, this developmental arrest can be complete (i.e., complete attenuation with no liver stage breakthrough).

As described herein, a *Plasmodium* organism that has the functions of both PlasMei2 and LISP2 genes interrupted exhibits complete attenuation, i.e., the complete arrest of the lifecycle development such that there is no progression ("breakthrough") of any developmental progeny beyond the arrested state into the next developmental stage. Thus, in some embodiments, the *Plasmodium* organism does not develop into a merozoite stage capable of infecting a red blood cell within the mammalian intermediate host. In some embodiments, the life cycle development of the *Plasmodium* organism within the mammalian intermediate host arrests at the late liver stage.

The mammalian host can be of any mammalian species known to be susceptible to an infection by a *Plasmodium* parasite. In some embodiments, the mammalian host is a human. In some embodiments, the mammalian host is a non-human primate. In some embodiments, the mammalian host is a rodent, such as a rat, mouse, or guinea pig.

The genetic modification can be implemented using any appropriate technique for genetic engineering. For example, as described in more detail below, both the PlasMei2 gene function and the LISP2 gene function were disrupted by deletion of the respective genes using CRISPR/Cas9 gene editing techniques (see, e.g., Zhang C, et al. 2014. Efficient editing of malaria parasite genome using the CRISPR/Cas9 system. *MBio* 5: e01414-01414; Wagner J C, et al. 2014. Efficient CRISPR-Cas9-mediated genome editing in *Plasmodium falciparum*. *Nat Methods* 11:915-918; and Ghorbal M, et al. 2014. Genome editing in the human malaria parasite *Plasmodium falciparum* using the CRISPR-Cas9 system. *Nat Biotechnol* 32:819-821; each incorporated herein by reference in its entirety). Genetic disruption can also be implemented by overexpression of an inhibitory factor. Such factors can be inserted by reverse genetics methods into a pseudogene, i.e., one that is not essential for parasite survival at any time point during the life cycle. The inhibitory factor should not confer toxicity to the parasite but rather act in disrupting PlasMei2 gene function or the LISP2 gene function. Other approaches to impose genetic recombination to impose a functional knockout to the target PlasMei2 and/or LISP2 genes are well-known. For example, see WO 2005/063991 and U.S. Pat. No. 8,168,166, each incorporated herein by reference in its entirety, which disclose for example homologous replacement strategies to remove target loci from *Plasmodium* genome.

Antisense technology has also been successfully used for disrupting *Plasmodium* gene functions. For example, exogenous delivery of phosphorothioate antisense oligonucleotides against different regions of the *P. falciparum* topoisomerase II gene resulted in sequence-specific inhibition of parasite growth (see, e.g., Noonpakdee, W., et al., Inhibition of *Plasmodium falciparum* proliferation in vitro by antisense oligodeoxynucleotides against malarial topoisomerase II, Biochem Biophys Res Commun. 302(4):659-64 (2003), incorporated herein by reference in its entirety). Similarly, transfection of an antisense construct to the *P. falciparum* clag9 gene, which had been shown to be essential for cytoadherence by targeted gene disruption, resulted in a 15-fold reduction in cytoadherence compared to untransfected control parasites (see, e.g., Gardiner, D. L., et al., Inhibition of *Plasmodium falciparum* clag9 gene function by antisense RNA, Mol Biochem Parasitol. 110(1):33-41 (2000), incorporated herein by reference in its entirety). Such approaches can be readily modified for specific application to the target PlasMei2 and/or LISP2 target genes.

Another exemplary technology that can be used to disrupt gene functions is RNA interference (RNAi) using short interfering RNA molecules (siRNA) to produce phenotypic mutations in genes. RNAi has been used as a method to investigate and/or validate gene function in various organisms, including plants, *Drosophila*, mosquitoes, mice, and *Plasmodium*. In *Plasmodium*, RNAi has been used, for example, to demonstrate the essential role of a PPI serine/threonine protein phosphatase (PfPP1) from *P. falciparum* (Kumar et al. Characterization and expression of a PPI serine/threonine protein phosphatase (PfPP1) from the malaria parasite, *Plasmodium falciparum*: demonstration of its essential role using RNA interference. *Molar. J.* 1(1):5 (2002)). RNAi has also been used to inhibit *P. falciparum* growth by decreasing the level of expression of the gene encoding dihydroorotate dehydrogenase (McRobert & McConkey. RNA interference (RNAi) inhibits growth of *Plasmodium falciparum*. *Mol. Biochem. Parasitol.* 119(2): 273-8 (2002)) and by blocking the expression of cysteine protease genes (Malotra et al., Double-stranded RNA-mediated gene silencing of cysteine proteases (falcipain-1 and -2) of *Plasmodium falciparum*. *Mol. Microbiol.* 45(5): 1245-54 (2002)). In the mouse malaria model, RNAi has been used to inhibit gene expression in circulating *P. berghei* parasites in vivo (Mohmmed et al., In vivo silencing in *Plasmodium berghei*—a mouse malaria model. *Biochem. Biophys. Res. Commun.* 309(3):506-11 (2003)). These studies have demonstrated the use of RNAi as an effective tool for disrupting gene function in *Plasmodium* organisms.

In some embodiments, the *Plasmodium* organism can be further enhanced to exhibit additional antigens that function to provide additional stimulation to a host immune system. In one embodiment, the *Plasmodium* organism comprises at least one transgene encoding a blood stage- or gametocyte-associated antigen. This element of the disclosure is described in more detail below.

In another related aspect, the disclosure provides an immunogenic composition comprising the live *Plasmodium* organism described herein. The immunogenic composition can be, for example, a vaccine composition configured for administration to a mammalian host (e.g., human). Engineered *Plasmodium* organisms in which PlasMei2 gene function and/or LISP2 gene function have been disrupted are typically grown in sexual stage cell culture, expanded in the mosquito vector. In some embodiments, expanded sporozoites can be harvested for use in immunogenic compositions (see, e.g., Al-Olayan, E. M., et al., Complete development of mosquito phases of the malaria parasite in vitro. *Science* 295:677-679 (2002)). Methods for producing attenuated, aseptic sporozoites suitable for administration as a vaccine, as well as methods for cryopreservation of sporozoites have been previously described (see, e.g., Chulay, J. D., et al. Malaria transmitted to humans by mosquitoes infected from cultured *Plasmodium falciparum*. *Am. J. Trop. Med. Hyg.* 35(1):66-8 (1986) (January); U.S. Pat. No. 7,229,627, each incorporated herein by reference in its entirety). The subject vaccine compositions are produced by suspending the attenuated live *Plasmodium* organisms in a pharmaceutically acceptable carrier. Alternative the vaccine composition can be administered by bite from an infectious mosquito vector that has been used to expand the attenuated sporozoites. Suitable pharmaceutically acceptable carriers include sterile water or sterile physiological salt solution, particularly phosphate buffered saline (PBS), as well known in the art.

In some embodiments, the genetically attenuated *Plasmodium* organisms in the composition are a clonal population with the same or substantially similar (allowing for minor genetic variations in about <1% of the genome) genomes, and more specifically containing the same genetic modifications to disrupt PlasMei2 gene function and/or LISP2 gene function.

In some embodiments, the immunogenic composition (e.g., vaccine composition) comprises the genetically modified *Plasmodium* organism as described above which additionally express at least one transgene encoding a blood stage- or gametocyte-associated antigen as described in more detail below.

Vaccines according to this disclosure can be administered by infectious mosquito bite but also parenteral administration, e.g., intradermally, subcutaneously, transcutaneously, epidermally, through mucous membranes, into submucosal tissue, intramuscularly, intraperitoneally, and intravenously. Suitable methods of administering the live attenuated sporozoites of the invention are described in PCT/US03/37498, filed Nov. 20, 2003, and U.S. Patent Application Publication No. US 2005/0220822, published on Oct. 6, 2005, both of which are incorporated herein by reference. A single inoculation or a series of two or more inoculations may be used to achieve the desired level of protection. Thus, a first priming dose of the vaccine may be followed by subsequent booster doses. The number of inoculations may range between 1 and 6 doses within a year, with additional booster doses in subsequent years.

Dosage is empirically selected to achieve the desired immune response in the host. By "immune response" is meant an acquired and enhanced degree of protective immunity, preferably complete or sterile protection, against subsequent exposure to wildtype *Plasmodium sporozoites*.

A suitable dose of genetically attenuated *Plasmodium sporozoites*, such as *P. falciparum* genetically attenuated sporozoites, per inoculation may be between about 1,000 to about 10 million sporozoites, such as between about 1,000 and 1 million sporozoites, between 5,000 and 500,000 sporozoites, between 10,000 and 250,000 sporozoites, or between 00,000 and 150,000 sporozoites. In some embodiments of the invention, a dose of at least about 1,000 genetically attenuated sporozoites are administered to a human subject per inoculation. In some embodiments of the invention, a dose of at between about 1,000 and 500,000 genetically attenuated sporozoites are administered to a human subject. In some embodiments of the invention, a dose of at between about 10,000 and 250,000 genetically attenuated sporozoites are administered to a human subject.

Accordingly, in a related aspect, the disclosure also provides a method for inducing an immune response against one or more *Plasmodium* antigens in a subject. The method comprises administering to the subject a live *Plasmodium* organism, or composition comprising the live *Plasmodium* organism, wherein the live *Plasmodium* organism is genetically modified to disrupt PlasMei2 gene function and LISP2 gene function, as described above. In preferred embodiments, inoculation of the subject confers at least a degree of protective immunity against subsequent exposure to *Plasmodium* parasites. It is generally contemplated that inoculating a subject according to the methods of the invention with genetically attenuated *Plasmodium sporozoites* of one *Plasmodium* species will induce protective immunity against challenge with wildtype *Plasmodium* parasites of the same species. However, it has been shown that immunization with sporozoites of one *Plasmodium* species can protect against challenge with another *Plasmodium*, and, thus, eliciting cross-species protection in this manner is also within the scope of the invention.

In one embodiment, the live *Plasmodium* organism administered to the subject is a *Plasmodium* in an infective sporozoite stage. Exemplary dosage and administration methods of immunogenic (e.g., vaccine) compositions are described above.

In some embodiments of the method, the subject is a human and the live *Plasmodium* is *P. falciparum, P. vivax, P. ovale, P. malariae*, or *P. knowlesi*. In a more specific embodiment, the live *Plasmodium* is *P. falciparum*.

In other embodiments, subject is a rodent and the live *Plasmodium* is *P. yoelii, P. berghei, P. chabaudi*, or *P. vinckei*. In a specific embodiment, the rodent is a mouse and the live *Plasmodium* is *P. yoelii*.

In some embodiments, the administering step results in infection of a hepatocyte of the subject. In some embodiments, the immune response ameliorates or protects against infection from a subsequent wildtype *Plasmodium* challenge. Accordingly, in some embodiments, the disclosed methods confer protective immunity sufficient to reduce the symptoms of malaria in at least 60% of subjects (e.g., humans), such as, for example at least 60%, at least 70%, at least 80%, at least 90%, at least 95%, or at least 99% of subjects, following exposure to wildtype *Plasmodium falciparum* (partial protective immunity). In some embodiments, the disclosed methods confer protective immunity sufficient to prevent malaria in at least 60% of subjects (e.g., humans), such as, for example at least 60%, at least 70%, at least 80%, at least 90%, at least 95%, or at least 99% of subjects, following exposure to wildtype *Plasmodium* (complete protective immunity). In some embodiments, 50-100% of subjects (e.g., humans), such as 95% of subjects, are completely or at least partially protected against challenge with wildtype *Plasmodium* parasites (e.g., *P. falciparum* parasites) for at least 10 months.

In another aspect, the disclosure provides a genetically attenuated *Plasmodium* parasite (GAP) that further comprises at least one transgene encoding a blood stage- or gametocyte-associated antigen. By providing for the expression of one or more blood stage- or gametocyte-associated antigens, any GAP or related composition will possess additional immunogenicity and provide additional protection against blood stage parasites (asexual and sexual). Thus, even if the GAP fully arrests prior to development into a blood stage, it will still be able to stimulate the immune cells against antigens characteristic of blood stage parasites. This provides further protection against blood stage parasites and reduces the risk of clinical symptoms as well as transmission of infection in the gametocyte antigens.

The term "genetically attenuated" indicates that the GAP has a genetic modification that leads to the reduced progression through the liver stage of development, thus, resulting in lower manifestation and/or no manifestation of clinical symptoms or parasitic burden. The genetic attenuation can be a genetic modification that results in disruption of one or more genes that are required for healthy function during the liver stage of the lifecycle. For example, the genetic modification will encompass the one or more of the modifications that result in functional disruption of the PlasMei2 and/or LISP2 genes, as described above. However, this aspect of the disclosure is not limited to disruption of the PlasMei2 and/or LISP2 genes but can be applied to other GAPs as well. For example, the GAP can contain disruptions of one or more of the following gene functions: P52, P36, SAP1, FabB/F. Such GAPs are described in more detail in, e.g., U.S. Pat. No. 8,168,166, incorporated herein by reference in its entirety.

The encoded blood stage or gametocyte antigen can be any antigen that is associated with either the asexual blood stage or the sexual blood stage (gametocyte) that has the capacity to stimulate an immune response. Representative and non-limiting examples of blood stage and gametocyte antigens appropriate for this aspect include a schizont egress antigen-1 (SEA-1) (Raj, D. K., et al., Antibodies to PfSEA-1 block parasite egress from RBCs and protect against malaria infection. *Science* 344(6186):871-877 (2014)), reticulocyte-binding family homolog 5 (Rh5) (Tran, T. M., et al., Naturally acquired antibodies specific for *Plasmodium falciparum* reticulocyte-binding protein homologue 5 inhibit parasite growth and predict protection from malaria. *J Infect Dis* 209(5):789-798 (2014); and Douglas, A. D., et al., A PfRHS-based vaccine is efficacious against heterologous strain blood-stage *Plasmodium falciparum* infection in Aotus monkeys. *Cell Host Microbe* 17(1): 130-139 (2015)), and gametocyte antigens *Plasmodium falciparum* blood stage antigen s25 (Talaat, K. R., et al., Safety and Immunogenicity of Pfs25-EPA/Alhydrogel®, a Transmission Blocking Vaccine against *Plasmodium falciparum*: An Open Label Study in Malaria Naive Adults. *PLoS One* 11(10): e0163144 (2016)) and blood stage antigen Pfs48/45 (Singh, S. K., et al., A *Plasmodium falciparum* 48/45 single epitope R0.6C subunit protein elicits high levels of transmission blocking antibodies." *Vaccine* 33 (16): 1981-1986 (2015)) or any immunogenic portion thereof.

The transgene will typically be under control of an appropriate promoter that results in transcription of the transgene during the sporozoite or liver stage of development of the engineered *Plasmodium*. Such a promoter can be a constitutive promoter or a promoter that increases expression during the sporozoite and/or liver stage. Exemplary promoters include for the sporozoite stage include the circumsporozoite protein (CSP) (Engelmann, S., et al., Transgenic *Plasmodium berghei* sporozoites expressing beta-galactosidase for quantification of sporozoite transmission. *Mol Biochem Parasitol* 146(1):30-37 (2006)) and the thrombospondin related adhesive protein (TRAP) (Kaiser, K., et al., Differential transcriptome profiling identifies *Plasmodium* genes encoding pre-erythrocytic stage-specific proteins. *Mol Microbiol* 51(5):1221-1232 (2004)), for the liver stage, LISP2 (De Niz, M., et al., In vivo and in vitro characterization of a *Plasmodium* liver stage-specific promoter. *PLoS One* 10(4):e0123473 (2015)) and for a constitutive promoter, elongation factor 1 alpha (Vaughan, A. M., et al., A Transgenic *Plasmodium falciparum* NF54 strain that expresses GFP-luciferase throughout the parasite lifecycle. *Mol Biochem Parasitol* 186(2):143-147 (2012)).

The transgene can be implemented in the GAP in any appropriate method established in the art. For example, described below in more detail, the CRISPR/Cas9 gene editing system has been successfully applied in *Plasmodium* species and can be used to express the transgene(s) with the appropriate promoters to facilitate transgenic expression of the blood stage or gametocyte stage antigen. Alternatively, more established methods can be used for transgene expression.

In some embodiments, the encoded blood stage- or gametocyte-associated antigen is configured to be expressed on the surface of, or secreted from, the *Plasmodium* organism. This can be accomplished, depending on the wildtype antigen sequence, by removing the original signal sequences and replacing them with signal sequences that result in secretion or surface expression on the liver stage. It is believed that such rationally designed transgenes allow the correct folding of the recombinant proteins and expression either beyond the sporozoite surface or at the PV/PVM interface during liver stage residency. Alternatively, appropriate motifs can be appended to the N-terminus of the protein antigen, as this approach has been used to demonstrate protein export during liver stage development (Montagna, G. N., et al., Antigen export during liver infection of the malaria parasite augments protective immunity. *MBio* 5(4): e01321-01314 (2014)).

It will be appreciated that many of the GAPs contemplated for this aspect can already endogenously encode many blood stage antigens that would be appropriate for this aspect of the disclosure. Such antigens would not normally be expressed in most cases because many GAPs are attenuated by design and arrest development prior to reaching the appropriate blood stages to permit such expression. Accordingly, in another aspect, the disclosure provides a genetically attenuated *Plasmodium* parasite (GAP) that further comprises at least one transgene with modification to the endogenous promoter sequence of an endogenous gene encoding a blood stage- or gametocyte-associated antigen, such that the blood stage- or gametocyte-associated antigen is expressed earlier in the sporozoite and/or liver stage of development. Appropriate and strong sporozoite and liver stage promoters will drive sporozoite and liver stage expression. This can be accomplished, for example, by replacing the promoter of the endogenous gene encoding the blood stage- or gametocyte-associated antigen with a constitutive promoter or a promoter that otherwise facilitates expression in the sporozoite and/or liver stage of development. Exemplary target genes, promoter sequence, and methods of implementing the genetic modification are known and described elsewhere herein. Preferably, such transgenic expression of genes does not substantially inhibit the ability of the *Plasmodium* to be cultured in mosquitos to provide infective sporozoites. This can be readily determined using routine methods.

In a further aspect, the disclosure provides a method for making a genetically modified *Plasmodium* organism as described herein and/or an immunogenic composition comprising the live *Plasmodium* organism described herein. The method comprises implementing one or more genetic modifications in a *Plasmodium* organism (e.g., wildtype or other laboratory strain) to interrupt the gene function of PlasMei2 and/or LISP2.

Typically, genetic alterations are implemented in the blood stage of life cycle development (e.g., merozoites). In some embodiments a plasmid containing the genetic modification (e.g., a full or partial gene deletion) is transfected into the blood stages of the target *Plasmodium* organism. Exemplary plasmids are described herein and can contain additional elements such as drug resistance genes to serve as a selectable marker for incorporation. The plasmid typically contains homology arms to drive the deletion of the gene of interest. Plasmids can be generated according to techniques disclosed in the art, such as using CRISPR/Cas9 followed by double crossover homologous recombination (see, e.g., Zhang C, et al. 2014. Efficient editing of malaria parasite genome using the CRISPR/Cas9 system. *MBio* 5:e01414-01414; Wagner J C, et al. 2014. Efficient CRISPR-Cas9-mediated genome editing in *Plasmodium falciparum*. *Nat Methods* 11:915-918; and Ghorbal M, et al. 2014. Genome editing in the human malaria parasite *Plasmodium falciparum* using the CRISPR-Cas9 system. *Nat Biotechnol* 32:819-821; each incorporated herein by reference in its entirety).

Parasites that have undergone successful uptake of plasmid are selected for with the appropriate drug to isolate a population of parasites that have undergone gene deletion. Once the parasite population is obtained, cloning by limiting dilution can takes place. See e.g., Janse C J, et al. 2006. High-efficiency transfection and drug selection of genetically transformed blood stages of the rodent malaria parasite *Plasmodium berghei*. *Nat Protoc* 1:346-356; incorporated herein by reference in its entirety. Optional genotyping by PCR can be used to confirm the clones that have undergone gene deletion. Furthermore, select clones of gene knockout parasites can be used for phenotypic analysis of the life cycle. The life cycle of the modified *Plasmodium* can be allowed to progress, either in in vitro culture or in a compatible mosquito host. For example, asexual parasites are converted to gametocytes and mature gametes are fed to the appropriate mosquito hosts (e.g., *Anopheles stephensi* for the *Plasmodium falciparum* parasite) and both oocyst development and salivary gland sporozoite maturation is monitored.

In some embodiments where there are multiple alterations, e.g., alterations at separate loci such as at the PlasMei2 and/or LISP2 genes, the alterations can be implemented simultaneously or serially using the above techniques. For example, the above technique for a second alteration can be performed on the initial cloned parasites with the first alteration.

Infective sporozoites within the mosquito can provide the final composition, which can be administered by allowing the mosquito to feed directly on the subject to receive the composition. Alternatively, the sporozoites can be extracted from the mosquito salivary glands, washed, and prepared for injection into the subject to receive the composition.

It is generally noted that the use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like are to be construed in an inclusive sense as opposed to an exclusive or exhaustive sense, such as in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application. Words such as "about" and "approximately" imply minor variation around the stated value, usually within a standard margin of error, such as within 10% or 5% of the stated value.

Disclosed are materials, compositions, and components that can be used for, in conjunction with, and in preparation for the disclosed methods and compositions. It is understood that when combinations, subsets, interactions, groups, etc., of these materials are disclosed each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

Exemplary Technical Description

The following describes the surprising discovery that the double interruption of LISP2 and PlasMei2 genes in *Plasmodium* allows the complete arrest of the parasitic life cycle at the end of liver stage of development. While each genetic manipulation on its own results in a partial lifecycle arrest, the specific combination of these specific genetic manipulations synergistically achieved a complete cessation of life cycle progression, preventing any development whatsoever into the blood stage. This prevented both serious disease symptoms as well as any potential transmission through a mosquito vector. As an additional benefit, the complete arrest occurred at the very late phase of liver-stage development, permitting a more complete and extended representation of typical liver-stage antigens to the host immune system to prime a more comprehensive immune responses against future wildtype infections.

Introduction

An effective vaccine against *Plasmodium falciparum* malaria will likely be essential for eradication efforts but subunit vaccine development utilizing select parasite antigens has so far shown only modest success. In contrast, formative experimental trials in humans, using immunization with radiation-attenuated sporozoites (RAS), delivered by the bites of mosquitoes, provided near complete protection against challenge with fully infectious sporozoites (referred to as controlled human malaria infection, CHMI). More recently, vialed, cryopreserved RAS have been administered by intravenous (IV) injection and have conferred robust protection against CHMI, demonstrating the safety and efficacy of this form of vaccination. Irradiation causes DNA damage in sporozoites allowing them to retain infectivity but upon infection of hepatocytes, causes a block in DNA replication and in consequence developmental arrest of the parasite at the trophozoite/early schizont stage. This causes parasite death within the infected hepatocyte or death of both the parasite and the infected cell. Attenuated sporozoites are complex immunogens, containing thousands of unique parasite proteins, many of which are potential antibody targets against the sporozoite as well as T cell targets against the early-infected hepatocyte. As such, RAS stimulate multipronged adaptive immune responses conferring pre-erythrocytic immunity against infection, thereby preventing the onset of blood stage infection. However, if the live parasite immunogens were able to progress further through liver stage schizogony and thus, dramatically increase their biomass, as well as further diversifying their antigen repertoire, they should elicit broader and more robust immune responses than RAS. Indeed, this has been shown in humans by an alternate method of whole parasite vaccination, in which subjects undergoing prophylactic treatment with the blood stage antimalarial chloroquine were immunized with fully infectious sporozoites. In this immunization, liver stage development is normal but exoerythrocytic merozoites that are released from the liver and infect red blood cells, are killed by chloroquine. This method of whole parasite immunization engenders sterile protection against CHMI but strikingly requires an approximately 60-fold lower cumulative parasite dose when compared to RAS. However, the continuous administration of an antimalarial drug during immunization can likely not be considered a practical method of vaccination.

Targeted gene deletion technology for *Plasmodium* parasites has allowed for a more precise and controlled means for the creation of defined and reproducible batches of attenuated parasites. Initial studies of rodent malaria genetically attenuated parasites (GAP) focused on the deletion of genes that were up-regulated in infective sporozoites (UIS). The deletion of numerous UIS genes from the parasite genome did not affect sporozoite viability but instead, caused early developmental arrest of the parasite in the liver and these GAPs were robust immunogens, protecting immunized mice from sporozoite challenge. A *P. falciparum* early liver stage-arresting triple knockout GAP was created ($p36^-/p52^-/sap1^-$) and showed no evidence of breakthrough to blood stage infection in pre-clinical studies and in a recent clinical study showed no breakthrough when administered to volunteers by the bites of approximately 200 infected mosquitoes. Further *P. falciparum* GAP that arrest early during liver stage development, include *P. falciparum* $b9^-/sap1^-$ and *P. falciparum* $abccc2^-$ but these GAP have yet to be tested in humans.

Identification of early liver stage-arresting GAP gene knockout candidates relied on the transcriptional profiling of salivary gland sporozoites, which uncovered genes essential for the establishment of a liver stage infection but not necessarily genes that control development and maturation of liver stages. To identify the latter, studies of the rodent malaria liver stage proteome and transcriptome and their comparison with other life cycle stages was conducted and uncovered novel potential GAP gene candidates essential for liver stage development. These included a subset of genes encoding enzymes involved in the type II fatty acid synthesis pathway (FAS II), an apicoplast-localized pathway of prokaryotic origin. Indeed, deletion of FAS II genes in both *P. yoelii* and *P. berghei* demonstrated nearly full liver stage developmental progression through schizogony before late liver stage arrest. *Plasmodium yoelii* FAS II knockouts were completely attenuated whereas *P. berghei* knockouts showed limited breakthrough to blood stage infection. Immunization of mice with *P. yoelii* sporozoites lacking FAS II resulted in a more potent immune response and superior protection when compared to the early liver stage-arresting *P. yoelii* GAP and *P. yoelii* RAS. Importantly, immunized mice were protected after intradermal immunization and were also protected from a lethal blood stage challenge, thus exhibiting life cycle stage-transcending protection. Together, these data suggest that a late liver stage-arresting GAP will be a superior immunogen in humans and a safe, late liver stage-arresting *P. falciparum* GAP would appear to be an ideal live-attenuated vaccine strain. However, efforts to create late liver stage-arresting *P. falciparum* GAP have encountered obstacles since the deletion of genes involved in FAS II unexpectedly led to a complete defect in *P. falciparum* sporogony within the mosquito, precluding its production.

In a further effort to create novel late liver stage-arresting GAP, we and others continue to screen gene deletions of liver stage-expressed genes for a phenotype of late liver stage developmental arrest in rodent malaria parasites. Two identified independent gene deletions that lead to late liver-stage arrest include PlasMei2 in *P. yoelii* (Dankwa D A, et al. 2016. A *Plasmodium yoelii* Mei2-Like RNA Binding Protein Is Essential for Completion of Liver Stage Schizogony. *Infect Immun* 84:1336-1345, incorporated herein by reference in its entirety) and liver-specific protein 2 (LISP2) in *P. berghei* (Annoura T, et al. 2014. Two *Plasmodium* 6-Cys family-related proteins have distinct and critical roles in liver-stage development. *FASEB J* 28:2158-2170; Kumar H, et al. 2016. Protective efficacy and safety of liver stage attenuated malaria parasites. *Sci Rep* 6:26824; and Orito Y, et al. 2013. Liver-specific protein 2: a *Plasmodium* protein exported to the hepatocyte cytoplasm and required for merozoite formation. *Mol Microbiol* 87:66-79; each incorporated herein by reference in its entirety). We here tested whether dual deletion of PlasMei2 and LISP2 could synergize to create a safe, fully attenuated GAP. Our studies surprisingly show that *P. yoelii* plasmei2$^-$/lisp2$^-$ constitutes a synthetic lethal gene deletion combination that completely attenuates the parasite while maintaining a late liver stage-arresting phenotype. Immunization of mice with *P. yoelii* plasmei2$^-$/lisp2$^-$ elicited robust T cell and antibody responses and afforded complete protection against sporozoite challenge as well as stage-transcendent protection against a blood stage challenge.

Results

*P. yoelii* Plasmei2$^-$ and *P. yoelii* Lisp2$^-$ Show Incomplete Attenuation of Liver Stage Development

*Plasmodium. yoelii* PlasMei2 contains an RNA binding domain (RBP) that shares homology to one of the RBDs in Mei2 (Meiosis inhibited 2), originally described in the fission yeast *Schizosaccharomyces pombe* (Egel R, et al. 1990. Sexual differentiation in fission yeast. Trends Genet 6:369-373; incorporated herein by reference in its entirety). PlasMei2 is expressed in cytoplasmic granules of liver stage parasites, suggestive of a role in RNA homeostasis. We have previously shown that deletion of PlasMei2 in *P. yoelii* 17XNL leads to late liver stage arrest and no evidence of breakthrough to blood stage infection at an IV challenge dose of 50,000 plasmei2$^-$ sporozoites in highly susceptible BALB/cByJ mice. To determine if higher doses could lead to breakthrough, we here performed IV challenges with 200,000 or 500,000 plasmei2$^-$ sporozoites in cohorts of 30 BALB/cByJ mice for each dose and did observe occasional breakthrough to blood stage infection (3/30 at 200,000, and 4/30 at 500,000, TABLE 1). This finding shows that *P. yoelii* plasmei2$^-$ is severely but not completely attenuated in highly susceptible mice given high dose challenges. We next thought that the simultaneous deletion of two liver stage-expressed genes, each of which causes incomplete attenuation at late liver stage, could achieve complete attenuation by creating a synthetic lethal phenotype, assuming that the lack of each unique gene function could synergize in their detrimental effect on liver stage development. We thus considered further gene candidates and chose to study LISP2 because it is expressed on the mid-to-late liver stage parasitophorous vacuole membrane and deletion of *P. berghei* LISP2 leads to incomplete late liver stage growth arrest. We first tested whether *P. yoelii* lisp2$^-$ arrests during late liver stage development by deleting the gene using the recently described CRISPR/Cas9 technology (Zhang C, et al. 2014. Efficient editing of malaria parasite genome using the CRISPR/Cas9 system. *MBio* 5:e01414-01414; incorporated herein by reference in its entirety), which allows efficient editing of the parasite genome. The advantage to this system is that transgenic parasites do not carry a drug susceptibility marker and thus can easily undergo further genetic manipulation. The pYC plasmid (Zhang C, et al. 2014. *MBio* 5:e01414-01414; incorporated herein by reference in its entirety) was thus used to target LISP2 for deletion in a marker-free *P. yoelii* 17XNL parasite that constitutively expresses a GFP-luciferase fusion (Lin J W, et al. 2011. A Novel 'Gene Insertion/Marker Out' (GIMO) Method for Transgene Expression and Gene Complementation in Rodent Malaria Parasites. *PLoS One* 6:e29289; incorporated herein by reference in its entirety) termed 1971cl1. This allows for the non-invasive analysis of liver stage development in mice using an in vivo imaging system (IVIS), and analysis of subsequent transition to blood stage infection in the same animals. Two *P. yoelii* lisp2$^-$ clones from two separate transfections were used for studies and neither showed defects in any stages of the parasite life cycle (data not shown) except during liver stage development. To determine if *P. yoelii* lisp2$^-$ arrests during liver stage development, groups of BALB/cJ mice were IV challenged with either 1,000 marker-free GFP-luciferase expressing 1971cl1 parent parasites (hereafter referred to as wildtype) or 1,000 lisp2$^-$ sporozoites and time to blood stage patency was determined. All wildtype-infected mice became blood stage patent on day three after challenge whereas two of seven *P. yoelii* lisp2$^-$-infected mice did not become patent and the remaining mice showed severe delays to patency, becoming patent between five and seven days after infection (TABLE 1). When mice were challenged with 10,000 lisp2$^-$ sporozoites, all mice became blood stage patent from days four through six (TABLE 1), demonstrating the incomplete attenuation of *P. yoelii* lisp2$^-$.

TABLE 1

Attenuation of gene knockout *P. yoelii* pre-erythrocytic stages in BALB/c mice.

| Parasite | Inoculation[a] | Mouse | Patent[b] | Day to Patency[c] |
|---|---|---|---|---|
| 1971cl1[d] | 1,000 | BALB/cJ | 3/3 | 3 |
| 1971cl1[d] | 10,000 | BALB/cJ | 3/3 | 3 |
| lisp2$^-$ | 1,000 | BALB/cJ | 6/8 | 5(4) 7(2) |
| lisp2$^-$ | 10,000 | BALB/cJ | 7/7 | 4(2) 5(4) 6(1) |
| plasmei2$^-$ | 50,000 | BALB/cByJ | 0/10 | — |
| plasmei2$^-$ | 200,000 | BALB/cByJ | 3/30 | 5(2) 6(1) |
| plasmei2$^-$ | 500,000 | BALB/cByJ | 4/30 | 5(2) 6(1) 7(1) |
| plasmei2$^-$/lisp2$^-$ | 50,000 | BALB/cJ | 0/30 | — |
| plasmei2$^-$/lisp2$^-$ | 50,000 | BALB/cByJ | 0/10 | — |
| plasmei2$^-$/lisp2$^-$ | 200,000 | BALB/cByJ | 0/29 | — |
| plasmei2$^-$/lisp2$^-$ | 500,000 | BALB/cByJ | 0/26 | — |
| fabb/f$^-$ | 500,000 | BALB/cJ | 0/10 | — |
| fabb/f$^-$ | 500,000 | BALB/cByJ | 0/20 | — |

Figure 1C:
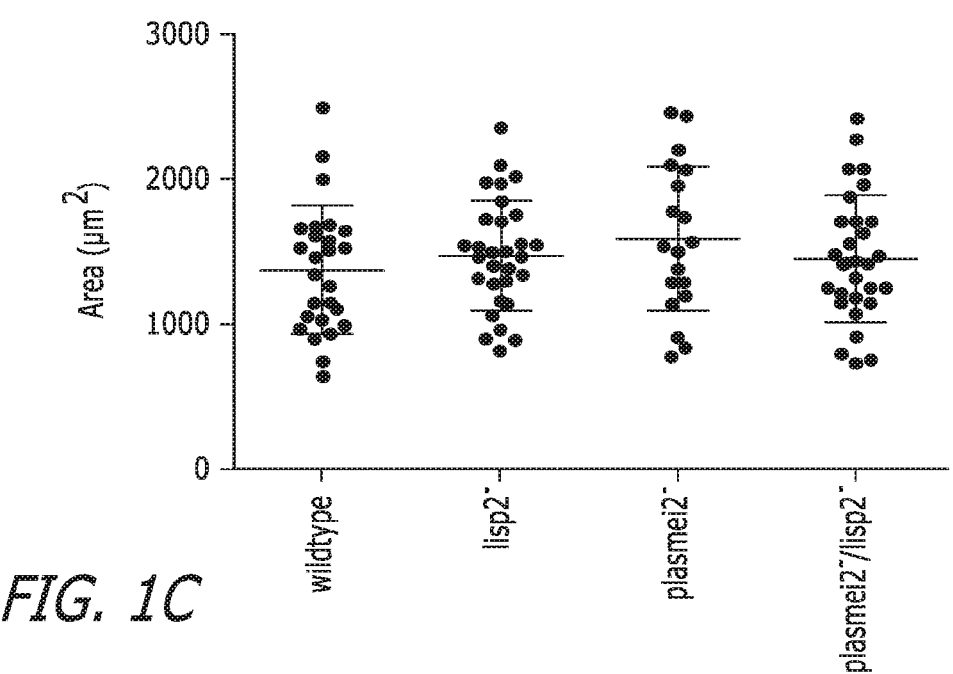
Figure 1B:
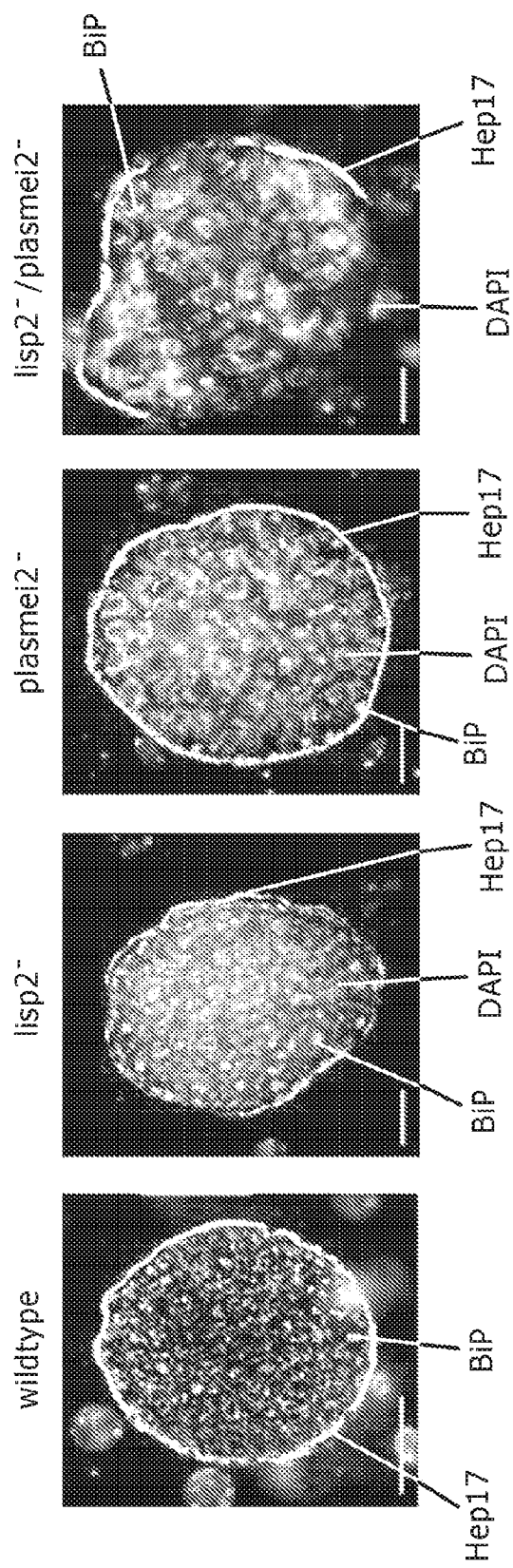
Figure 2A:
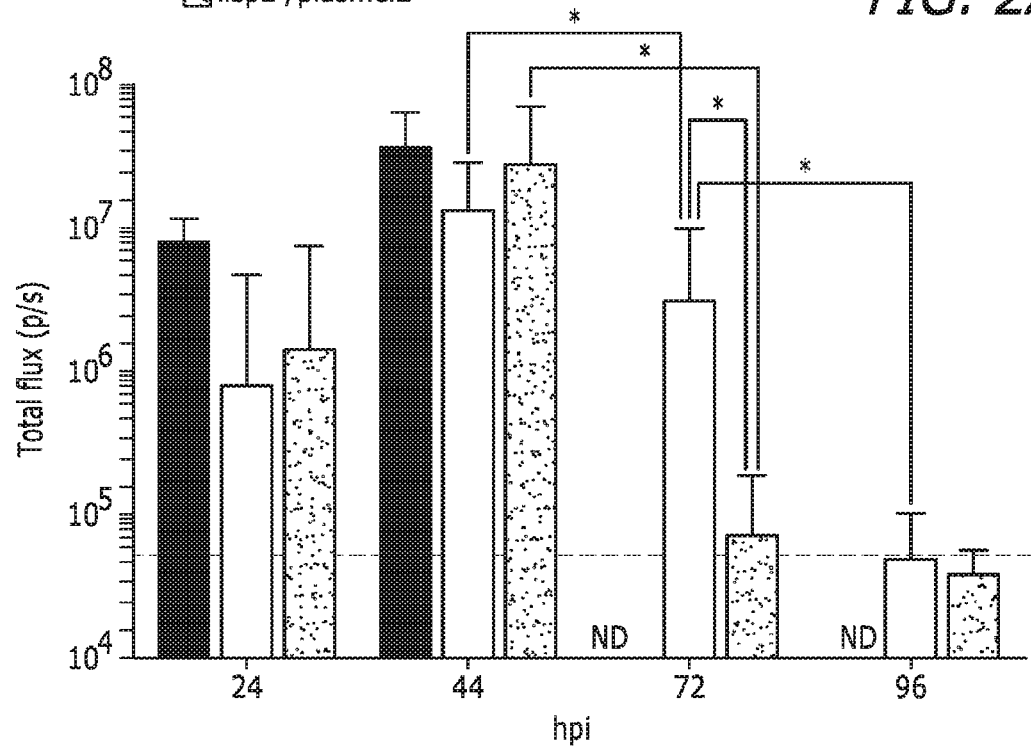
FIGS. 2A and 2B illustrate that late-arresting *P. yoelii* GAPs persist and protect from a lethal blood stage challenge.

[a]Salivary gland sporozoites were isolated from infected *Anopheles stephensi* mosquitoes and mice were IV challenged with the listed number of sporozoites.
[b]The number of patent mice and the number of mice challenged is indicated. Detection of blood stage patent parasitemia was carried out by Giemsa-stained thin blood smear. Attenuation was considered complete if mice remained blood stage negative for 21 days.
[c]If mice became blood stage patent, the number of mice is indicated as well as the day on which the mouse became patent, in parentheses.
[d]The marker-free GFP-luciferase expressing 1971cl1 parasite has a wildtype phenotype in all aspects of the life cycle, including sporozoite infectivity and was used for the creation of all of the gene knockouts The *P. yoelii* Lisp2⁻/Plasmei2⁻ GAP Exhibits Complete Late Liver Stage Developmental Arrest Next, we created a *P. yoelii* lisp2⁻/plasmei2⁻ gene deletion parasite by deleting PlasMei2 in the drug susceptible *P. yoelii* lisp2⁻ parasite. Two *P. yoelii* lisp2⁻/plasmei2⁻ parasite clones from separate transfections were phenotypically analyzed and, as for the single gene deletion parasites, there was no apparent impairment of the parasite life cycle during asexual blood stage replication, sexual stage and mosquito stage development as well as sporozoite infection of the mosquito salivary glands (data not shown). We then compared liver stage development of the lisp2⁻/plasmei2⁻ dual gene deletion parasite with lisp2⁻ and plasmei2⁻ single gene deletion parasites as well as wildtype parasites. Groups of Swiss Webster (SW) mice were challenged IV with 50,000 sporozoites of each strain and liver stage developmental progression was measured, based on luciferase activity at 43 hours. Parasite development, based on luciferase expression was indistinguishable between single and dual gene knockout parasite strains and wildtype parasites (FIG. 1A) suggesting that all three GAPs progress to late liver stage development. To further assess the phenotype of liver stage development, parasites were visualized by indirect immunofluorescence assay (IFA) at 43 hours of liver stage development, using antibodies recognizing the PVM protein Hep17 and the endoplasmic reticulum protein BiP (FIG. 1B). Liver stages of GAPs developed to late schizogony and appeared similar to wildtype in expression patterns of Hep17 (FIG. 1B). However, the plasmei2⁻ liver stages showed a DNA segregation phenotype and aberrant BiP expression and this phenotype was also observed in the lisp2⁻/plasmei2⁻ liver stages (FIG. 1B). To quantify liver stage growth of the gene knockout parasite lines, liver stage size was determined at 43 hours in comparison to wildtype (FIG. 1C) and no significant differences were seen among all analyzed strains. Thus, *P. yoelii* lisp2⁻/plasmei2⁻ GAP retains the late-liver stage arresting phenotype of the single gene deletion parasites and phenotypically resembles the plasmei2 single knockout. To determine whether the lisp2⁻/plasmei2⁻ GAP persisted in the liver, we measured liver stage luciferase activity over time of the lisp2⁻/plasmei2⁻ GAP after sporozoite inoculation in C57BL/6 mice (FIG. 2A). As controls, we compared the lisp2⁻/plasmei2⁻ GAP with both the late liver stage-arresting fabb/f GAP, created in the GFP-luciferase expressing 1971cl1 parent parasite, and wildtype. All three parasites showed similar luciferase activity at 24 and 44 hours after sporozoite inoculation (FIG. 2A) and thereafter wildtype liver stage activity was not measured as the liver stage-to-blood stage transition occurs at approximately 48 hours. At 72 hours, both lisp2⁻/plasmei2⁻ GAP and fabb/f GAP luciferase activity had significantly decreased with lisp2⁻/plasmei2⁻ GAP activity at background levels whereas fabb/f GAP luciferase activity was still significantly higher than background. This suggests that the fabb/f GAP persists for longer than the lisp2⁻/plasmei2⁻ GAP. At 96 hours, both GAP had luciferase activity comparable to background. To corroborate this finding, we used IFA to assess liver stage development at 44 and 60 hours of liver stage development. Liver stage lisp2⁻/plasmei2⁻ GAP and fabb/f GAP parasites were still present at 44 hours but at 60 hours, only fabb/f GAP were detected (data not shown).

As we had observed the lowest frequency of breakthrough infections among single gene knockouts in the plasmei2⁻ parasite, we next determined if comparable high doses of lisp2⁻/plasmei2⁻ GAP would lead to breakthrough infection. We thus performed IV challenges with 200,000 or 500,000 of lisp2⁻/plasmei2⁻ sporozoites in cohorts of highly susceptible BALB/cByJ mice for each dose. Here, we did not observe any breakthrough to blood stage infection (0/29 for 200,000 and 0/26 for 500,000, TABLE 1). This finding shows that the *P. yoelii* lisp2⁻/plasmei2⁻ gene knockout combination constitutes a synthetic lethal phenotype in which two sub-lethal single gene deletions synergize to cause a completely penetrant lethal phenotype. In consequence, the lisp2⁻/plasmei2⁻ GAP is completely attenuated at late liver stage.

The *P. yoelii* Lisp2⁻/Plasmei2⁻ GAP Protects Against Pre-Erythrocytic and Erythrocytic Stage Challenge To study pre-erythrocytic protection, groups of BALB/cJ mice were IV-immunized twice at 2-3 month intervals with 10,000 *P. yoelii* lisp2⁻/plasmei2⁻ GAP sporozoites and subsequently IV-challenged with 10,000 wildtype sporozoites 30 days after the boost (TABLE 2). Readout of protection was the absence of detectable blood stage parasitemia as determined by thin blood smear microscopy starting three days after sporozoite challenge and continuing until day 21. All immunized mice were completely protected from the wildtype sporozoite challenge and in a subset of mice tested, all mice were protected from a re-challenge 30 days after the first challenge (TABLE 2). The data demonstrate that the *P. yoelii* lisp2⁻/plasmei2⁻ GAP affords complete pre-erythrocytic stage protection and thereby prevents the onset of blood stage parasitemia.

TABLE 2

*P. yoelii* GAP protect from a sporozoite challenge.

| Mouse Strain | GAP | Prime[a] | Boost[a] | Challenge[b] | Patent[c] | Rechallenge[d] | Patent |
|---|---|---|---|---|---|---|---|
| BALB/cJ | — | —[e] | —[e] (60) | 10,000 (30) | 5/5 | — | — |
| BALB/cJ | plasmei2⁻/lisp2⁻ | 10,000 | 10,000 (60) | 10,000 (30) | 0/5 | 10,000 (30) | 0/5 |
| BALB/cJ | — | —[e] | —[e] (60) | 10,000 (40) | 5/5 | — | — |
| BALB/cJ | plasmei2⁻/lisp2⁻ | 10,000 | 10,000 (90) | 10,000 (40) | 0/14 | — | — |
| SW | — | —[e] | —[e] (30, 60) | 15 bites (30) | 5/5 | 15 bites (90)[f] | 5/5 |
| SW | plasmei2⁻/lisp2⁻ | 50,000 | 50,000 (30, 60) | 15 bites (30) | 1/10 | 15 bites (90) | 1/4 |
| SW | fabb/f⁻ | 50,000 | 50,000 (30, 60) | 15 bites (30) | 0/10 | 15 bites (90) | 1/4 |

[a]*P. yoelii* GAP salivary gland sporozoites were isolated from infected *Anopheles stephensi* mosquitoes and mice were IV immunized with the listed number of sporozoites. The day after the prime that the boost(s) took place is indicated in parentheses.
[b]Mice were either challenged IV with the listed number of wildtype sporozoites or with the listed number of infectious mosquito bites. The days after the last boost the challenge took place are indicated in parentheses.
[c]The number of patent mice and the number of mice challenged is indicated. Protection was considered complete if mice remained blood stage negative for 21 days after challenge, based on Giemsa-stained thin blood smear.
[d]Mice were rechallenged IV with the listed number of wildtype sporozoites. The days after the challenge the rechallenge took place are indicated in parentheses.
[e]Control mice were immunized with comparable amounts of salivary gland extract from uninfected mosquitoes.
[f]Control mice for the rechallenge were a separate cohort.

We next conducted immunizations using outbred SW mice, which are inherently more difficult to protect by whole *P. yoelii* sporozoite immunizations than inbred mice. We compared the lisp2⁻/plasmei2⁻ GAP with the late liver-stage-arresting fabb/f GAP, the current gold standard for pre-erythrocytic protection in mice. Groups of mice were IV-immunized three times one month apart with 50,000 sporozoites of each GAP and then challenged by the bites of 15 *P. yoelii* wildtype-infected mosquitoes 30 days after the last immunization. Nine of ten of the lisp2⁻/plasmei2⁻-immunized mice were protected and ten of ten of the fabb/f-immunized mice were protected (TABLE 2), showing that both GAPs afford protection against the natural route of sporozoite challenge.

To further test durability of protection, we re-challenged a subset of immunized SW mice five months after the original mosquito bite challenge. Mice were again challenged by the bite of 15 mosquitoes harboring wildtype *P. yoelii* sporozoites and monitored for development of parasitemia by microscopy for 21 days. All naïve controls (5/5) became blood stage positive by day four post-infection while only ¼ *P. yoelii* lisp2⁻/plasmei2⁻-immunized mice became positive on day six and only ¼ fabb/f-immunized mice was positive at day seven (TABLE 2). Taken together, these data demonstrate that immunization of outbred SW mice with late liver stage-arresting GAP induces long-term immune responses that confer robust sterile protection against sporozoite challenge.

Figure 2B:
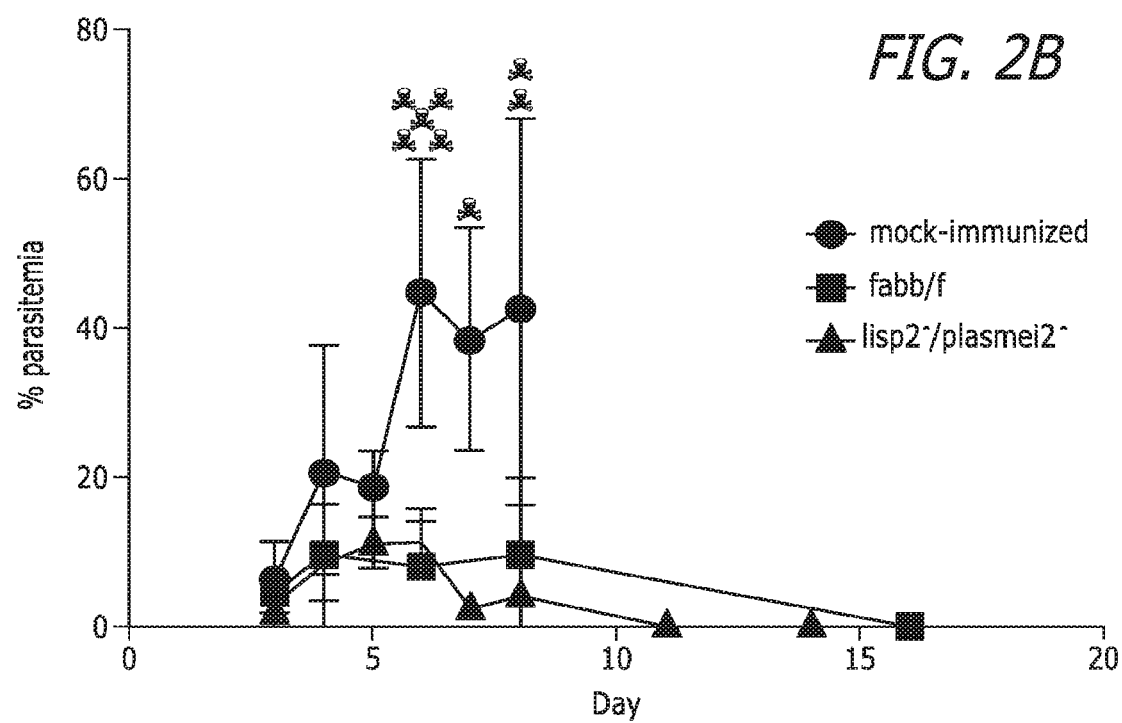

Previous work has shown that C57BL/6 mice immunized with *P. yoelii* fabb/f were protected from a direct blood stage challenge whereas early liver stage-arresting parasite immunizations such as with irradiated sporozoites did not protect against a blood stage challenge. This suggests that late liver stage-arresting parasites express protective antigens that are shared with blood stages. Since *P. yoelii* lisp2⁻/plasmei2⁻ also arrests late in liver stage development, we tested whether groups of C57BL/6 mice that were immunized with 50,000 *P. yoelii* lisp2⁻/plasmei2⁻ sporozoites or *P. yoelii* fabb/f sporozoites one month apart were protected from an IV challenge of 10,000 lethal *P. yoelii* YM blood stage parasites. Naïve mice were unable to control the blood stage infection. Conversely, both the *P. yoelii* lisp2⁻/plasmei2⁻ and *P. yoelii* fabb/f immunized mice were protected from the challenge and exhibited a low initial parasitemia before clearing the blood stage parasite infection (FIG. 2B). This result demonstrates that *P. yoelii* lisp2⁻/plasmei2⁻ sporozoite immunization engenders stage-transcending protection.

Figure 3A:
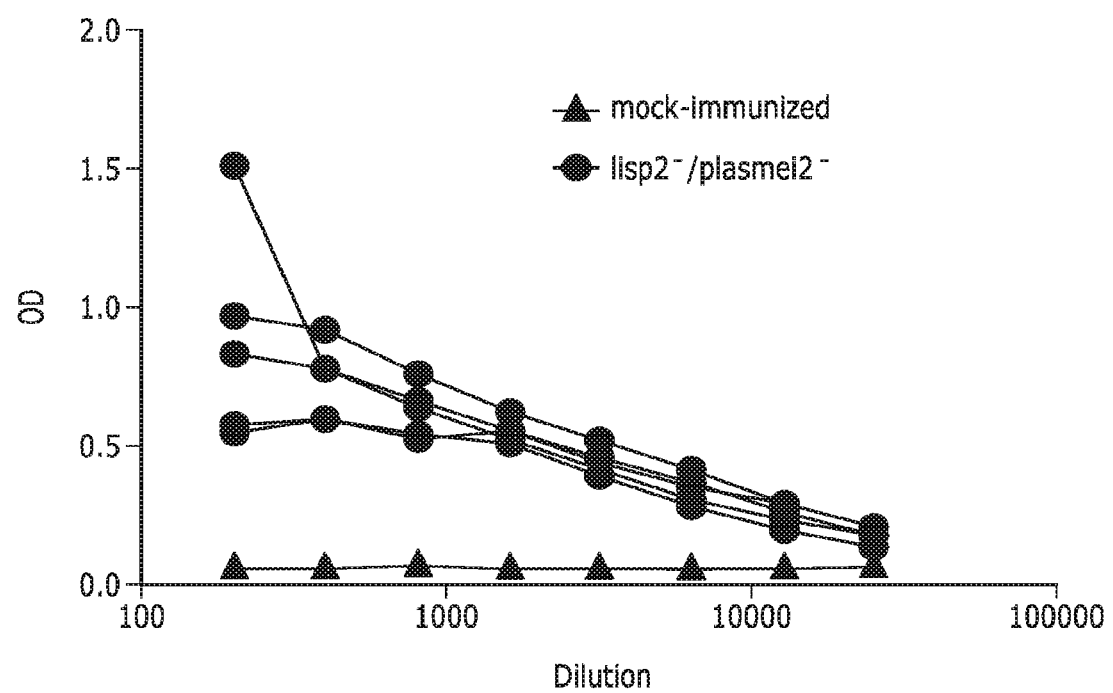
Figure 3F:
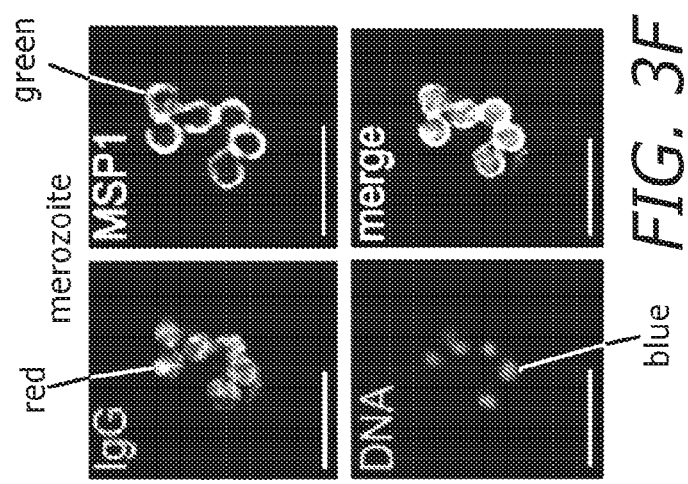
Figure 3E:
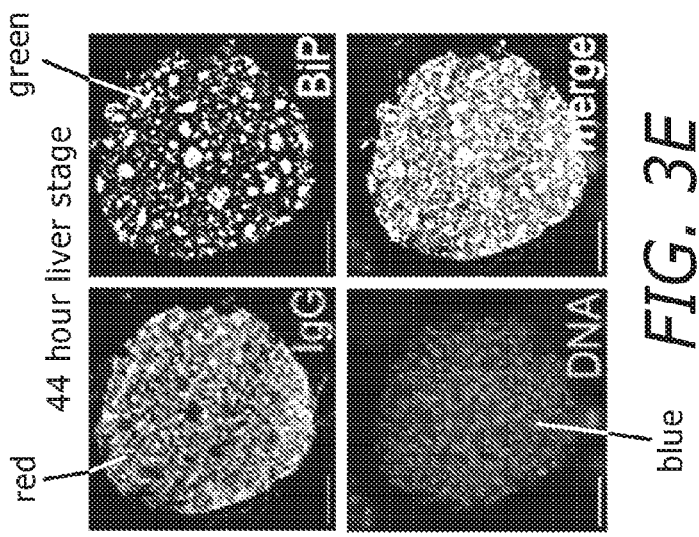
Figure 3D:
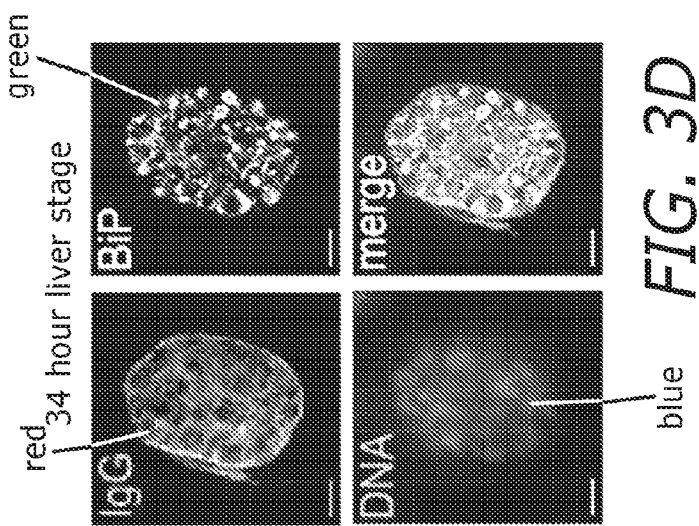

*Plasmodium yoelii* lisp2⁻/plasmei2⁻ GAP Immunization Generates Parasite Specific Antibody and T Cell Responses Mechanistic studies of pre-erythrocytic protection after GAP immunization have shown the importance of both antibody-mediated responses that target the sporozoite as well as CD8 T cell-mediated responses that target the liver stage parasites. Most rodent malaria studies have been carried out in inbred BALB/c and C57BL/6 mice. Outbred mice are less well studied but we here show protection against mosquito bite challenge in outbred SW mice after *P. yoelii* lisp2⁻/plasmei2⁻ GAP immunization (TABLE 2). With the knowledge that the natural route of challenge likely allows protective antibodies to block the sporozoite journeys from the bite site to the liver, we further investigated the pre-erythrocytic antibody response in SW mice. The circumsporozoite protein (CSP) is an immunodominant sporozoite antigen and antibodies to CSP are protective. Using an ELISA readout, we determined serum reactivity to full length *P. yoelii* CSP (see, e.g., Keitany G J, et al. 2014. Immunization of mice with live-attenuated late liver stage-arresting *Plasmodium yoelii* parasites generates protective antibody responses to preerythrocytic stages of malaria. Infect Immun 82:5143-5153; incorporated herein by reference in its entirety) in groups of five SW mice immunized as before (TABLE 2). GAP-immunized mice showed high levels of CSP reactivity whereas mock-immunized mice showed baseline activity (FIG. 3A). This demonstrates that GAP-immunized mice generate robust humoral responses to CSP, indicating the likely importance of antibodies in the pre-erythrocytic immune response after GAP-immunization. Sera were also used for IFA to show antibody binding to the sporozoite surface (FIG. 3B), in agreement with the results from the CSP ELISA. To determine if sera could also recognize liver stages and blood stage parasites, IFAs were performed on liver sections from infected mice at 24 hours (FIG. 3C), 34 hours (FIG. 3D) and 44 hours FIG. 3E) of liver stage development. Early in liver stage development at 24 hours FIG. 3C), sera reactivity showed a circumferential pattern localization in liver stages similar to CSP. Later on in liver stage development, the sera recognized the parasite periphery (surface and/or parasitophorous vacuole) but also internal structures suggesting that humoral responses are also being generated to late liver stage schizonts (FIGS. 3D and 3E). In these IFAs, antibody to BiP was used to localize the endoplasmic reticulum of the parasite and some co-localization with BiP was evident. Importantly, the immune sera also recognized asexual blood stage merozoites (FIG. 3F), and the pattern of recognition was mostly cell-internal, based on the sparse co-localization with merozoite surface protein 1 (MSP1). Thus, immunization of outbred SW mice with late liver stage-arresting GAP elicited potent humoral responses that recognize multiple parasite stages.

Figure 4A:
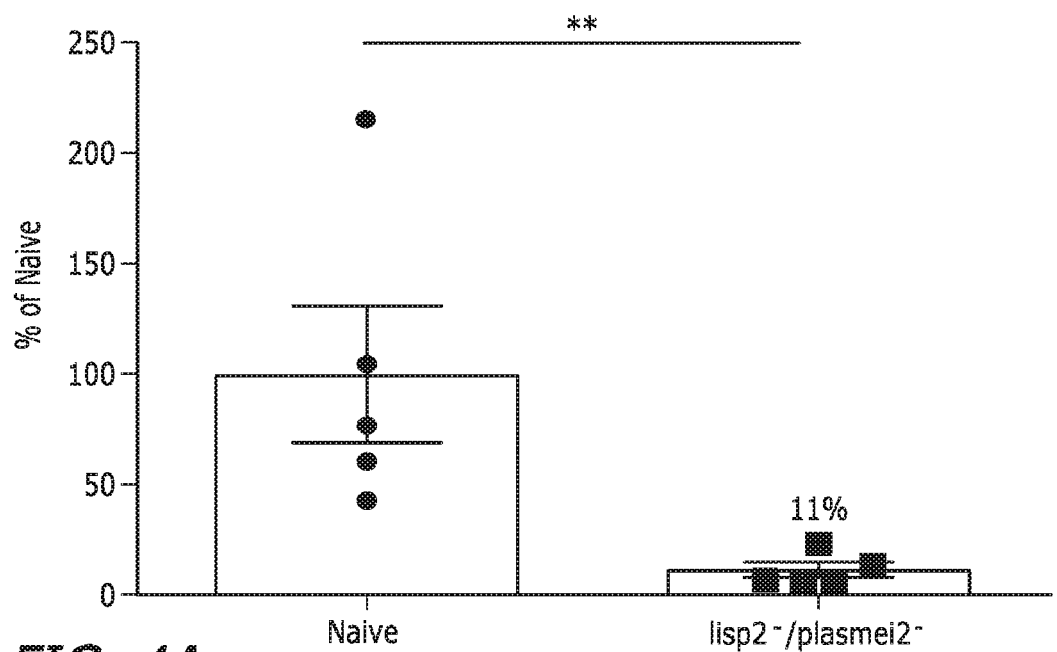
FIGS. 4A-4D illustrate that *P. yoelii* lisp2−/plasmei2− GAP immunization induces long-term liver-specific CD8 T cell immunity. SW mice were immunized three times, challenged after six weeks by mosquito bite (TABLE 2) and then re-challenged by IV injection of 7,000 luciferase-expressing *P. yoelii* sporozoites 40 days later.
Figure 4B:
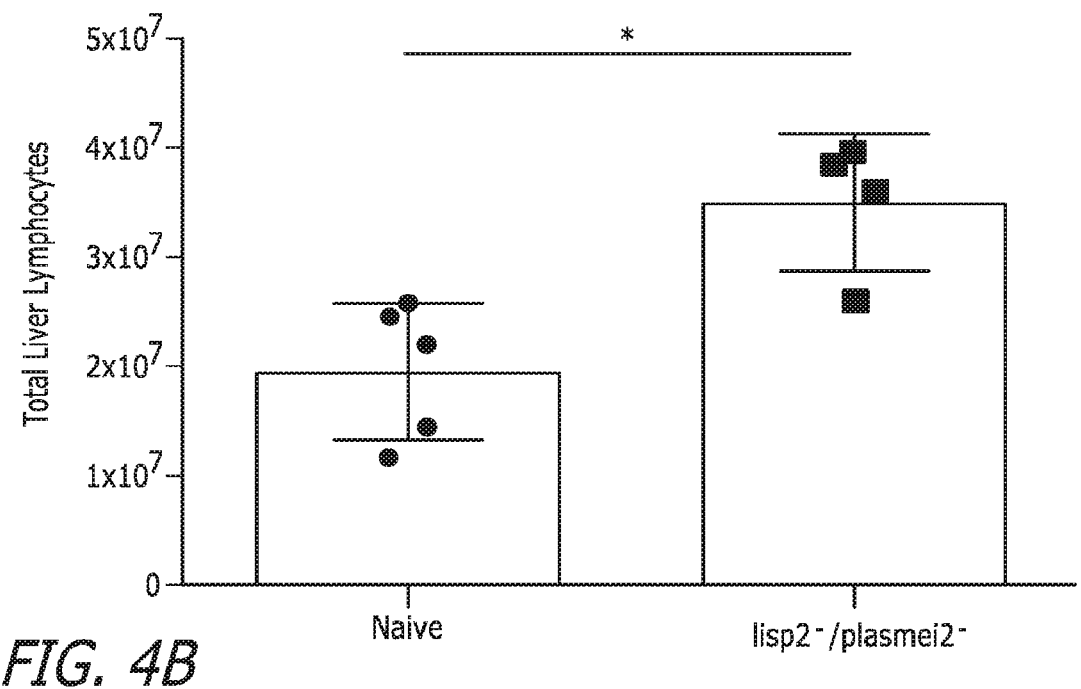
Figure 4C:
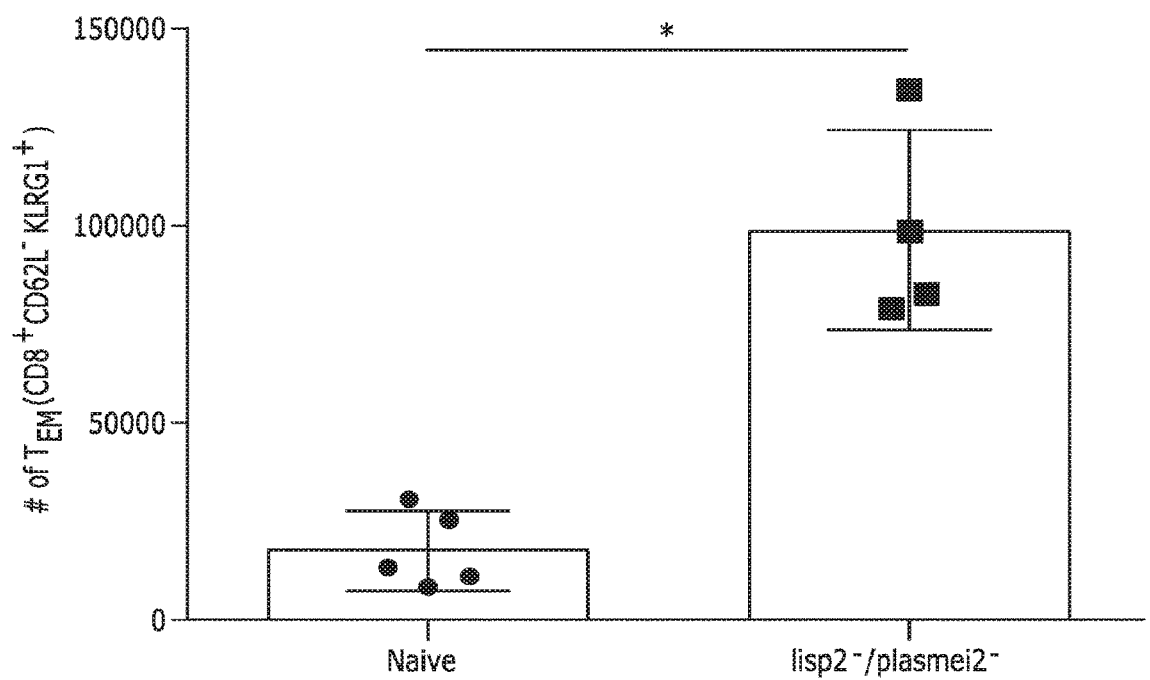
Figure 4D:
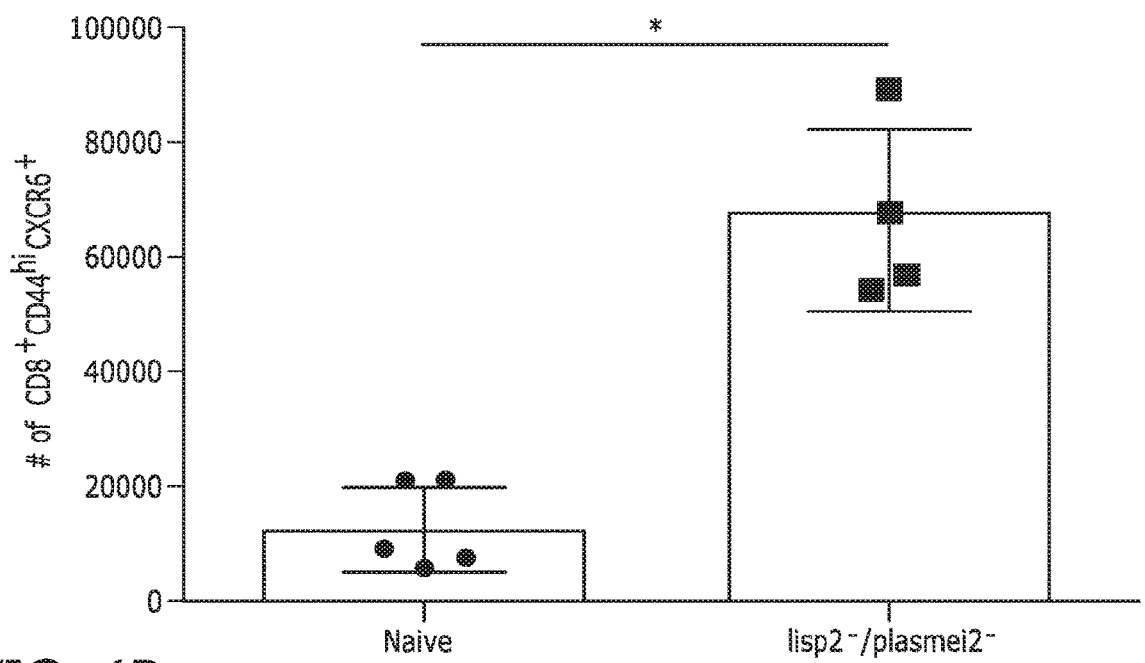
Figure 5A:
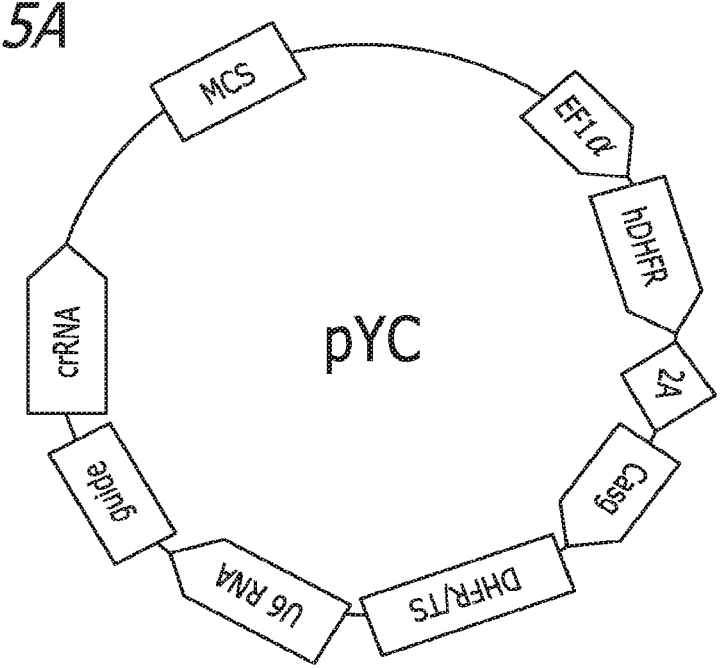
FIGS. 5A and 5B diagrammatically illustrate plasmids for CRISPR/Cas9-mediated *Plasmodium* transgenesis. The *P. yoelii* CRISPR/Cas9 plasmid (pYC.
Figure 5B:
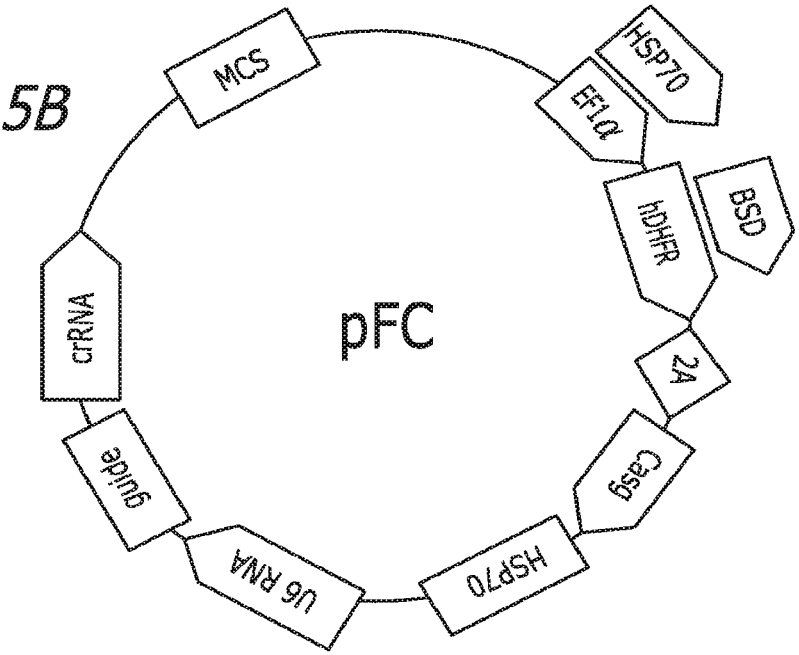
Figure 6A:
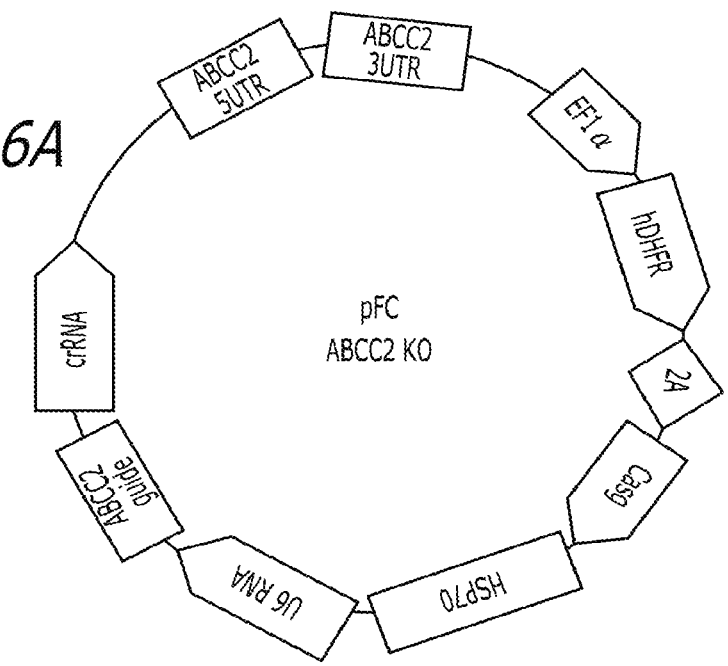
FIGS. 6A-6C illustrate the knockout of *Plasmodium falciparum* ABCC2 using plasmid pFC to demonstrate the efficacy of pFC to create knockout lines for this species.
Figure 6B:
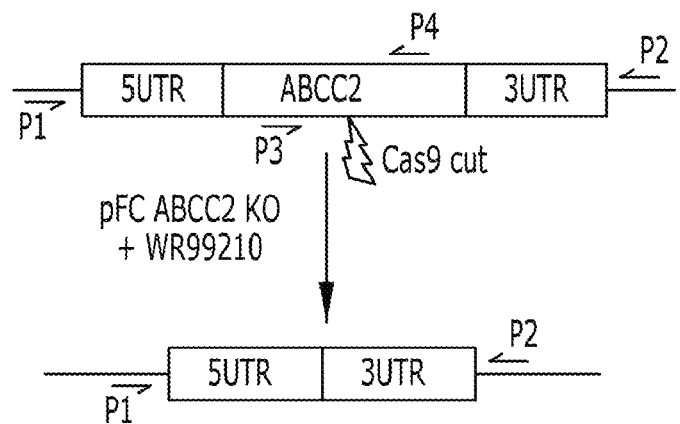
Figure 6C:
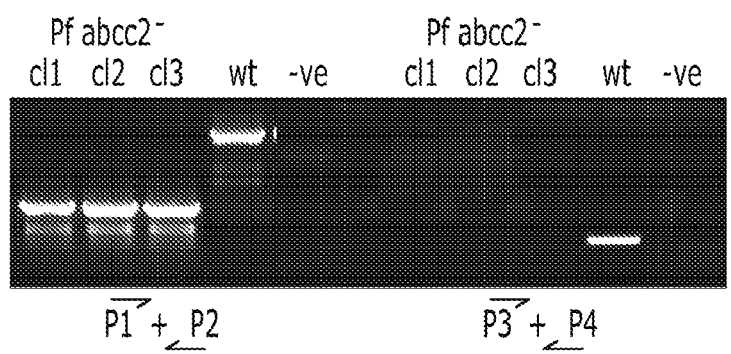
Figure 8:
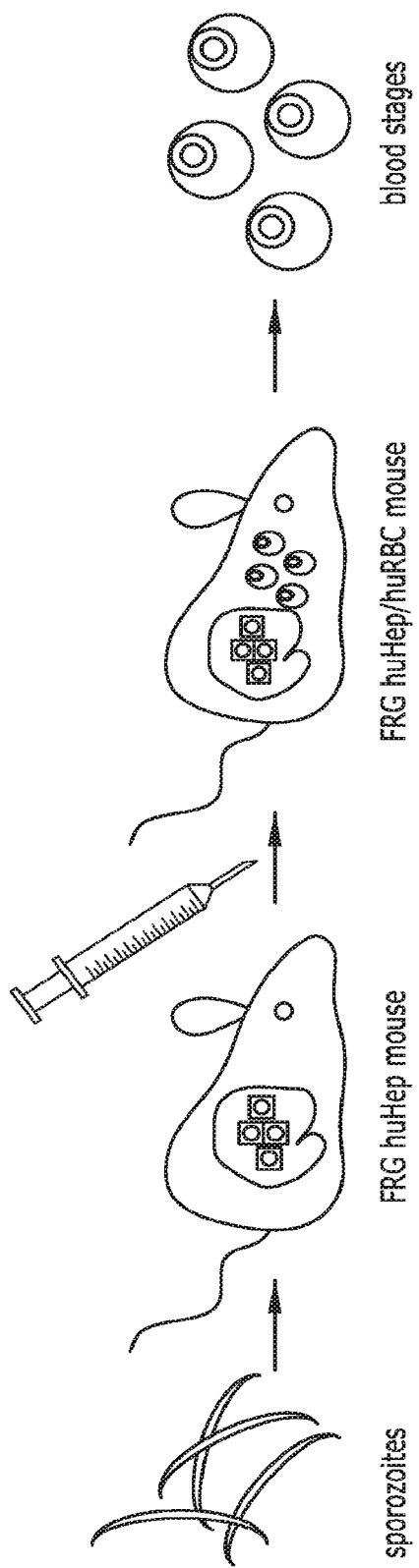
FIG. 8 is a schematic illustration of the humanized murine model for the development of the human parasite, *P. falciparum*. Sporozoites of *P. falciparum* are inoculated into FRG huHep mice, which are then administered human red blood cells. The *P. falciparum* infection is permitted sufficient time for the liver stage to transition to the blood stage. Blood samples can thereafter be assessed for development of *P. falciparum* blood stages.
Figure 9:
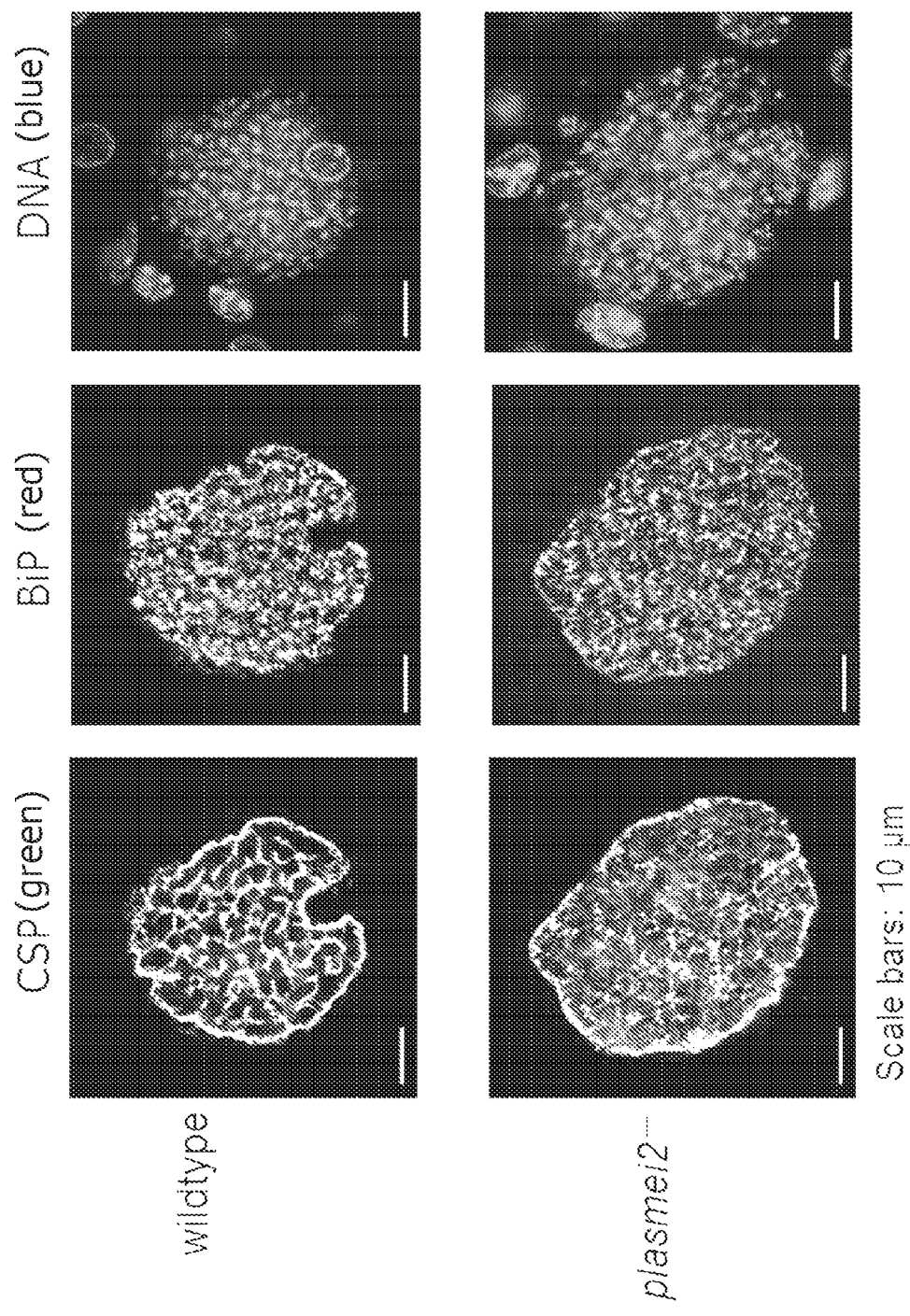
FIG. 9 is a series of photomicrographs of wildtype and plasmei2⁻ KO *P. falciparum* showing development at late liver stage schizogon, six days after sporozoite injection, in the livers of human-liver chimeric FRG huHep mice. Parasites from each of wildtype and plasmei2⁻ KO *P. falciparum* were stained for the circumsporozoite protein (CSP) (indicated as "green), BiP to show the endoplasmic reticulum (indicated as "red"), and DAPI to show DNA (indicated as "blue).

Numerous studies have shown that immunization with both GAP and RAS elicits protective CD8 T cells and CD8 T cell subsets that play critical roles include CD8 effector memory T cells ($T_{EM}$) as well as CD8 T cells that home to the liver via the chemokine receptor CXCR6. To study CD8 T cell recruitment to the liver after *P. yoelii* lisp2⁻/plasmei2⁻ GAP immunization, a subset of SW mice re-challenged by the IV injection of 7,000 *P. yoelii* GFP-luciferase sporozoites, were analyzed for liver stage burden using bioluminescence imaging at 42 hours after the challenge. Immunized mice had a significantly reduced liver stage burden of 89+/−6.9% as compared to control naïve mice (FIG. 4A), demonstrating the efficacy of the immune response in eliminating liver stage parasites. The mice were then sacrificed immediately following the measurement of parasite liver burden and their livers were perfused for phenotyping of liver-resident CD8 T cells by flow cytometry. Immunized mouse livers contained significantly more total lymphocytes than challenged naïve controls (FIG. 4B). Importantly, the livers of immunized mice had increases in CD8 $T_{EM}$ (5.7-fold increase) (FIG. 4C), known to be important in mounting rapid responses to infected hepatocytes. In addition, we also observed increased numbers of antigen-experienced CD44$^{hi}$CXCR6⁺ CD8 T cells (5.2-fold increase) (FIG. 4D) in the liver, suggesting the significance of these liver resident CD8 T cells in mounting an effective cellular response against infected hepatocytes. These data demonstrate that lisp2⁻/plasmei2⁻ GAP immunization of outbred SW mice induces protracted, liver-resident memory CD8 T cell responses that are likely important in providing robust sterile protection.

Discussion

Attenuated pre-erythrocytic *P. falciparum* malaria parasites engender immune responses that protect human subjects from an infectious sporozoite challenge. Their clinical testing was inspired and built on extensive research studies with attenuated pre-erythrocytic stages of the rodent malaria parasites *P. yoelii* and *P. berghei*. Attenuation was first achieved by the irradiation of sporozoites but more recently genetic attenuation by precise gene deletion(s) has been possible. Whereas sporozoite irradiation, by means of random DNA damage, causes the uncontrolled early arrest of the liver stage parasite before extensive DNA replication, genetic attenuation has design potential and, depending on the gene deletion, could arrest the liver stage parasite at any point during its development. Whilst first generation GAPs were built by gene deletion(s) of loci that control the early stages of hepatocyte infection, thereby causing early liver stage arrest, the deletion of genes encoding fatty acid biosynthesis (FAS II) in rodent malaria parasites caused arrest late in liver stage development. The distinct liver stage growth arrest phenotypes allowed for comparisons of the immunogenicity and efficacy of late liver stage-arresting attenuated rodent malaria GAP to early liver stage-arresting rodent malaria RAS and GAP. These studies showed that not only could late liver stage-arresting GAP confer superior protection against homologous sporozoite challenge in inbred and outbred mice, but also protected mice against a heterologous rodent malaria sporozoite challenge and a lethal blood stage challenge. The enhanced protection is likely mediated by a diversification of the antigenic targets of the protective CD8 T cell response and the antibody responses, demonstrating the importance of both arms of the immune system in this unprecedented protection. These findings provide a convincing rationale for the development of a late liver stage-arresting *P. falciparum* GAP as an optimal live-attenuated vaccine. Unfortunately however, FAS II gene deletions in *P. falciparum* prevent sporozoite formation and in consequence such a vaccine cannot be produced.

We continued our search for gene deletions that cause a late liver stage-arresting phenotype and attempted to combine gene deletions that in concert would yield a completely attenuated GAP. Here we have shown that a novel *P. yoelii* GAP, created by deletion of lisp2/plasmei2, is a synthetic lethal and completely arrests the parasite late in liver stage development. Although deletion of either gene alone is not sufficient to arrest liver stage development completely, resulting in breakthrough blood stage infection, the simultaneous deletion of both genes causes complete growth arrest and death of the parasite. Typically in synthetic lethality, a single gene deletion does not have a profound effect on phenotype but this is not always the case. In our studies, the PlasMei2 deletion had a pronounced phenotype and only showed liver stage-to-blood stage breakthrough in a small subset of susceptible BALB/cByJ mice whereas the LISP2 deletion was less deleterious and even a relatively small dose of 1000 IV sporozoites led to patency in less susceptible BALB/cJ mice. It appears counterintuitive that combining a gene deletion associated with a strong attenuation phenotype with a gene deletion with a weak attenuation phenotype would result in complete attenuation. Nevertheless, this synergistic effect was observed in the dual loss of gene function. However, the precise interaction of the LISP2 and PlasMei2 gene deletions—the former functioning at the liver stage parasitophorous vacuole (Onto Y, et al. 2013. *Mol Microbiol* 87:66-79; incorporated herein by reference in its entirety), the latter in RNA homeostasis (Dankwa D A, et al. 2016. A *Plasmodium yoelii* Mei2-Like RNA Binding Protein Is Essential for Completion of Liver Stage Schizogony. *Infect Immun* 84:1336-1345; incorporated herein by reference in its entirety)—that lead to such a severe and deleterious impact on parasite development remains to be determined. In *Plasmodium*, gene-gene interactions are poorly understood, particularly in the liver stage parasite. Research in this arena could aid in the discovery of further gene-gene interactions that could be perturbed for the purpose of GAP creation. In any event, it is demonstrated that the, successive gene deletions in *Plasmodium* using CRISPR/Cas9 technology (Zhang C, et al. 2014. Efficient editing of malaria parasite genome using the CRISPR/Cas9 system. *MBio* 5:e01414-01414; Wagner J C, et al. 2014. Efficient CRISPR-Cas9-mediated genome editing in *Plasmodium falciparum*. *Nat Methods* 11:915-918; and Ghorbal M, et al. 2014. Genome editing in the human malaria parasite *Plasmodium falciparum* using the CRISPR-Cas9 system. *Nat Biotechnol* 32:819-821; each incorporated herein by reference in its entirety), and thus, the creation of multi loci-attenuated late liver stage-arresting GAP is within reach.

We found that lisp2$^-$/plasmei2$^-$ completely protects against sporozoite challenge and also confers stage-transcending protection against a lethal blood stage challenge. The breadth and duration of the immune responses engendered by lisp2$^-$/plasmei2$^-$ vaccination might be vital for the breadth of protection. lisp2$^-$/plasmei2$^-$ GAP immunization elicited antibodies that recognized the sporozoite surface and CSP, known to be critical for humoral protection against sporozoite infection. Immune sera also recognized the liver stages at 24-, 34- and 44 hours of development as well as blood stage parasites. Although it is not clear if antibody recognition of the liver stage parasite plays a role in protection, antibody recognition of the blood stage parasite is an important component of the stage-transcending protection provided by late liver stage-arresting GAP, as previously shown for the *P. yoelii* fabb/f GAP. Indeed, *P. yoelii* lisp2$^-$/plasmei2$^-$ was as protective as *P. yoelii* fabb/f against a lethal blood stage challenge. This indicates that the induction of stage-transcending protection is a universal feature of late liver stage-arresting GAP and appears not to depend on the particular gene knockout that causes the attenuation.

Sterile immunity engendered by attenuated parasite vaccination is critically dependent on CD8 T cells that target the liver stage-infected hepatocytes. Recently, it has been shown that in addition to CD8 T$_{EM}$ cells, liver-resident CD8 T cells also play a vital role in in protection. We observed that *P. yoelii* lisp2$^-$/plasmei2$^-$ GAP immunization led to significant increases in antigen-experienced CD8 T$_{EM}$ cells and liver-resident CD8 T cells. These CD8 T cells are undoubtedly playing a significant role in conferring robust sterile protection, particularly against intravenous sporozoite challenge. This mode of challenge largely bypasses the humoral protection that plays a role in preventing sporozoites from exiting the skin after mosquito bite infection.

The enhanced magnitude and breadth of protective immune responses that is observed with late liver stage-arresting GAP provides advantages compared to early liver stage-arresting parasites. Of clinical significance, the immunizing dose of sporozoites required to achieve protection is less. Thus, the number of sporozoites per immunization can be decreased and/or the total number of immunizations can be decreased without leading to a loss of sterile protection against infection. In addition, immune responses confer protection against heterologous challenge and may even show cross-species protection, as has been demonstrated for immunization with the late liver stage-arresting *P. yoelii* fabb/f GAP, which protected against a *P. berghei* challenge. Finally, the demonstration that *P. yoelii* lisp2$^-$/plasmei2$^-$ immunization protects from a lethal, heterologous blood stage challenge raises the hope that even if sterile protection against pre-erythrocytic infection wanes, stage-transcending protection could prevent fulminant blood stage replication and as such, alleviate malaria disease. Ultimately, a late-liver stage-arresting *P. falciparum* lisp2⁻/plasmei2⁻ awaits generation and with both genes showing high conservation among malaria parasites it is possible to pursue such a promising GAP for human vaccination.

Materials and Methods

Experimental Animals

Six- to eight-week-old female SW mice from Harlan (Indianapolis, Ind.) were used for parasite life cycle maintenance and production of transgenic parasites. Six- to eight-week-old female BALB/cAnN mice from Harlan were used for assessments indirect immunofluorescence assays (IFA). Six- to eight-week-old female C57BL/6, BALB/cJ and BALB/cByJ mice from the Jackson laboratory (Bar Harbor, Me.) were used to assess the attenuation and ability of parasites to act as experimental vaccines. *P. yoelii* parent and transgenic parasites were cycled between SW mice and *Anopheles stephensi* mosquitoes for the purposes of sporozoite production. Infected mosquitoes were maintained on sugar water at 24° C. and 70% humidity. This study was carried out in strict accordance with the recommendations in the Guide for the Care and Use of Laboratory Animals of the National Institutes of Health. The Center for Infectious Disease Research has an OLAW Animal Welfare Assurance (A3640-01). The protocol was approved by the Center for Infectious Disease Research Institutional Animal Care and Use Committee.

Creation of a *P. yoelii* Lisp2⁻, Lisp2⁻/Plasmei2⁻ and Fabb/f⁻

Oligonucleotide primers used for the creation and analyses of parasites are detailed in TABLE 3. Deletion of *P. yoelii* LISP2 was achieved based on the previously reported CRISPR/Cas9 strategy using plasmid pYC (Zhang C, et al. 2014. *MBio* 5: e01414-01414; incorporated herein by reference in its entirety). In brief, LISP2 was deleted using double crossover homologous recombination following a double stranded DNA break mediated by Cas9 containing a guide RNA targeting the gene of interest. Complementary regions upstream and downstream of the open reading frame were ligated into plasmid pYC, as was the 20 nucleotide guide RNA sequence (Zhang C, et al. 2014. *MBio* 5:e01414-01414; incorporated herein by reference in its entirety), resulting in the creation of plasmid pYC_LISP2. The sequences for the 5'-flanking and 3'-flanking complementary regions are set forth herein as SEQ ID NOS:6 and 7, respectively, and the guide sequence is set forth herein as SEQ ID NO:8. The pYC plasmid were transfected into the blood stage schizonts of *P. yoelii* line 1971cl1 (Lin J W, et al. 2011. *PLoS One* 6: e29289; incorporated herein by reference in its entirety), a marker-free parasite that behaves as wildtype and expresses a green fluorescent protein (GFP)-luciferase fusion throughout the life cycle under the control of the elongation factor 1 alpha promoter. This led to the creation of the *P. yoelii* lisp2⁻. Two separate knockout clones from two independent transfections were initially phenotypically analyzed throughout the life cycle. To create *P. yoelii* lisp2⁻/plasmei2⁻, the plasmid originally used to create *P. yoelii* plasmei2⁻, pL0034_PlasMei2 (Dankwa D A, et al. 2016. *Infect Immun* 84:1336-1345; incorporated herein by reference in its entirety), was transfected into the marker free *P. yoelii* lisp2⁻ parasite and two clones from separate transfections were isolated for further analysis. In the pL0034_PlasMei2 plasmid, the sequences for the 5'-flanking and 3'-flanking complementary regions are set forth herein as SEQ ID NOS:2 and 3, respectively, and the guide sequence is set forth herein as SEQ ID NO:4. To achieve deletion of FabB/F, the GIMO technology used to create *P. yoelii* plasmei2⁻ was used and the pL0034_FabB/F plasmid was transfected into the blood stage schizonts of the luciferase expressing *P. yoelii* line 1971cl1 (Lin J W, et al. 2011. *PLoS One* 6:e29289; incorporated herein by reference in its entirety).

TABLE 3

Oligonucleotide primer sequences used for the creation and analyses of parasites*

| Primer name | Sequence (5' to 3') | SEQ ID NO: |
|---|---|---|
| LISP2 guide F | TATTCATATTGAAGATATTGCCCC | 17 |
| LISP2 guide R | AAACGGGGCAATATCTTCAATATG | 18 |
| LISP2 5UTR F | GACCATGATTACGCCAAGCTTGGTA CATCGACATTCACC | 19 |
| LISP2 5UTR R | CTTTTAGGTTTTTCTGGGCCCTTTTTATGT GTAAAAAAGTAAAATGATTATAATAAAAG | 20 |
| LISP2 3UTR F | TTTTTTACACATAAAAAGGGCCCAGA AAAACCTAAAAGAGGTAATAC | 21 |
| LISP2 3UTR R | AAACTTAAGGAATTAATTCAAGCTTGGAA ATAACTTCAAATTAAAACTACAAAATATC | 22 |
| LISP2 Test F | TTTTTTAACGATGTAACAGTGTTG | 23 |

*Oligonucleotide primer sequences used for the creation and analyses the plasmei2⁻ knockout were previously published in Dankwa DA, et al. 2016. A *Plasmodium yoelii* Mei2-Like RNA Binding Protein Is Essential for Completion of Liver Stage Schizogony. Infect Immun 84:1336-1345; incorporated herein by reference in its entirety.

After transfection of all parasites and intravenous injection into SW mice, pyrimethamine was used for the positive selection and downstream cloning of recombinant parasites using standard techniques (Janse C J, et al. 2006. High-efficiency transfection and drug selection of genetically transformed blood stages of the rodent malaria parasite *Plasmodium berghei*. *Nat Protoc* 1:346-356; incorporated herein by reference in its entirety). Transgenesis was confirmed by PCR using methodology we have used on multiple occasions [see Lindner S E, et al. 2014. Enzymes involved in plastid-targeted phosphatidic acid synthesis are essential for *Plasmodium yoelii* liver-stage development. *Mol Microbiol* 91:679-693 for a recent example; incorporated herein by reference in its entirety].

Immunofluorescence Analysis

Liver stage. BALB/cAnN mice were injected intravenously with approximately 3×10⁵ sporozoites and livers were harvested from euthanized mice at several time points post infection. Livers were perfused with 1×PBS, fixed in 4% v/v paraformaldehyde (PFA) in 1×PBS and lobes were cut into 50 µm sections using a Vibratome apparatus (Ted Pella, Redding, Calif.). For IFA, sections were permeabilized in 1×TBS containing 3% v/v $H_2O_2$ and 0.25% v/v Triton X-100 for 30 min at room temperature. Sections were then blocked in 1×TBS containing 5% w/v dried milk (TBS-M) for at least 1 hour and incubated with primary antibody in TBS-M at 4° C. overnight. After washing in 1×TBS, fluorescent secondary antibodies were added in TBS-M for 2 hours at room temperature in a similar manner as above. After further washing, the section was incubated in 0.06% w/v $KMnO_4$ for two minutes to quench background fluorescence. Sections were then washed with 1×TBS and stained with 1 µg/ml 4,6-diamidino-2-phenylindole (DAPI) in 1×TBS for 5-10 min at room temperature to visualize DNA and mounted with FluoroGuard anti-fade reagent (Bio-Rad, Hercules, Calif.).

Sporozoite. Salivary gland sporozoites were extracted from infected mosquitoes, washed once in 1×PBS and fixed in 4% v/v paraformaldehyde (PFA) in 1×PBS and allowed to dry onto 12-well microscope slides. Sporozoites were permeabilized and blocked with 3% BSA and 0.25% Triton X-100 in 1×PBS, washed three times in 1×PBS and incubated with a 1:200 dilution of mixed sera from five mock-immunized and five GAP-immunized mice. After an hour, sporozoites were washed three twice with 1×PBS and fluorescent secondary antibodies were added in 1×PBS for one hour at room temperature in a similar manner as above. Sporozoites were stained with 4 µg/ml DAPI in 1×PBS to visualize DNA, washed once with 1×PBS and mounted with FluoroGuard anti-fade reagent (Bio-Rad, Hercules, Calif.).

Blood stage. Infected red blood cells were processed for IFA using a previously described method (Tonkin C J, et al. 2004. Localization of organellar proteins in *Plasmodium falciparum* using a novel set of transfection vectors and a new immunofluorescence fixation method. *Mol Biochem Parasitol* 137:13-21; incorporated herein by reference in its entirety). Red blood cells were pelleted initially (and between all steps) at 2000 g in a microcentrifuge at room temperature for 1 minute. Cells were washed twice in 1×PBS, fixed in 1×PBS+4% v/v PFA+0.0075% v/v glutaraldehyde for 30 minutes at room temperature, and permeabilized in 1×PBS+0.2% v/v Triton X-100 for 10 minutes at room temperature. A 1×PBS+3% w/v bovine serum albumin (BSA) (blocking solution) was applied at 4° C. overnight. Primary antibodies were diluted in blocking solution and incubated for 1 hour with end-over-end rotation at room temperature. Following two washes with 1×PBS, fluorescent secondary antibodies were diluted in blocking solution and incubated with cells for 30 minutes with end-over-end rotation at room temperature and shielding from light. Nucleic acid was then stained with DAPI in 1×PBS for 5-10 minutes at room temperature. Cells were washed three times with 1×PBS, and mounted with FluoroGuard anti-fade reagent (Bio-Rad, Hercules, Calif.).

All preparations were analyzed for fluorescence using a fluorescence inverted microscope (Eclipse TE2000-E; Nikon), and images were acquired using Olympus 1×70 DeltaVision deconvolution microscopy.

Phenotypic Analysis of *P. yoelii* Liver Stages

After IFA, liver stage size was measured by determining the area of the parasite at its greatest circumference. Liver stage development was also measured using an in vivo imaging system (IVIS) since the parasites used in this study express luciferase and are thus bioluminescent. Luciferase activity in animals was visualized through imaging of whole bodies using the IVIS Lumina II animal imager (Caliper Life Sciences, USA) as previously described (Franke-Fayard B, et al. 2006. Real-time in vivo imaging of transgenic bioluminescent blood stages of rodent malaria parasites in mice. *Nat Protoc* 1:476-485; Mwakingwe A, et al. 2009. Noninvasive real-time monitoring of liver-stage development of bioluminescent *Plasmodium* parasites. *J Infect Dis* 200:1470-1478; and Ploemen I H, et al. 2009. Visualisation and quantitative analysis of the rodent malaria liver stage by real time imaging. *PLoS One* 4:e7881; each incorporated herein by reference in its entirety). Mice were injected with 100 µl of RediJect D-Luciferin (Perkin Elmer) intraperitoneally prior to being anesthetized using the isofluorane-anesthesia system (XGI-8, Caliper Life Sciences, USA). Measurements were performed within 5 to 10 minutes after the injection of D-luciferin. Bioluminescence imaging was acquired with a 10 cm field of view (FOV), medium binning factor and an exposure time of 1 to 5 minutes. Quantitative analysis of bioluminescence was performed by measuring the luminescence signal intensity using the region of interest (ROI) settings of the Living Image® 3.0 software. ROIs were placed around the whole animal and ROI measurements were expressed as total flux (photons/second).

Sporozoite Inoculation and Challenge

Sporozoites were isolated from the salivary glands of infected *A. stephensi* mosquitoes between 14 and 18 days after the infectious blood meal and injected intravenously into the tail vein of recipient mice. For assessment of attenuation, sporozoites were injected into highly susceptible BALB/cByJ mice (Kaushansky A, et al. 2015. Susceptibility to *Plasmodium yoelii* preerythrocytic infection in BALB/c substrains is determined at the point of hepatocyte invasion. *Infect Immun* 83:39-47; incorporate herein by reference in its entirety). Liver stage-to-blood stage transition (blood stage patency) was assessed by Giemsa-stained thin blood smear starting at day three after inoculation and ending at day 21, at which time, negative smear was attributed to complete attenuation. For immunizations, C57BL/6, BALB/cJ and SW mice were primed and boosted with *P. yoelii* sporozoites and subsequently challenged IV with *P. yoelii* XNL sporozoites or by *P. yoelii* XNL infectious mosquito bite. Breakthrough to blood stage patency was assessed by Giemsa-stained thin blood smear starting at day three after challenge and ending at day 21, at which time, a negative smear was attributed to complete protection. Mice immunized only with mosquito salivary gland extract were used as controls.

Blood Stage Challenge

Frozen bloodstocks of *P. yoelii* YM-infected blood were injected intraperitoneally into C57BL/6 mice and allowed to develop for two-four days until parasitemia reached a maximum of 1% as determined by Giemsa-stained thin smear. These mice were terminally bled via cardiac puncture and the blood diluted in PBS to contain 10,000 infected red blood cells/200 µL. Infected red blood cells were then injected intravenously at a volume of 200 µL/mouse into immunized recipient mice. Parasitemia was monitored by Giemsa-stained thin smears beginning on day three post-infection. Mice were euthanized when parasitemia reached 60% or became moribund.

ELISA

Anti-*P. yoelii* CSP ELISA was conducted as previously described (Sack B K, et al. 2015. Mechanisms of stage-transcending protection following immunization of mice with late liver stage-arresting genetically attenuated malaria parasites. *PLoS Pathog* 11:e1004855; incorporated herein by reference in its entirety). Briefly, high-binding 96-well plates were coated with 1 µg/mL of full-length *P. yoelii* CSP. After blocking for 1 hour at room temperature, serum samples from immunized and naïve mice were added at indicated dilutions for two hours at room temperature. After washing, HRP-conjugated anti-mouse IgG secondary antibody was then added at a 1:5000 dilution for one hour at room temperature. Plates were developed for using Sigma-Fast OPD for 12 minutes and optical density was read at a wavelength of 450 nm.

Analysis of Liver Lymphocytes

For analysis of liver lymphocytes, liver non-parenchymal cells were isolated as previously described (Miller J L, et al. 2014. Interferon-mediated innate immune responses against malaria parasite liver stages. *Cell Rep* 7:436-447; incorporated herein by reference in its entirety). Briefly, mice were anesthetized with Ketamine/Xylazine prior to perfusion of the liver with 7.5 mL HBSS with 5 mM HEPES and 0.5 mM EDTA followed by 7.5 mL of 0.5 mg/mL of collagenase in HBSS with 5 mM HEPES. Non-parenchymal cells were then isolated from liver homogenates by gradient separation using 40% iodixanol. Total lymphocytes per liver were then counted and up to $8 \times 10^6$ liver lymphocytes in 50 μL of PBS/1% FBS were stained with the following anti-mouse antibodies on ice for 1 hour: CD8 AlexaFluor488; CD44 PerCP-Cy5.5; CD127 Brilliant Violet 421; CD62L Brilliant Violet 605; B220 Brilliant Violet 785; CD3 APC; CD4 APC-Cy7; CXCR6 PE; KLRG1 PE-Cy7. Cells were then washed and run on a BD LSRII using FlowJo analysis software. Calculations of total number of cells were determined by expressing the cell type of interest as a percentage of lymphocytes based on FSC/SSC and multiplying this number to the number of lymphocytes counted from each liver.

The following describes an exemplary approach to utilize the CRISPR/Cas9 system to genetically attenuate the human malaria parasite, *Plasmodium falciparum*, in a manner similar to the attenuation of *Plasmodium yoelii*, as described above. This plasmid can be used to create a double knock out of the orthologous LISP2 and PlasMei2 genes in the human parasite to demonstrate the complete, late liver stage attenuation, and to create immune-modulatory compositions appropriate for preclinical study and human administration.

As described in more detail above, individual *P. yoelii* $lisp2^-$ and *P. yoelii* $plasmei2^-$ GAP were not completely attenuated in BALB/cByJ mice, demonstrating that mere knockout of both LISP2 and PlasMei2 would not result in a completely attenuated late-arresting GAP. Briefly, a double knockout *P. yoelii* $plasmei2^-/lisp2^-$ GAP was developed and demonstrated to surprisingly be completely arresting at the late-liver stage. To do this, CRISPR/Cas9 technology was employed in a manner that has recently been applied to *P. yoelii* as an efficient gene knockout strategy (Zhang, C., et al., Efficient editing of malaria parasite genome using the CRISPR/Cas9 system. *MBio* 5(4):e01414-01414 (2014), incorporated herein by reference in its entirety). The advantage of this strategy is that the drug selectable marker is not incorporated into the genome of the transgenic parasite, allowing for a succession of genome manipulations. The single plasmid used for manipulation, pYC, (plasmid for *P. yoelii* CRISPR/Cas9 editing), carries all the necessary sequences for manipulation and has cloning sites for (i) the insertion of the specific guide RNA that drives the specific double stranded break in the genome and (ii) the insertion of the DNA sequence necessary for recombination at the cut site (FIGS. 5A and 5B). The pYC plasmid platform was used to knockout PlasMei2 and then LISP2. As described above, the *P. yoelii* $plasmei2^-/lisp2^-$ double-knockout GAP is completely attenuated, even in susceptible BALB/cByJ mice, a promising result, demonstrating the power inherent in creating parasites with this combination of deletions. To ensure that the *P. yoelii* $plasmei2^-/lisp2^-$ still arrested late during development, liver stages were analyzed at 43 hours of development (a time point near the end of liver stage development which peaks at approximately 52 hours) and showed by bioluminescence (FIG. 1A) and by measurement (FIG. 1B) that that double knockout liver stages arrested late and were of similar size when compared to the single knockouts and wildtype parasites at this time point. This demonstrated that the double knockout still arrested late in development. Furthermore, not only did immunization of mice with *P. yoelii* $plasmei2^-/lisp2^-$ afford complete protection from sporozoite challenge, it also protected mice from a blood stage challenge (FIG. 2B), akin to the *P. yoelii* $fabb/f^-$ GAP (Butler, N. S., et al., Superior antimalarial immunity after vaccination with late liver stage-arresting genetically attenuated parasites. *Cell Host Microbe* 9(6): 451-462 (2011)), demonstrating that the *P. yoelii* $plasmei2^-/lisp2^-$ GAP is as potent as the *P. yoelii* $fabb/f^-$ GAP.

Creation of *P. falciparum* GAP has classically relied upon a positive/negative selection mechanism to achieve gene knockout (Crabb, B. S., et al., Transfection of the human malaria parasite *Plasmodium falciparum*. *Methods Mol Biol* 270:263-276) (2004), a process that can take many months before cloned parasites are ready for phenotypic assessment. This has somewhat impeded the creation of gene knockouts in *P. falciparum*. However, the CRISPR/Cas9 genome editing technique has also been adapted for *P. falciparum* genome editing by two independent groups (Ghorbal, M., et al., Genome editing in the human malaria parasite *Plasmodium falciparum* using the CRISPR-Cas9 system. *Nat Biotechnol* 32(8):819-821 (2014); Wagner, J. C., et al., Efficient CRISPR-Cas9-mediated genome editing in *Plasmodium falciparum*. *Nat Methods* 11(9):915-918 (2014)). Both of the systems designed for *P. falciparum* have led to significant decreases in the time taken to achieve clonal parasites for phenotypic testing but both rely on the transfection of two independent plasmids and dual drug selection. Since transfection efficiencies are very low, this can impede the generation of recombinant parasites. To overcome this obstacle, the pYC plasmid described above was manipulated to create a pFC plasmid (plasmid for *P. falciparum* CRISPR/Cas9 editing) (FIGS. 5A and 5B). To do this, the rodent malaria regulatory sequences were systematically removed and replaced with *P. falciparum* sequences. Specifically for pFC_LISP2, the sequences for the 5'-flanking and 3'-flanking complementary regions are set forth herein as SEQ ID NOS:14 and 15, respectively, and the guide sequence is set forth herein as SEQ ID NO:16. For pFC_PlasMei2, the sequences for the 5'-flanking and 3'-flanking complementary regions are set forth herein as SEQ ID NOS:10 and 11, respectively, and the guide sequence is set forth herein as SEQ ID NO:12. Of course, it will be understood that different or at least variant flanking and guide sequences can be employed to functionally delete or knockout the Plasmei2 and LISP2 genes based on knowledge of the wildtype *P. falciparum* sequences (SEQ ID NOS:9 and 13, respectively). In addition, alternative versions of pFC were created wherein the drug selectable marker/Cas9 expression is driven either by the EF1α promoter or by the HSP70 promoter and the drug selectable marker is either the mutated version of hDHFR, which is resistant to WR99210, or BSD, which is resistant to blasticidin (FIG. 5B).

As a control, the use of the EF1α/hDHFR containing pFC was tested in creating a gene knockout of ABCC2, which was recently shown to have an attenuated liver stage phenotype in *P. falciparum* (Rijpma, S. R., et al., Multidrug ABC transporters are essential for hepatic development of *Plasmodium sporozoites*. *Cell Microbiol* (2015). After plasmid transfection, drug resistant parasites were recovered within a month of selection and initial cloning of the parental population led to the recovery of six clones, which were all knockouts, based on PCR analysis (FIGS. 6A-6C). This demonstrates the successful application of a single plasmid platform (i.e., pFC) for effective CRISPR/Cas9 editing of a target within the *P. falciparum* genome.

The pFC platform can be used to direct the CRISPR/Cas9 editing method to delete the *P. falciparum* orthologs of the *P. yoelii* PlasMei2 gene (an illustrative sequence of the *P. falciparum* gene is set forth herein as SEQ ID NO:9) and LISP2 gene (an illustrative sequence of the gene is set forth herein as SEQ ID NO:13) to create a *P. falciparum* plasmei2$^-$/lisp2$^-$ GAP. As described above, the deletion results from double crossover homologous recombination following a double stranded DNA break mediated by Cas9 containing a guide RNA targeting the PlasMei2 and LISP2 genes. This approach utilizes plasmids such as pFC_LISP2 and pFC_PlasMei2, as described above, according to general methods described in more detail in Gorbal, M., et al., Genome editing in the human malaria parasite *Plasmodium falciparum* using the CRISPER-Ca9 system. *Nat. Biotech.* 32(8):819-821 (2014), incorporated herein by reference in its entirety, to target each gene separately. Briefly, the *P. falciparum* asexual blood stage parasites are cultured in human red blood cells in appropriate culture medium. Synchronous cultures can optionally be promoted by sorbitol treatment and/or Nycodenz enrichment. Parasites can be transfected either by electroporating ring-stage parasites or schizont stages, as previously established. Transfected clones are selected and verified for knockout using PCR. Once a single knockout is verified, the process is repeated for the second target according to the same protocol to achieve a double knockout. Verified *P. falciparum* lisp2$^-$/plasmei2$^-$ clones are selected for continuation of the lifecycle. Gametocytes of selected clones are cultured in vitro followed by in vivo production of salivary gland sporozoites in *Anopheles stephensi* mosquitoes. The developmental life cycle states are observation of the effects of the knockouts on the phenotype.

For specific assessment in the initial mammalian stages, the *P. falciparum* lisp2$^-$/plasmei2$^-$ sporozoites can be administered to a human liver-chimeric mouse model that supports robust development and transmission of the human *P. falciparum* to the blood stage of infection. This model allows for reliable pre-clinical testing of GAP attenuation. See Vaughan, A. M., et al., Complete *Plasmodium falciparum* liver-stage development in liver-chimeric mice. *J Clin Invest* 122:3618-3628 (2012), incorporated herein by reference in its entirety.

Considering the complete late-stage attenuation and excellent immunogenicity observed in the *P. yoelii* lisp2$^-$/plasmei2$^-$ parasites, the *P. falciparum* lisp2$^-$/plasmei2$^-$ strain is expected to show similar complete late-stage attenuation and immunogenic properties in both animal models and human subjects, respectively.

As described above GAPs can be produced that are confirmed to have complete attenuation late in the liver stage development. The development through the lifecycle into the late liver stage allows the progression of antigen expression, providing an abundance of a wide variety of wildtype antigens from pre-erythrocytic stages (i.e., sporozoite and liver stages) prior to attenuation. A distinct advantage of the late liver stage attenuation is also that the transgenic parasites also begin exhibit antigens characteristic of the subsequent blood stages, even if the full transition to such stages is completely aborted. This provides additional protection that transcends the developmental stage and provides an additional layer of immune stimulation and protection against existing and subsequent wildtype infection. Overall, greater quantity and breadth of antigen exposure results in stronger and more robust immune responses capable of protecting against both sporozoite and blood stage challenges. The *P. falciparum* GAP are expected to serve as a safe and potent immunogen to elicit protective immunity in human hosts in the effort to protect against future infection and malarial symptoms.

The following describes an exemplary implementation of the above CRISPR/Cas9 strategy to achieve complete knockout of the plasmei2 gene in the human malaria parasite *Plasmodium falciparum.*

A plasmid encoding the requisite sequences for knockout of the PlasMei2 gene from *Plasmodium falciparum* was generated as described above (see discussion on pFC_Plasmei2 and FIG. 5B). The parasites were transfected and after a month of incubation, were selected for the induced drug resistance. The selected parasites were assessed for presence of the Plasmei2 locus by PCR using various combinations of markers schematically illustrated in FIG. 7A. As shown in FIGS. 7B and 7C, the wildtype controls exhibited amplification of the endogenous Plasmei2 locus, whereas with the same primer pairs, the pFC_Plasmei2-transfected parasites did not exhibit amplification of an intact locus. The left two lanes demonstrate that reactions with primers annealing to the Plasmei2 locus itself did not result in amplification, whereas the right lane demonstrates that a reaction using primers annealing to flanking sites had only truncated amplification.

To assess the development of the plasmei2$^-$ knock out *P. falciparum*, sporozoites were inoculated into FRG huHep mice, followed by infusion of human red blood cells. See FIG. 8. FRG huHep is a human-liver chimeric model that permits development of human malaria, e.g., *P. falciparum*, in the liver stages. Later infusion of human red blood cells support the parasite transition from liver infection to blood stage infection in vivo and obviates the need for primate hosts to complete the *P. falciparum* life cycle. Liver cells were obtained after sufficient time to permit development to late stage schizogony (about 6 days) and were stained for the circumsporozoite protein (CSP). The endoplasmic reticulum and DNA were also stained for control. As can be seen in FIG. 9, the CSP staining in the plasmei2$^-$ *P. falciparum* lacked the defined organization of CSP that is characteristic of healthy schizogony in a wildtype liver stage parasite. This includes the onset of cytomere formation (multiple invaginations of the parasite plasma membrane), which precedes the formation of exoerythrocytic merozoites that are released at the end of liver stage development. In FIG. 9, cytomere formation is apparent in the wildtype liver stage parasite, based on CSP staining but not in the plasmei2$^-$ liver stage parasite.

To test the potential or degree of liver to blood stage transition resulting from the *P. falciparum* plasmei2$^-$ blood cells were extracted from the infected FRG huHep/huRBC mice and assessed in In vitro and in vivo assays for the presence of blood stage parasites. As demonstrated in TABLE 4, neither qPCR nor culture analyses detected any blood stage parasites in FRG huHep/huRBC mice infected with *P. falciparum* plasmei2$^-$ sporozoites. In contrast, each of these assay approaches were able to detect blood stage parasites in FRG huHep/huRBC mice infected with wildtype *P. falciparum* sporozoites.

TABLE 4

Detection of liver-stage-to-blood-stage transition in FRG huHep/huRBC mice infected with Plasmodium falciparum plasmei2⁻ via mosquito bite inoculation. In vitro and in vivo assays were performed using qRT PCR and culture analysis, respectively.

| Mouse inoculation | qRT PCR result | In vitro culture result |
|---|---|---|
| Wildtype #1 | Detected | Detected |
| Wildtype #2 | Detected | Detected |
| Wildtype #3 | Detected | Detected |
| Plasmei2⁻ #1 | Not Detected | Not Detected |
| Plasmei2⁻ #2 | Not Detected | Not Detected |
| Plasmei2⁻ #3 | Not Detected | Not Detected |

These data demonstrate that the CRISPR/Cas9 approach for genetic knock out can be implemented in the human malaria parasite *P. falciparum* to achieve the live, genetically attenuated *P. falciparum* that exhibit complete late-liver stage development arrest. This approach can thus be specifically implemented, for example, to achieve a genetically attenuated *P. falciparum* that is plasmei2⁻ and/or lisp2⁻ for purposes of a protective and/or ameliorative vaccine composition.

The following is a description of an exemplary approach to enhance anti-malarial compositions, such as GAP and related formulations, to provide for additional protection against blood stage parasites, thus further reducing risk of clinical symptoms or transmission of infection.

Introduction

Considering the additional benefit conferred by the presentation of blood stage antigens, any existing GAP-based immunogenic composition can be further enhanced by the addition or enhancement of the blood stage and/or gametocyte antigens. The additional transgenic expression of blood stage antigens by the GAP will engender improved immunity to asexual and sexual blood stages and, with respect to sexual blood stages, could add an element of transmission-blocking immunity. While the below description provides an exemplary approach for further modifying the lisp2⁻/plasmei2⁻ *Plasmodium* parasites (a "late GAP") described above to produce additional blood stage or gametocyte antigens, it will be appreciated that such modifications can be applied to other *Plasmodium*-based immunogen compositions, which would also benefit from the additional blood stage antigen expression. Such additional compositions can include other known whole *plasmodium* (including GAP)-based compositions as described in more detail above (e.g., *Plasmodium* that are p52⁻, p36⁻, and/or sap1⁻, which are examples of "early GAP") and/or in, for example, U.S. Pub. Nos. 20110033502, 20080032388, 20060121060, 20070009556, 20050233435, each incorporated herein by reference in its entirety.

The goal of this project is the creation of GAP that also express blood stage (Bs) and/or gametocyte (Gam) antigens, e.g., *P. yoelii* ($GAP^{(Py)Bs/Gam}$) and/or *P. falciparum* ($GAP^{(Py)Bs/Gam}$.

$GAP^{(Py)Bs/Gam}$

Briefly, an expression cassette containing the *P. yoelii* schizont egress antigen-1 (Py SEA-1) as a blood stage antigen, and/or Pys25 as a gametocyte antigen, and/or Pys48/45 as a gametocyte antigen, is introduced into a GAP as described above. *Plasmodium yoelii* SEA-1 is a homolog of *P. falciparum* SEA-1 (Py SEA-1), which is essential for parasite egress from the infected RBC. Antibodies against *P. yoelii* SEA-1 decrease parasite replication in vitro and vaccination of mice with recombinant *P. berghei* SEA-1 ("Py SEA-1" shares 47% similarity and 34% amino acid identity to Py SEA-1) significantly reduced parasitemia in *P. berghei* infected animals. The gametocyte antigens Pys25 and Pys48/45 (orthologs of Pfs25 and Pfs48/45) are leading transmission blocking vaccine candidates.

To create the GAP *Plasmodium* that transgenically express the blood stage and/or gametocyte antigen(s), a knock-in CRISPR/Cas9-based strategy is employed that uses double cross-over homologous recombination. The plasmid for knock-in contains an expression cassette for the blood stage antigen *P. yoelii* SEA-1, the gametocyte antigens Pys25 and/or Pys48/45 and a C-terminal epitope tag for the easy detection of expressed recombinant protein by the transgenic parasites. The circumsporozoite protein (CSP) signal sequence or PEXEL motif directs antigen expression beyond the parasite cytosol. Recombinant protein expression will be driven by sporozoite or liver stage promoters, e.g., SAP1 promoter. Alternative promoters can easily be inserted into the knock-in plasmid to drive differential recombinant protein expression, as described below.

As indicated, in one strategy, the epitope-tagged chimeric protein (or alternatively each protein individually) is placed under control of a sporozoite or liver stage promoter and 3' UTR. For instance, the SAP1 promoter will allow for sporozoite/early liver stage-specific gene expression of the transgene. Alternatively, a stronger sporozoite and early liver stage-specific promoter (e.g., the CSP promoter) or a constitutively active promoter (e.g. the EF1α promoter) can be used to ensure optimal expression of the transgene. Other exemplary constitutive promoters or promoters expressed throughout the liver stage of development include the UIS4 and FabB/F promoters. The native signal sequences and transmembrane sequences could also be removed and to improve recombinant expression. This is believed to allow the correct folding of the recombinant proteins and expression either beyond the sporozoite surface or at the PV/PVM interface during liver stage residency. As an alternative, the CSP PEXEL motifs can be additionally appended to the N-terminus of the protein antigen, as this approach has been used to demonstrate protein export during liver stage development.

Transgene expression can be verified with immunofluorescence assay (IFA) of fixed sporozoites and Western blotting of sporozoite lysates, using antibody (Ab) to the epitope tag or Ab raised against recombinant protein. To obtain antibodies that bind to the PySEA-1 and Pys25/Pys48/45, the proteins will be expressed in a HEK293 mammalian cell expression platform. Mice are immunized with the protein antigens using Adjuplex adjuvant to generate high titer, antigen-specific polyclonal Ab as a source of positive anti-Bs/Gam antibodies. Antibody titer can be confirmed by standard ELISA with serum from mice immunized with an irrelevant HIVenv protein as a negative control. To confirm that the $GAP^{(Py)Bs/Gam}$ elicits transgene product-specific antibodies, $1\times10^5$ $GAP^{(Py)Bs/Gam}$ sporozoites will be used to immunize BALB/cJ mice (a total of three immunizations, two months apart). Immunizations with corresponding GAP can serve as a negative control. One month after the last immunization, mouse sera are collected. Purified antibodies can then be used for a) Western blot and ELISA analysis against PySEA-1 and/or Pys25/Pys48/45 recombinant protein, $GAP^{(Py)Bs/Gam}$ sporozoites, and mixed blood stage lysates as a positive control, as well as GAP sporozoite lysates as a negative control, and b) IFA analysis of blood stages (for PySEA-1) and gametocytes (for Pys25/Pys48/45). GAP raised antibodies can serve as negative control. All $GAP^{(Py)Bs/Gam}$—elicited responses can be compared to responses elicited by immunization with the respective recombinant proteins. The detailed examination of the enhancement of functional, protective immunity of GAP$^{(Py)}$$_{Bs/Gam}$ to blood stages and gametocytes can be further evaluated, as described in more detail below.

GAP$^{(Py)Bs/Gam}$

GAP can also be created to transgenically express blood stage and gametocyte antigens of P. falciparum, similar to the approach described above, including the indicated promoters. Plasmodium falciparum Rh5 has recently emerged as a favored candidate for blood stage vaccination and is a member of the PfRh invasion ligands present in P. falciparum merozoites. PfRh5 is located in the rhoptries and secreted to the merozoite surface prior to RBC invasion. PfRh5 interacts with PfRipr (PfRh5-interacting protein) and studies have revealed that both are tethered to the merozoite surface via an interaction with the GPI-anchored Cysteine-rich protective antigen (CyRPA). The PfRh5-PfRipr-CyRPA complex enables PfRh5 to bind its RBC surface receptor, basigin. It has been shown that PfRh5 Ab titers are strongly associated with protection from symptomatic malaria and a recent Rh5 vaccine trial in non-human primates showed significant protection against blood stage infection. For the purpose of this investigation, PfRh5 can be codon-optimized for expression if the GAP is from a different Plasmodium species. For gametocytes, either Pfs25 or Pfs48/45 can be used. GAP$^{(Py)Bs/Gam}$ can be evaluated for transgene protein expression by Western and IFA analysis (as described above with respect to GAP$^{(Py)Bs/Gam}$). The ability of GAP$^{(Py)Bs/Gam}$ to induce antibody responses to the P. falciparum antigens following immunization can be confirmed by ELISA using recombinant protein (as described above with respect to GAP$^{(Py)Bs/Gam}$) with functional analysis as described in more detail below.

Evaluation of the Transgenic Expression of Blood Stage and/or Gametocyte Antigens As described above, the late liver stage attenuated GAP generate cross-stage protection against a blood stage challenge mediated by both CD4/CD8 T-cell and antibody responses against late liver stage antigens that are also present in the blood stages. Any GAP engineered to recombinantly express additional blood stage or gametocyte antigens can be assessed for expression and whether this leads to improved blood stage immune responses and transmission blocking (e.g., multi-stage protective immunity).

To determine the ability of the GAP$^{Bs/Gam}$ to give enhanced stage-transcending protection, a series of dose de-escalation iv-immunizations can be conducted to gain insight into the protective capacity of the novel GAP$^{Bs/Gam}$. Doses can be determined for the GAP$^{Bs/Gam}$ (and GAP without antigen knock-in expression as control) that engender complete, partial and incomplete protection by reducing both the immunizing dose and the number of iv immunizations. For each dose, efficacy studies can be conducted to determine protection against the blood stage and for the ability to inhibit transmission to mosquitoes described in detail below.

Illustrative Methods are Described Below:

Sporozoite: For sporozoite iv challenges, a Plasmodium parasite expressing GFP-luciferase will be used to allow for in vivo assessment of liver stage burden using bioluminescent imaging followed by subsequent tracking of patency by blood smear. This allows comparisons between the various GAPs for their ability to provide protection from an infectious sporozoite challenge.

Blood stage: To determine protection against the blood stage, mice can be challenged by iv-injecting 10,000 lethal Plasmodium infected RBC (iRBC). Parasitemia is monitored for effects of immunization on peak parasitemia as well as time to clearance/survival. As a comparison, it is noted that immunization with the late-arresting P. yoelii fabb/f– GAP elicited an immune response that both limits the peak parasitemia and clears parasites earlier than mock-immunized mice, whereas the early-arresting p52–/p36–/sap1– GAP does not similarly protect.

Sexual transmission stage: The transmission blocking activity of the GAP$^{Bs/Gam}$ will be evaluated by inoculating naive BALB/cJ mice with an intraperitoneal injection of Plasmodium GFP-LUC and allowing gametocytemia to reach approximately 1%, when robust male gamete exflagellation is apparent. At this time, ~100 starved A. stephensi mosquitoes will be allowed to obtain a blood meal from the infected mice one hour after iv injection (passive transfer) of immune sera from mice immunized with GAP$^{Bs/Gam}$ sporozoites. Control mice will receive sera from immunized with corresponding GAP sporozoites. A group of mice will also receive serum from mice immunized with Pys25 protein in adjuvant as described above. Fully engorged mosquitoes will be maintained for 10 days and then assessed for oocyst development by measuring luciferase activity, which has been previously shown as being accurate for determining oocyst burden. If antibodies bind to gametocytes and prevent transmission, luciferase activity will be significantly reduced.

In addition, the function of GAP$^{(Pf)Bs/Gam}$ will be assessed for its ability to generate antibodies capable of blocking parasite blood stage growth and transmission following immunization. Considering that *P. falciparum* blood stage parasites cannot infect rodent RBCs, antibody responses to *P. falciparum* antigens using well-established and standardized in vitro *P. falciparum* blood stage growth inhibition assays (GIA) and in vivo *P. falciparum* transmission blocking assays (TBA). For *P. falciparum* TBA, serum from mice immunized with $GAP^{(Pf)Bs/Gam}$ will be added to *P. falciparum* gametocyte culture prior to the standard *P. falciparum* membrane-feed assay where *A. stephensi* mosquitoes are allowed to feed to acquire the gametocyte-rich blood meal. A luciferase-expressing strain of *P. falciparum* allows routine analysis of the effect of the serum on the degree of oocyst development in the mosquito by bioluminescence. For both GIA and TBA, $GAP^{(Pf)Bs/Gam}$ immune sera will be compared to the control *P. falciparum* infections where the gametocyte cultures are mixed with sera produced in mice immunized with early arresting GAP. In addition, sera from mice immunized with recombinant Pfs25 and Pfs48/45 in adjuvant will be used as a positive control alongside serum from mice similarly immunized with irrelevant HIVenv protein for negative controls. Combined with results of the GIA, these experiments will allow determination if there is GIA and TBA of the $GAP^{(Pf)Bs/Gam}$.

The $GAP^{(Pf)Bs/Gam}$ are expected to be capable of inducing Bs/Gam-specific cellular and humoral immune responses. The proven success of the initially selected antigens, described herein, as protective targets in previous in vivo and in vitro assays bolsters confidence that the addition of such blood stage and/or gametocyte antigens to GAP, such as those described elsewhere herein, will provide enhanced cross-stage protection. These data are expected to confirm that the addition of blood stage and/or gametocyte antigens can improve vaccines, such as those based on GAP.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A live *Plasmodium* organism that is genetically modified to disrupt PlasMei2 gene function, wherein a functional PlasMei2 gene comprises a nucleic acid sequence with at least 90% identity to the sequence set forth in SEQ ID NO:9, wherein the *Plasmodium* organism further comprises at least one transgene encoding an antigen, and wherein the *Plasmodium* organism infects a human host.

2. The live *Plasmodium* organism of claim 1, wherein the *Plasmodium* organism does not develop into a merozoite stage capable of infecting a red blood cell within a mammalian intermediate host.

3. The live *Plasmodium* organism of claim 1, wherein the life cycle development of the *Plasmodium* organism within a mammalian intermediate host arrests at a late-liver stage.

4. The live *Plasmodium* organism of claim 1, wherein the *Plasmodium* organism is *P. falciparum, P. vivax, P. ovale, P. malariae*, or *P. knowlesi*.

5. The live *Plasmodium* organism of claim 1, wherein the *Plasmodium* organism is *P. falciparum*.

6. The live *Plasmodium* organism of claim 1, wherein the antigen encoded by the transgene stimulates a host immune response when expressed by the *Plasmodium* organism in the host.

7. The live *Plasmodium* organism of claim 6, wherein the transgene is under control of a promoter that results in transcription of the transgene during a sporozoite or liver stage of development.

8. The live *Plasmodium* organism of claim 1, wherein the *Plasmodium* organism is also genetically modified to disrupt liver-specific protein 2 (Lisp2) gene function.

9. The live *Plasmodium* organism of claim 8, wherein a functional LISP2 gene comprises a nucleic acid sequence with at least 90% identity to the sequence set forth in SEQ ID NO:13.

10. The live *Plasmodium* organism of claim 1, wherein the *Plasmodium* organism is also genetically modified to disrupt a P52, P36, fabb/f, and/or SAP1 gene function.

11. A method for stimulating an immune response against an antigen in a host subject, comprising administering to the host subject a live *Plasmodium* organism that comprises at least one transgene encoding the antigen and is further genetically modified to disrupt PlasMei2 gene function, wherein a functional PlasMei2 gene comprises a nucleic acid sequence with at least 90% identity to the sequence set forth in SEQ ID NO:9, and wherein the *Plasmodium* organism infects a human host and the antigen encoded by the transgene is expressed by the *Plasmodium* organism in the host and stimulates a host immune response.

12. The method of claim 11, wherein the *Plasmodium* organism does not develop into a merozoite stage capable of infecting a red blood cell within a mammalian intermediate host.

13. The method of claim 11, wherein the life cycle development of the *Plasmodium* organism within a mammalian intermediate host arrests at a late-liver stage.

14. The method of claim 11, wherein the *Plasmodium* organism is *P. falciparum, P. vivax, P. ovale, P. malariae*, or *P. knowlesi*.

15. The method of claim 11, wherein the transgene is under control of a promoter that results in transcription of the transgene during a sporozoite or liver stage of development.

16. The method of claim 15, wherein the antigen encoded by the transgene stimulates a host immune response when expressed by the *Plasmodium* organism in the liver stage of development within the host.

17. The method of claim 11, wherein the *Plasmodium* organism is also genetically modified to disrupt liver-specific protein 2 (Lisp2) gene function.

18. The method of claim 17, wherein a functional LISP2 gene comprises a nucleic acid sequence with at least 90% identity to the sequence set forth in SEQ ID NO:13.

19. The method of claim 11, wherein the *Plasmodium* organism is also genetically modified to disrupt a P52, P36, fabb/f, and/or SAP1 gene function.

* * * * *